(12) United States Patent  
Vallera

(10) Patent No.: US 9,155,798 B2  
(45) Date of Patent: Oct. 13, 2015

(54) RECEPTOR-TARGETING REAGENTS CONTAINING EPIDERMAL FACTOR RECEPTOR-BINDING AGENTS AND IL-13 RECEPTOR-BINDING AGENTS OR IL-4 RECEPTOR-BINDING AGENTS

(75) Inventor: Daniel A. Vallera, St. Louis Park, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 811 days.

(21) Appl. No.: 12/675,081

(22) PCT Filed: Aug. 25, 2008

(86) PCT No.: PCT/US2008/074268  
§ 371 (c)(1),  
(2), (4) Date: Dec. 16, 2010

(87) PCT Pub. No.: WO2009/029601  
PCT Pub. Date: Mar. 5, 2009

(65) Prior Publication Data  
US 2011/0091460 A1    Apr. 21, 2011

Related U.S. Application Data

(60) Provisional application No. 60/957,936, filed on Aug. 24, 2007.

(51) Int. Cl.  
*C07K 14/475* (2006.01)  
*C07K 14/485* (2006.01)  
*C07K 14/54* (2006.01)  
*C07K 14/71* (2006.01)  
*C07K 14/715* (2006.01)  
*G01N 33/53* (2006.01)  
(Continued)

(52) U.S. Cl.  
CPC ..... *A61K 47/48246* (2013.01); *A61K 47/48269* (2013.01); *A61K 51/088* (2013.01); *C07K 14/485* (2013.01); *C07K 14/5406* (2013.01); *C07K 14/5437* (2013.01); *C07K 2319/04* (2013.01); *C07K 2319/55* (2013.01); *C07K 2319/74* (2013.01)

(58) Field of Classification Search  
None  
See application file for complete search history.

(56) References Cited

U.S. PATENT DOCUMENTS 6,086,900 A * 7/2000 Draper ........................ 424/282.1  
6,429,498 B1 * 8/2002 Schelten et al.  
(Continued)

FOREIGN PATENT DOCUMENTS

WO    WO0002576  A2    1/2000  
WO    WO2004096254 A2   11/2004

OTHER PUBLICATIONS

Kaklamanis et al., Interleukin-4 receptor and epidermal growth factor receptor expression in colorectal cancer, Br. J. Cancer, 66:712-716, 1992.*

(Continued)

*Primary Examiner* — Claire Kaufman  
(74) *Attorney, Agent, or Firm* — Fish & Richardson P.C.

(57) ABSTRACT

The present disclosure features, inter alia, receptor-targeting reagents (e.g., immunotoxic receptor-targeting reagents), methods of binding a receptor-targeting reagent to a cell and methods for treating a variety of disorders. Also featured are methods, compositions, and kits for selecting an appropriate treatment modality for a subject and/or treating a variety of disorders.

15 Claims, 38 Drawing Sheets

(51) Int. Cl.
*A61K 47/48* (2006.01)
*A61K 51/08* (2006.01)

(56) References Cited

U.S. PATENT DOCUMENTS 6,864,359 B1 * 3/2005 Luo
2005/0142539 A1 6/2005 Herman

OTHER PUBLICATIONS

Leland et al., Human breast carcinoma cells express type II IL-4 receptors and are sensitive to antitumor activity of a chimeric IL-4-*Pseudomonas* exotoxin fusion protein in vitro and in vivo, Mol. Med. 6(3):165-178, 2000.*

Rahaman et al., Mutiple signaling pathways, #LB-74, Proc. Ann. Meeting of Am. Assoc. Canc. Res. 44:1337-1338, Jul. 2003.*

Kreitman et al., Properties of chimeric toxins with two recognition domains: interleukin 6 and tranforming growth factor alpha at different locations in *Pseudomonas* exotoxin, Bioconj. Chem. 3:63-68, 1992.*

Rand et al., Intratumoral administration of recombinant circularly permuted interleukin-4-*Pseudomonas* exotoxin in patients with high-grade glioma, Clin. Cancer Res. 6:2157-2165, Jun. 2000.*

Sampson et al., Progress report of a Phase I study of the intracerebral microinfusion of a recombinant chimeric protein coposed of transforming growth factor (TGF)-alpha and a mutated formof the Pesuedomonas exotoxin term PE-38 (TP-38) for the treatment of malignant brain tumors, J. Neuro-Oncol. 65:27-35, 2003.*

Onda et al., An immunotoxin with greatly reduced immunogenicity by indentification and removal of B cell epitopes, Proc. Natl. Acad. Sci., USA, 105(32):11311-11316, Aug. 12, 2008.*

Kreitman et al., Rational design of a chimeric toxin: an intramolecular location for the insertion of transforming growth factor alpha within *Pseudomonas* exotoxin as a targeting ligand, Bioconj. Chem. 3:58-62, 1992.*

Stish et al., Design and modification of EGF4KDEL 7Mut, a novel bispecific ligand-directed toxin, with decreased immunogenicity and potent anti-mesothelioma activity, Brit. J. Cancer, 101:1114-1123, 2009.*

Liu, T. et al., "Diphtheria Toxin-Epidermal Growth Factor Fusion Protein and *Pseudomonas* Exotoxin-Interleukin 13 Fusion Protein Exert Synergistic Toxicity against Human Glioblastoma Multiforme Cells", Bioconjugate Chem., 2003, 14:1107-1114.

Tyner, J., et al., "Blocking airway mucous cell metaplasia by inhibiting EGFR antiapoptosis and IL-13 transdifferentiation signals", J. Clin. Invest., Feb. 2006, 15:309-321.

Stish, B., et al., "A Bispecific Recombinant Cytotoxin (TTEGF13) Targeting Human Interleukin-13 and Epidermal Growth Factor Receptors in a Mouse Xenograft Model of Prostate Cancer", Cancer Therapy: Preclinical, No. 2007, 13(21):6486-6493.

Vallera et al., "A Bispecific Recombinant Immunotoxin, DT2219, Targeting Human CD19 and CD22 Receptors in a Mouse Xenograft Model of B-Cell Leukemia/Lymphoma," Clin Cancer Res., 11:3879-3888, May 15, 2005.

Todhunter et al., "A bispecific immunotoxin (DTAT13) targeting human IL-13 receptor (IL-13R) and urokinase-type plasminogen activator receptor (uPAR) in a mouse xenograft model," Protein Eng Des Sel., 17(2):157-164, Epub Feb. 13, 2004.

European search report for EP App. No. 08828457.5, dated Nov. 3, 2014, 6 pages.

Schmidt et al., "A bivalent single-chain antibody-toxin specific for ErbB-2 and the EGF receptor," Int J Cancer., 65(4):538-546, Feb. 8, 1996.

* cited by examiner

RECEPTOR-TARGETING REAGENTS CONTAINING EPIDERMAL FACTOR RECEPTOR-BINDING AGENTS AND IL-13 RECEPTOR-BINDING AGENTS OR IL-4 RECEPTOR-BINDING AGENTS

CROSS-REFERENCE TO RELATED APPLICATIONS

This application is a national phase filing under 35 U.S.C. §371 of international application number PCT/US2008/074268, filed Aug. 25, 2008, which claims priority to U.S. Provisional Application No. 60/957,936, filed Aug. 24, 2007. The entire disclosures of both of these applications are incorporated herein by reference in their entirety.

STATEMENT REGARDING FEDERALLY SPONSORED RESEARCH OR DEVELOPMENT

The research described in this application was supported by U.S. Public Health Service grants (grant nos. RO1-CA36725, RO1-CA082154, and R01-CA108637) from the National Cancer Institute of the National Institutes of Health. Thus, the government has certain rights in the invention.

TECHNICAL FIELD

The invention is generally in the field of immunotoxins, which are useful in inhibiting the proliferation (or killing) of pathogenic cells, e.g., cancer cells.

BACKGROUND

Cancer (e.g., prostate cancer or glioblastoma such as glioblastoma multiforme) is a leading cause of death in Western cultures and is generally characterized by excessive, uncontrolled cell proliferation in defiance of normal restraints on cell growth. These cancer cells can invade and colonize (metastasize) territories normally reserved for other cells. Modes of cancer therapy include chemotherapy, surgery, radiation, and combinations of these treatments. While many anti-cancer agents have been developed, there remains a need for more effective therapies.

Immunotoxins are molecules that contain targeting domains that direct the molecules to target cells of interest (e.g., cancer cells or immune cells mediating an inflammatory disorder) and toxic domains that inhibit the proliferation of (or kill) the target cells.

SUMMARY

The present disclosure details the surprising discovery that bispecific, immunotoxic receptor-targeting reagents comprising an epidermal growth factor receptor (EGFR)-binding domain and an interleukin-13 receptor (IL13R)-binding domain (or an interleukin-4 receptor (IL4R)-binding domain) were much more effective at killing cancer cells and reducing tumor burden of mice than their monospecific receptor-targeting reagent counterparts. Thus, the bispecific receptor-targeting reagents described herein are useful, inter alia, in methods of treating a variety of proliferative disorders including cancer and inflammatory disorders.

The disclosure also details the surprising discovery that the toxicity of immunotoxic receptor-targeting reagents administered to a subject can be decreased by administering to the subject a non-immunotoxic receptor-targeting reagent prior to the immunotoxin. Thus, methods of administering a non-immunotoxic receptor-targeting reagent prior to an immunotoxin therapy are useful in, for example, decreasing the number or the severity of one or more side-effects of an immunotoxic therapy. Such methods can be used by medical practitioners, e.g., to formulate a therapeutic regimen for a subject that effectively treats a disease (such as a cancer or an inflammatory disorder) without substantially affecting healthy tissues in the subject.

In one aspect, the disclosure features a receptor-targeting reagent comprising: (a) a first targeting domain comprising an epidermal growth factor receptor (EGFR)-binding agent and (b) a second targeting domain comprising an IL-13 receptor (IL13R)-binding agent or an IL-4 receptor (IL4R)-binding agent, wherein (a) is bound to (b).

In another aspect, the disclosure features a receptor-targeting reagent comprising: (a) a first targeting domain comprising an epidermal growth factor receptor (EGFR)-binding agent and (b) a second targeting domain comprising an IL-4 receptor (IL4R)-binding agent, wherein (a) is bound to (b).

In another aspect, the disclosure features a receptor-targeting reagent comprising: (a) a first targeting domain comprising an epidermal growth factor receptor (EGFR)-binding agent and (b) a second targeting domain comprising an IL-13 receptor (IL13R)-binding agent, wherein (a) is bound to (b).

In some embodiments of any of the receptor-targeting reagents described herein, the IL13R-binding agent can contain, or consist of, an antibody that binds to the IL13R or an antigen-binding fragment thereof or an IL-13 polypeptide or an IL13R-binding fragment thereof.

In some embodiments of any of the receptor-targeting reagents described herein, the IL4R-binding agent can contain, or consist of, an antibody that binds to the IL4R or an antigen-binding fragment thereof or an IL-4 polypeptide or an IL4R-binding fragment thereof.

In some embodiments of any of the receptor-targeting reagents described herein, the EGFR-binding agent can contain, or consist of (i) an antibody that binds to the EGFR or an antigen-binding fragment thereof; (ii) an epidermal growth factor polypeptide or an EGFR-binding fragment thereof; (iii) a betacellulin polypeptide or an EGFR-binding fragment thereof; (iv) a transforming growth factor alpha polypeptide or EGFR-binding fragment thereof; (v) an amphiregulin polypeptide or EGFR-binding fragment thereof; (vi) an epiregulin polypeptide or EGFR-binding fragment thereof; or (vii) a heparin-binding EGF polypeptide or EGFR-binding fragment thereof. The antibody (e.g., the antibody that binds to an EGFR or IL13R) or antigen-binding fragment can be, e.g., a monoclonal antibody, a polyclonal antibody, a humanized antibody, a fully human antibody, a single chain antibody, a chimeric antibody, an $F_{ab}$ fragment, an $F_{(ab')2}$ fragment, an $F_{ab'}$ fragment, an $F_v$ fragment, or an $scF_v$ fragment.

In some embodiments, (a) and (b) can be bound to each other by a covalent bond or a non-covalent bond. In some embodiments, (a) and (b) can be bound to each other by a first and second member of a binding pair. The binding pair can be streptavidin (or avidin) and biotin. In some embodiments, the receptor-targeting reagent can contain, or consist of, a fusion protein comprising (a) and (b).

In some embodiments, the receptor-targeting reagents can further comprise a toxic domain, wherein the receptor-targeting reagent is immunotoxic. The toxic domain can contain, or consist of, a small molecule, a radiological agent, and/or a toxic polypeptide. The toxic polypeptide can consist of, or contain, a *Diphtheria* toxin or a biologically active fragment thereof. The toxic polypeptide can consist of, or contain, SEQ ID NO:9 or SEQ ID NO:10. The toxic polypeptide can consist of, or contain, a *Pseudomonas* exotoxin A or a biologically active fragment thereof. The toxic polypeptide can contain, or consist of, SEQ ID NO:11 or SEQ ID NO:12. The toxic polypeptide can be, e.g., a *Pseudomonas* exotoxin (PE), bryodin, gelonin, sarcin, aspergillin, restrictocin, angiogenin, saporin, abrin, a prokaryotic ribonuclease, a eukaryotic ribonuclease, ricin, pokeweed antiviral protein (PAP), a pro-apoptotic polypeptide, a ribosomal inhibitory protein, or a biologically active fragment of any of the foregoing. The pro-apoptotic polypeptide can be, e.g., Bax, Fas, Bad, Bak, Bim, Bik, Bok, Hrk, FasL, TRAIL, or TNF-alpha.

In some embodiments, the receptor-targeting reagents can contain a toxic domain that has been modified to reduce or prevent immunogenicity of the polypeptide in a subject.

In some embodiments, (a), (b), or (a) and (b) can be bound to the toxic domain by a non-covalent bond or a covalent bond. The receptor-targeting reagent can contain a fusion protein comprising: the toxic domain and (a), (b), or (a) and (b). (a) and/or (b) can be bound to the toxic domain in any configuration described herein.

In some embodiments, the receptor-targeting reagent can further contain one or more linker moieties. At least one of the one or more linker moieties can be a peptide linker. The peptide linker can contain, or consist of, e.g.: SEQ ID NO:13 or SEQ ID NO:14 or any other linker peptides described herein.

In some embodiments, the receptor-targeting reagents can contain, or consist of, any one of SEQ ID NOS:1-3. In some embodiments, the receptor-targeting reagents can contain, or consist of, any one of SEQ ID NOS:18-20.

In some embodiments, the receptor-targeting reagent can contain one or more detectable labels.

In some embodiments, the receptor-targeting reagents can bind to a cell. The cell can be, e.g., a mammalian cell such as a human cell. The cell can express an IL13R and/or an EGFR.

In another aspect, the disclosure features a pharmaceutical composition containing any of the receptor-targeting reagents described above and a pharmaceutically acceptable carrier.

In another aspect, the disclosure provides a nucleic acid encoding any of the polypeptides described herein (e.g., any one of SEQ ID NOS:1-22).

In another aspect, the disclosure provides a nucleic acid encoding a fusion protein comprising any of the polypeptide receptor-targeting reagents described above. For example, the nucleic acid can encode a fusion protein containing, or consisting of, any one of SEQ ID NOS:1-3. In another example, the nucleic acid can encode a fusion protein containing, or consisting of, any one of SEQ ID NOS:18-20.

In yet another aspect, the disclosure features: (i) a vector containing any of the nucleic acids described above; (ii) an expression vector containing any of the nucleic acids described above; and/or (iii) a cell containing the expression vector of (ii).

In another aspect, the disclosure provides a method of producing a fusion protein. The method includes the step of culturing a cell comprising the expression vector described immediately above under conditions suitable for expression of the fusion protein. The method can also include the step of isolating the protein from the cells or the culture medium in which the cells are cultured.

In another aspect, the disclosure features a polypeptide encoded by any of the nucleic acids described above.

In yet another aspect, the disclosure features an in vitro method for binding a receptor-targeting reagent to a cell, which method includes the step of contacting a cell with any of the receptor-targeting reagents described above. The method can also include the step of determining whether the cell expresses an EGFR, an IL13R, or an IL4R. The cell can express an EGFR, and IL4R, and/or an IL13R.

In yet another aspect, the disclosure features an in vitro method for binding a receptor-targeting reagent to a cell, which method includes the step of contacting a cell with any of the receptor-targeting reagents described above. The method can also include the step of determining whether the cell expresses an EGFR or an IL13R. The cell can express an EGFR and/or an IL13R.

In some embodiments of any of the methods described herein, the cell can be a cancer cell such as, but not limited to, a lung cancer cell, a breast cancer cell, a colon cancer cell, a pancreatic cancer cell, a renal cancer cell, a stomach cancer cell, a liver cancer cell, a bone cancer cell, a hematological cancer cell, a neural tissue cancer cell, a melanoma cell, a thyroid cancer cell, a glioblastoma cell, an ovarian cancer cell, a testicular cancer cell, a prostate cancer cell, a cervical cancer cell, a vaginal cancer cell, and a bladder cancer cell. The cell can be an immune cell such as a T cell or a B cell. The cell can be, e.g., a mammalian cell such as a human cell.

In yet another aspect, the disclosure features an in vivo method for binding a receptor-targeting reagent to a cell. The method includes the step of delivering to a subject any of the receptor-targeting reagents described above. The method can also include the step of determining whether the subject has a cancer. The cancer can be, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, glioblastoma, vaginal cancer, or bladder cancer. The cell can also be an immune cell such as a T cell or a B cell. The subject can be a mammal such as a human. The subject can be one who has, is suspected of having, or at risk of developing, an inflammatory condition such as any of those described herein. The method can also include the step of determining if one or more one or more cells of the subject's cancer express an EGFR, an IL4R, and/or an IL13R. The method can further include the step of determining whether the receptor-targeting reagent bound to the cell or whether the receptor-targeting reagent killed a cell (or inhibited the proliferation of the cell). In embodiments where the subject is one having, suspected of having, or at risk of developing an inflammatory condition, the method can be a method of treating an inflammatory condition.

In another aspect, the disclosure features an in vitro method for inhibiting the growth of a cell. The method includes the step of contacting a cell with any of the immunotoxic receptor-targeting reagents described above, wherein contacting the cell with the immunotoxic receptor-targeting reagent inhibits the growth of the cell. In some embodiments, the immunotoxic receptor-targeting reagent can kill a cell, thus the method can be an in vitro method for killing a cell. The cell can be a cancer cell such as any of those described above.

In yet another aspect, the disclosure provides an in vivo method for treating a cancer in a subject, which method includes the step of delivering to a subject having, suspected of having, or at risk of developing, a cancer any of the receptor-targeting reagents described above. The receptor-targeting reagent can be immunotoxic (i.e., contain at least one toxic domain). Delivering can include administering the receptor-targeting reagent to the subject, e.g., intravenously and/or through the use of a systemic pump.

In another aspect, the disclosure features a method for decreasing one or more (e.g., two, three, four, five, six, seven, eight, nine, or 10 or more) toxic side-effects of an immunotoxic therapy in a subject. The method includes the step of, prior to delivering to a subject an immunotoxin (e.g., any of the immunotoxic receptor-targeting reagents described herein), delivering to the subject a non-immunotoxic reagent (e.g., any of the non-immunotoxic receptor-targeting reagents described herein), wherein the non-immunotoxic reagent does not contain a toxic domain.

In some embodiments, the non-immunotoxic reagent can have the same binding specificity as the immunotoxin.

In another aspect, the disclosure provides a method for decreasing one or more (e.g., two, three, four, five, six, seven, eight, nine, or 10 or more) toxic side-effects of an immunotoxic therapy in a subject. The method includes the step of, prior to delivering to a subject any of the immunotoxic receptor targeting reagents described above, delivering to the subject a receptor-targeting reagent comprising: (a) an epidermal growth factor receptor (EGFR)-binding agent and (b) an IL-13 receptor (IL13R)-binding agent, wherein (a) is bound to (b) and wherein the receptor-targeting reagent does not comprise a toxic domain.

In another aspect, the disclosure features a method for treating a cancer. The method includes the steps of: delivering to a subject with cancer a receptor-targeting reagent comprising (a) an epidermal growth factor receptor (EGFR)-binding agent and (b) an IL-13 receptor (IL13R)-binding agent or an IL-4 receptor (IL4R)-binding agent, wherein (a) is bound to (b), wherein the receptor-targeting reagent does not comprise a toxic domain; and delivering to the subject any of the immunotoxic receptor targeting reagents described herein.

In another aspect, the disclosure features a method for treating a cancer. The method includes the steps of delivering to a subject with cancer a receptor-targeting reagent comprising (a) an epidermal growth factor receptor (EGFR)-binding agent and (b) an IL-4 receptor (IL4R)-binding agent, wherein (a) is bound to (b), wherein the receptor-targeting reagent does not comprise a toxic domain; and delivering to the subject any of the immunotoxic receptor targeting reagents described herein.

In another aspect, the disclosure features a method for treating a cancer. The method includes the steps of: delivering to a subject with cancer a receptor-targeting reagent comprising (a) an epidermal growth factor receptor (EGFR)-binding agent and (b) an IL-13 receptor (IL13R)-binding agent, wherein (a) is bound to (b), wherein the receptor-targeting reagent does not comprise a toxic domain; and delivering to the subject any of the immunotoxic receptor targeting reagents described herein.

In yet another aspect, the disclosure features a method for selecting a therapeutic agent for a mammal with cancer. The method includes the steps of: determining if one or more cancer cells of a cancer in a mammal express an IL13R, an IL4R, or an EGFR; and if one or more of the cancer cells express an IL13R, an IL4R, or an EGFR, selecting as a therapeutic agent for the mammal any of the receptor-targeting reagents described above (e.g., any of the immunotoxic receptor-targeting reagents described above). In some embodiments, the method can also include the step of after determining that one or more of the cells of the cancer express an IL13R, an IL4R, or an EGFR, delivering to the subject the selected receptor-targeting reagent.

In yet another aspect, the disclosure features a method for selecting a therapeutic agent for a mammal with cancer. The method includes the steps of: determining if one or more cancer cells of a cancer in a mammal express an IL4R or an EGFR; and if one or more of the cancer cells express an IL4R or an EGFR, selecting as a therapeutic agent for the mammal any of the receptor-targeting reagents described above (e.g., any of the immunotoxic receptor-targeting reagents described above). In some embodiments, the method can also include the step of after determining that one or more of the cells of the cancer express an IL4R or an EGFR, delivering to the subject the selected receptor-targeting reagent.

In yet another aspect, the disclosure features a method for selecting a therapeutic agent for a mammal with cancer. The method includes the steps of: determining if one or more cancer cells of a cancer in a mammal express an IL13R or an EGFR; and if one or more of the cancer cells express an IL13R or an EGFR, selecting as a therapeutic agent for the mammal any of the receptor-targeting reagents described above (e.g., any of the immunotoxic receptor-targeting reagents described above). In some embodiments, the method can also include the step of after determining that one or more of the cells of the cancer express an IL13R or an EGFR, delivering to the subject the selected receptor-targeting reagent.

In another aspect, the disclosure features a method for selecting a therapeutic agent for a mammal with cancer, which method includes the step of selecting as a therapeutic agent for a mammal with cancer any of the immunotoxic receptor-targeting reagents described above if one or more cancer cells of the mammal's cancer express an IL13R, an IL4R, or an EGFR. The method can also include the step of determining if one or more of the cancer cells in a mammal express an IL13R, an IL4R, or an EGFR.

In another aspect, the disclosure features a method for selecting a therapeutic agent for a mammal with cancer, which method includes the step of selecting as a therapeutic agent for a mammal with cancer any of the immunotoxic receptor-targeting reagents described above if one or more cancer cells of the mammal's cancer express an IL13R or an EGFR. The method can also include the step of determining if one or more of the cancer cells in a mammal express an IL13R or an EGFR.

In some embodiments of any of the in vivo methods described above, the subject can be, e.g., a mammal such a human.

In some embodiments, any of the in vivo methods described above can include the step of determining if the subject has, or is at risk of developing, a cancer. The methods can also include the step of determining if one or more cancer cells of the subject's cancer express an IL13R, an IL4R, and/or an EGFR. The in vivo methods can also include the step of: (i) determining whether the receptor-targeting reagent bound to the cell (e.g., a cell expressing an EGFR, an IL4R, and/or an IL13R such as a cancer cell or an immune cell); and/or (ii) determining if the receptor-targeting reagent inhibited the proliferation of the cell or killed the cell to which it bound.

In yet another aspect, the disclosure features a kit comprising: any of the receptor-targeting reagents described above; and instructions for administering the receptor-targeting reagent. The kit can also include one or more pharmaceutically acceptable carriers and/or a pharmaceutically acceptable diluent.

In another aspect, the disclosure features a kit comprising: one or more reagents for detecting expression of an IL13R, an IL4R, or an EGFR; and instructions for administering to a subject any of the receptor-targeting reagents described herein if the expression of an IL13R or an EGFR is detected.

In another aspect, the disclosure features a kit comprising: one or more reagents for detecting expression of an IL4R or an EGFR; and instructions for administering to a subject any of the receptor-targeting reagents described herein if the expression of an IL4R or an EGFR is detected.

In another aspect, the disclosure features a kit comprising: one or more reagents for detecting expression of an IL13R or an EGFR; and instructions for administering to a subject any of the receptor-targeting reagents described herein if the expression of an IL13R or an EGFR is detected.

In another aspect, the disclosure features an article of manufacture comprising: a container; and a composition contained within the container, wherein the composition comprises an active agent for treating cancer in a mammal, wherein the active agent in the composition comprises any of the immunotoxic receptor-targeting reagents described above, and wherein the container has a label indicating that the composition is for use in treating cancer in a mammal. The label can further indicate that the composition is to be administered to the mammal if one or more cancer cells of the mammal's cancer express an IL13R, an IL4R, or an EGFR. The article of manufacture can also include instructions for administering the active agent to the mammal. The composition can be in liquid form, or dried or lyophilized.

In another aspect, the disclosure features an article of manufacture comprising: a container; and a composition contained within the container, wherein the composition comprises an active agent for treating cancer in a mammal, wherein the active agent in the composition comprises any of the immunotoxic receptor-targeting reagents described above, and wherein the container has a label indicating that the composition is for use in treating cancer in a mammal. The label can further indicate that the composition is to be administered to the mammal if one or more cancer cells of the mammal's cancer express an IL4R or an EGFR. The article of manufacture can also include instructions for administering the active agent to the mammal. The composition can be in liquid form, or dried or lyophilized.

In another aspect, the disclosure features an article of manufacture comprising: a container; and a composition contained within the container, wherein the composition comprises an active agent for treating cancer in a mammal, wherein the active agent in the composition comprises any of the immunotoxic receptor-targeting reagents described above, and wherein the container has a label indicating that the composition is for use in treating cancer in a mammal. The label can further indicate that the composition is to be administered to the mammal if one or more cancer cells of the mammal's cancer express an IL13R or an EGFR. The article of manufacture can also include instructions for administering the active agent to the mammal. The composition can be in liquid form, or dried or lyophilized.

As used herein, "bound" or "bound to" in the context of an interaction between two or more atoms or molecular units, refers to any covalent or non-covalent bonding of two or more atoms or molecular units (e.g., two or more domains such as targeting domains or toxic domains) to each other. The chemical nature of covalent bonds (two atoms sharing one or more pairs of valence electrons) are known in the art and include, e.g., disulfide bonds or peptide bonds. A non-covalent bond is a chemical bond between atoms or molecules that does not involve the sharing of pairs of valence electrons. For example, non-covalent interactions include, e.g., hydrophobic interactions, hydrogen-bonding interactions, ionic bonding, Van der Waals bonding, or dipole-dipole interactions. Examples of such non-covalent interactions include antibody-antigen complexing or binding pair interactions (interactions of a first and second member of a binding pair such as the interaction between streptavidin and biotin). The term "(a) bound to (b)", where (a) and (b) are targeting domains, means (a) bound to (b) via: (i) any one of the above chemical bonds; (ii) a linker (including a binding pair); or (iii) a toxic domain. The term "(a) directly bound to (b)" means (a) bound to (b) via any of (i) or (ii), but not (iii).

"Polypeptide" and "protein" are used interchangeably and mean any peptide-linked chain of amino acids, regardless of length or post-translational modification.

Any of the various components (e.g., domains) of the receptor-targeting reagents described herein, e.g., the EGFR-binding domains, the IL13R-binding domains, the IL4R-binding domains, or the toxic domains comprising toxic polypeptides) can consist of, or include, the full-length, wild-type forms of the polypeptides. Where mature and immature forms of a polypeptide exist, the one used in the a receptor-targeting agent of the invention is preferably the mature form. For example, an EGFR-binding domain can consist of, or be, a full-length epidermal growth factor (e.g., a human epidermal growth factor such as the epidermal growth factor with the amino acid sequence SEQ ID NO:6).

The disclosure also provides (i) biologically active variants and (ii) biologically active fragments or biologically active variants thereof, of the wild-type, full-length polypeptides (e.g., the various polypeptide domains of receptor-targeting reagents) described herein. Biologically active variants of full-length, preferably mature, wild-type proteins or fragments of the proteins can contain additions, deletions, or substitutions. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (a) full-length, wild-type polypeptides or fragments thereof containing at least five amino acids; and (b) internal or terminal (C or N) irrelevant or heterologous amino acid sequences. In the context of such fusion proteins, the term "heterologous amino acid sequences" refers to an amino acid sequence other than (a). A fusion protein containing a peptide described herein and a heterologous amino acid sequence thus does not correspond in sequence to all or part of a naturally occurring protein. A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences can also be proteins useful as diagnostic or detectable markers, for example, luciferase, green fluorescent protein (GFP), or chloramphenicol acetyl transferase (CAT). In some embodiments, the fusion protein contains a signal sequence from another protein such as a KDEL (SEQ ID NO:15)

sequence or any other described herein. In some embodiments, the fusion protein can contain a carrier (e.g., KLH) useful, e.g., in eliciting an immune response (e.g., for antibody generation; see below). In some embodiments, a fusion protein can contain an exogenous methionine amino acid residue. In some embodiments, the fusion protein can contain one or more linker moieties (see below). Heterologous sequences can be of varying length and in some cases can be longer sequences than the full-length target proteins to which the heterologous sequences are attached.

A "fragment" as used herein, refers to a segment of the polypeptide that is shorter than a full-length, immature protein. Fragments of a protein can have terminal (carboxy or amino-terminal) and/or internal deletions. Generally, fragments of a protein will be at least four (e.g., at least five, at least six, at least seven, at least eight, at least nine, at least 10, at least 12, at least 15, at least 18, at least 25, at least 30, at least 35, at least 40, at least 50, at least 60, at least 65, at least 70, at least 75, at least 80, at least 85, at least 90, or at least 100 or more) amino acids in length.

Biologically active fragments or biologically active variants of any of the targeting polypeptides or toxic polypeptides described herein have at least 25% (e.g., at least: 30%; 40%; 50%; 60%; 70%; 75%; 80%; 85%; 90%; 95%; 97%; 98%; 99%; 99.5%, or 100% or even greater) of the activity of the wild-type, full-length polypeptide. In the case of a targeting polypeptide, the relevant activity is the ability of the targeting polypeptide to bind to the target of interest (e.g., an EGFR receptor, an IL13R, or an IL4R). In the case of a toxic polypeptide, the relevant activity is the ability to inhibit the proliferation of a cell (or kill the cell).

Depending on their intended use, the polypeptides, biologically active fragments, or biologically active variants thereof can be of any species, such as, e.g., nematode, insect, plant, bird, fish, reptile, or mammal (e.g., a mouse, rat, rabbit, hamster, gerbil, dog, cat, goat, pig, cow, horse, whale, monkey, or human). In some embodiments, biologically active fragments or biologically active variants include immunogenic and antigenic fragments of the proteins. An immunogenic fragment is one that has at least 25% (e.g., at least: 30%; 40%; 50%; 60%; 70%; 75%; 80%; 85%; 90%; 95%; 97%; 98%; 99%; 99.5%, or 100% or even more) of the ability of the relevant full-length, wild-type protein to stimulate an immune response (e.g., an antibody response or a cellular immune response) in an animal of interest. An antigenic fragment of a protein is one having at least 25% (e.g., at least: 30%; 40%; 50%; 60%; 70%; 75%; 80%; 85%; 90%; 95%; 97%; 98%; 99%; 99.5%, or 100% or even greater) of the ability of the relevant full-length, wild-type protein to be recognized by an antibody specific for the protein or a T cell specific to the protein.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., methods for inhibiting the proliferation of a cancer cell (or killing a cancer cell), will be apparent from the following description, from the drawings and from the claims.

BRIEF DESCRIPTION OF THE DRAWINGS

FIG. 17A: No treatment; or 17B: DTEGF13 treatment. Mice in the DTEGF13-treated group received 2.5 µg DTEGF13 injected i.t. The lines under the abscissa indicate days of injection.

FIG. 17C depicts the average tumor volume of animals in each treatment group. FIG. 17D depicts the growth of individual tumors treated with DTEGF13. FIG. 17E depicts animal weights of individual mice (mouse 1 to mouse 5) in the DTEGF13 treatment group.

FIG. 18A: a xenograft model of pancreatic cancer was established by injecting male nude mice (no prior irradiation) with $1\times10^7$ MIA PaCa-2 cells in a 1:1 mixture of DMEM:Matrigel. Mice were randomized into three groups (n=6/group) on day 15 when the average tumor volume was approximately 75 mm$^3$. Treated animals were injected i.t. with 2.5 µg of either DTEGF13, DT2222, or no treatment. A total of 6 injections were given over the course of two weeks as indicated by the lines below each graph. FIG. 18B depicts the weights of each animal in the study administered the DTEGF13 reagent (data shown in FIG. 18A).

DETAILED DESCRIPTION

Figure 1A:
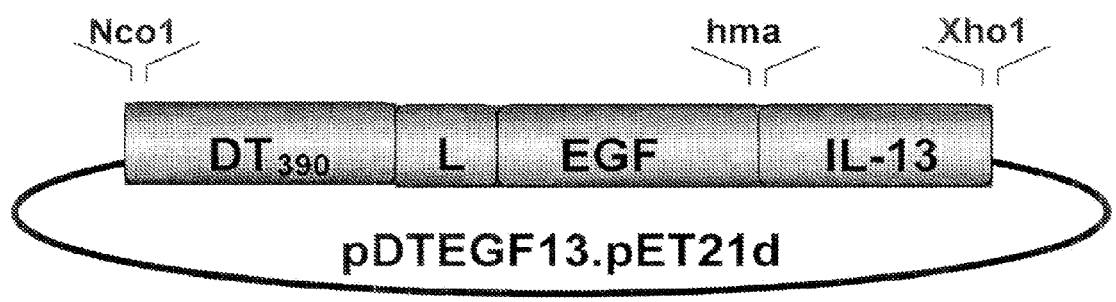
FIG. 1A is a schematic diagram depicting the DTEGF13 construct. The gene fragment encoding the single-chain bispecific immunotoxin DTEGF13 was created using overlap extension PCR. This construct consisted of (from 5' to 3') a nucleic acid encoding a truncated diphtheria toxin molecule ($DT_{390}$), a seven amino acid (EASPPGE) (SEQ ID NO:14) linker (L), human epidermal growth factor (EGF), a flexible 20 amino acid segment of human muscle aldolase (hma), and interleukin-13 (IL-13). Using the NcoI/XhoI restriction sites the nucleic acid sequence encoding DTEGF13 was cloned in the pET21d bacterial expression vector.

The present disclosure features, inter alia, receptor-targeting reagents (e.g., immunotoxic receptor-targeting reagents), which are useful in a variety of in vitro, in vivo, and ex vivo methods. For example, the receptor-targeting reagents are useful in methods of binding a receptor-targeting reagent to a cell. As detailed in the accompanying Examples, immunotoxic forms of the receptor-targeting reagents described herein were able to inhibit the growth of cancer cells in culture and in whole animal models, and non-immunotoxic forms of the receptor-targeting reagents reduced the toxic side-effects associated with immunotoxic therapy. Thus, the receptor-targeting reagents described herein are useful in treating a variety of proliferative disorders such as, but not limited to, cancers and inflammatory disorders.

Also provided herein are methods, compositions, and kits useful for selecting an appropriate treatment modality for a subject (e.g., a subject with a cancer or inflammatory disorder) and/or treating a variety of proliferative disorders.

Receptor-Targeting Reagents

The disclosure features receptor-targeting reagents, which reagents contain: (a) a first targeting domain containing an epidermal growth factor receptor (EGFR)-binding agent and (b) a second targeting domain containing an IL-13 receptor (IL13R)-binding agent or an IL-4 receptor (IL4R)-binding agent, wherein (a) is bound to (b).

The EGFR-binding agent can be any agent that selectively binds to an EGFR (e.g., an EGFR/HER1/ErbB1, a HER2/ErbB2/neu, a HER3, or a HER4). For example, the EGFR-binding agent can include all, or an EGFR-binding fragment, of an antibody specific for an EGFR. The EGFR-binding agent consist of, or contain, all or part (an EGFR-binding fragment) of a natural ligand for EGFR. For example, the EGFR-binding can consist of, or contain, a natural ligand for a HER1 such as, but not limited to, an epidermal growth factor polypeptide, a betacellulin polypeptide, a transforming growth factor alpha polypeptide, an amphiregulin polypeptide, an epiregulin polypeptide, a heparin-binding EGF polypeptide, or EGFR-binding fragment of any of the foregoing. An exemplary amino acid sequence for a full length, mature (lacking a signal peptide) human EGF polypeptide is as follows:

(SEQ ID NO: 6)
NSDSECPLSHDGYCLHDGVCMYIEALDKYACNCVVGYIGERCQYRDLKWW

ELR.

Additional natural ligands for an EGFR suitable for the methods described herein include, but are not limited to: neuregulins (also known as heregulins, neu differentiation factors, or glial growth factors; e.g., heregulin α, heregulin β) and the neuregulin-2s.

In some embodiments, the EGFR-binding agent can be a small molecule that binds to an EGFR, e.g., a small molecule that binds to an EGF-binding site of an EGFR.

The receptor-targeting reagents can contain a first targeting domain containing an EGFR-binding agent and a second targeting domain containing an IL13R-binding agent. The IL13R-binding agent can be any agent that selectively binds to an IL13R (e.g., a mammalian IL13R such as human IL13R). For example, the IL13R-binding agent can consist of, or contain, an antibody that binds to the IL13R or an antigen-binding fragment thereof. The IL13R-binding agent can be, e.g., all or part (an IL13R-binding fragment) of a natural ligand for IL13R. For example, the IL13R-binding agent can also consist of, or contain, an IL-13 polypeptide or an IL13-binding fragment thereof. An exemplary amino acid sequence for a full length, mature (lacking a signal peptide) human IL-13 polypeptide is as follows:

(SEQ ID NO: 7)
GPVPPSTALRELIEELVNITQNQKAPLCNGSMVWSINLTAGMYCAALESL

INVSGCSAIEKTQRMLSGFCPHKVSAGQFSSLHVRDTKIEVAQFVKDLLL

HLKKLFREGRFN.

In some embodiments, the IL13R-binding agent can be a small molecule that binds to an IL13R, e.g., a small molecule that binds to an IL-13-binding site of an IL13R.

The receptor-targeting reagents can contain a first targeting domain containing an EGFR-binding agent and a second targeting domain containing an IL4R-binding agent. The IL4R-binding agent can be any agent that selectively binds to an IL4R (e.g., a mammalian IL4R such as human IL4R). For example, the IL4R-binding agent can consist of, or contain, an antibody that binds to the IL4R or an antigen-binding fragment thereof. The IL4R-binding agent can be, e.g., all or part (an IL4R-binding fragment) of a natural ligand for IL4R. For example, the IL4R-binding agent can also consist of, or contain, an IL-4 polypeptide or an IL4-binding fragment thereof. An exemplary amino acid sequence for a full length, human IL-4 polypeptide is as follows.

(SEQ ID NO: 17)
MGLTSQLLPPLFFLLACAGNFVHGHKCDITLQEIIKTLNSLTEQKTLCTE

LTVTDIFAASKNTTEKETFCRAATVLRQFYSHHEKDTRCLGATAQQFHRH

KQLIRFLKRLDRNLWGLAGLNSCPVKEANQSTLENFLERLKTIMREKYSK

CSS.

In some embodiments, the IL4R-binding agent can be a small molecule that binds to an IL4R, e.g., a small molecule that binds to an IL4-binding site of an IL4R.

The EGFR-, IL13R-, or IL4R-specific antibody (or antigen-binding fragment thereof) described above can be, e.g., a monoclonal antibody, a polyclonal antibody, a humanized antibody, a fully human antibody, a single chain antibody, a chimeric antibody, or an Fab fragment, an F(ab')$_2$ fragment, an Fab' fragment, an Fv fragment, or an scFv fragment of an EGFR-specific antibody. Methods for making such antibodies are described below (see "Methods For Generating Antibodies").

In some embodiments, the receptor-targeting reagents can be immunotoxic. That is, any of the receptor-targeting reagents described herein can further contain one or more (e.g., two or more, three or more, four or more, five or more, six or more, seven or more, eight or more, nine or more, 10 or more, 15 or more, or 20 or more) toxic domains.

A toxic domain can consist of, or include, e.g., a small molecule. Small molecules that are suitable for toxic domains include, e.g., chemotherapeutic agents such as, but not limited to, cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned. Where the receptor-targeting reagent contains more than one small molecule, the various small molecules can each be the same, different, or a mixture of both of the aforementioned.

The toxic domain can consist of, or contain, at least one (e.g., at least two, at least three, at least four, at least five, at least six, at least seven, at least eight, at least nine, at least 10, at least 15, or at least 20) radionuclide(s). The at least one radionuclide can be, e.g., $^{90}$Y, $^{186}$Re, $^{188}$Re, $^{64}$Cu, $^{67}$Cu, $^{212}$Pb, $^{212}$Bi, $^{213}$Bi, $^{123}$I, $^{125}$I, $^{131}$I, $^{211}$At, $^{32}$P, $^{177}$Lu, $^{47}$Sc, $^{105}$Rb, $^{109}$Pd, $^{153}$Sm, or $^{199}$Au.

In some embodiments, the radionuclide atom can be can be part of a larger molecule (e.g., $^{125}$I in meta-[$^{125}$I]iodophenyl-N-hydroxysuccinimide ([$^{125}$I]mIPNHS), which binds via free amino groups to form meta-iodophenyl (mIP) derivatives of relevant proteins (see, e.g., Rogers et al. (1997) J. Nucl. Med. 38:1221-1229), or a chelate (e.g., radioactive metal atoms such as $^{99m}$Tc, $^{188}$Re, $^{186}$Re, $^{90}$Y, $^{212}$Pb, $^{212}$Bi, $^{64}$Cu, $^{67}$Cu, $^{177}$Lu, $^{47}$Sc, $^{105}$Rb, $^{109}$Pd, $^{153}$Sm, $^{199}$Au chelated to, for example, hydroxamic acids, DOTA, or DTPA), which are themselves part of the receptor-targeting reagent. Where the receptor-targeting reagent contains more than one radionuclide atom, the various radionuclide atoms can be either all the same radionuclide (e.g., more than one of $^{90}$Y), all different radionuclides, or a mixture of both of the aforementioned. The radionuclides can emit α-, β-, or γ-radiation or a combination of two or more of these types of irradiation.

As is described in the accompanying Examples, the toxic domain can contain, or consist of, a toxic polypeptide. For example, the toxic polypeptide can be a *Diphtheria* toxin or a biologically active fragment (a toxic fragment) or variant (a toxic variant) thereof.

An exemplary amino acid sequence for a full-length *Diphtheria* toxin (which contains the amino-terminal leader sequence: MLVRGYVVSRKLFASILIGALLGIGAPPSAHA (SEQ ID NO:8)) is as follows:

(SEQ ID NO: 9)
MLVRGYVVSRKLFASILIGALLGIGAPPSAHAGADDVVDSSKSFVMENFS

SYHGTKPGYVDSIQKGIQKPKSGTQGNYDDDWKGFYSTDNKYDAAGYSVD

NENPLSGKAGGVVKVTYPGLTKVLALKVDNAETIKKELGLSLTEPLMEQV

GTEEFIKRFGDGASRVVLSLPFAEGSSSVEYINNWEQAKALSVELEINFE

TRGKRGQDAMYEYMAQACAGNRVRRSVGSSLSCINLDWDVIRDKTKTKIE

SLKEHGPIKNKMSESPNKTVSEEKAKQYLEEFHQTALEHPELSELKTVTG

TNPVFAGANYAAWAVNVAQVIDSETADNLEKTTAALSILPGIGSVMGIAD

GAVHHNTEEIVAQSIALSSLMVAQAIPLVGELVDIGFAAYNFVESIINLF

QVVHNSYNRPAYSPGHKTQPFLHDGYAVSWNTVEDSIIRTGFQGESGHDI

KITAENTPLPIAGVLLPTIPGKLDVNKSKTHISVNGRKIRMRCRAIDGDV

TFCRPKSPVYVGNGVHANLHVAFHRSSSEKIHSNEISSDSIGVLGYQKTV

DHTKVNSKLSLFFEIKS.

An exemplary amino acid sequence for a biologically active variant of a *Diphtheria* toxin, which contains amino acids 33-421 of SEQ ID NO:9 (i.e., it lacks the N-terminal leader sequence of SEQ ID NO:9) and an exogenous methionine at position 1, is as follows: MGADDVVDSSKS-FVMENFSSYHGTKPGYVDSIQKGIQKPKSGTQG-NYDDDWKGFYST DNKYDAAGYSVDNENPLSGKAG-GVVKVTYPGLTKVLALKVDNAETIKKELGLSLTEPL MEQVGTEEFIKRFGDGASRVVLSLPFAE-GSSSVEYINNWEQAKALSVELEINFETRGKRG QDA-MYEYMAQACAGNRVRRSVGSSLSCINLD-WDVIRDKTKTKIESLKEHGPIKNKMSE SPNKTVSEEKAKQYLEEFHQTALEH-PELSELKTVTGTNPVFAGANYAAWAVNVAQVID SET-ADNLEKTTAALSILPGIGSVMGIAD-GAVHHNTEEIVAQSIALSSLMVAQAIPLVGELV DIGFAAYNFVESIINLFQVVHNSYNRPAYSPGHKTQPF (SEQ ID NO:10). This amino acid sequence is also herein referred to as DT390.

In some embodiments the toxic polypeptide can consist of, or contain, a *Pseudomonas* exotoxin A or a biologically active fragment thereof.

An exemplary amino acid sequence for a full-length *Pseudomonas* exotoxin A is as follows:

```
                                        (SEQ ID NO: 11)
MHLIPHWIPLVASLGLLAGGSSASAAEEAFDLWNECAKACVLDLKDGVRS

SRMSVDPAIADTNGQGVLHYSMVLEGGNDALKLAIDNALSITSDGLTIRL

EGGVEPNKPVRYSYTRQARGSWSLNWLVPIGHEKPSNIKVFIHELNAGNQ

LSHMSPIYTIEMGDELLAKLARDATFFVRAHESNEMQPTLAISHAGVSVV

MAQTQPRREKRWSEWASGKVLCLLDPLDGVYNYLAQQRCNLDDTWEGKIY

RVLAGNPAKHDLDIKPTVISHRLHFPEGGSLAALTAHQACHLPLETFTRH

RQPRGWEQLEQCGYPVQRLVALYLAARLSWNQVDQVIRNALASPGSGGDL

GEAIREQPEQARLALTLAAAESEREVRQGTGNDEAGAANADVVSLTCPVA

AGECAGPADSGDALLERNYPTGAEFLGDGGDVSFSTRGTQNWTVERLLQA

HRQLEERGYVFVGYHGTFLEAAQSIVEGGVRARSQDLDAIWRGFYIAGDP

ALAYGYAQDQEPDARGRIRNGALLRVYVPRSSLPGFYRTSLTLAAPEAAG

EVERLIGHPLPLRLDAITGPEEEGGRLETILGWPLAERTVVIPSAIPTDP

RNVGGDLDPSSIPDKEQAISALPDYASQPGKPPREDLK.
```

An exemplary amino acid sequence for a biologically active variant of a *Pseudomonas* exotoxin A, which contains amino acids 276-633 of (SEQ ID NO:11) is as follows:

```
                                        (SEQ ID NO: 12)
PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANADVVSLTCPVAAGECAGPADSGDALLERNYPTGAEF

LGDGGDVSFSTRGTQNWTVERLLQAHRQLEERGYVFVGYHGTFLEAAQSI

VFGGVRARSQDLDAIWRGFYIAGDPALAYGYAQDQEPDARGRIRNGALLR

VYVPRSSLPGFYRTSLTLAAPEAAGEVERLIGHPLPLRLDAITGPEEEGG

RLETILGWPLAERTVVIPSAIPTDPRNVGGDLDPSSIPDKEQAISALPDY

ASQPGKPPKDEL.
```

The toxic polypeptide can consist of, or contain, *Pseudomonas* exotoxin (PE), bryodin, gelonin, α-sarcin, aspergillin, restrictocin, angiogenin, saporin, abrin, a prokaryotic ribonuclease, a eukaryotic ribonuclease, ricin, pokeweed antiviral protein (PAP), a pro-apoptotic polypeptide, a ribosomal inhibitory protein, or a biologically active fragment of any of the foregoing. Suitable pro-apoptotic polypeptides include, but are not limited to, Bax, Bad, Bak, Bim, Bik, Bok, Hrk, FasL, TRAIL, or TNF-α.

In some embodiments, a toxic domain can include, e.g., one or more (e.g., one, two, three, four, five, six, seven, or eight or more) of toxins (e.g., toxic small molecules, radionuclides, or toxic polypeptides or biologically active fragments thereof) such as any of those described herein. In addition, more than one (e.g. two, three, four, five, six, seven, eight, nine, or ten or more) toxin or biologically active fragment of one or more (e.g., one, two, three, four, five, six, seven, or eight or more) toxins can be included in a toxic domain. A toxic domain can include multiple copies or repeats of one or more toxins (e.g., two or more, three or more, four or more, five or more, six or more, seven or more, eight or more, nine or more, or ten or more copies of a toxin). Where repeats are included, they can be immediately adjacent to each other, separated by one or more targeting fragments, separated by a linker peptide (see below), separated by another, different, toxin.

The components (the domains, e.g., the first and second targeting domains and the toxic domain) of the receptor-targeting reagents described herein can be bound to each other by covalent or non-covalent bonds. For example, the components of the receptor-targeting reagents can be bound together by a first and second member of a binding pair. That is, the first targeting domain can be bound to a first member of a binding pair and the second targeting domain can be bound to a second member of a binding pair. The binding pair can be, e.g., avidin (or streptavidin) and biotin (or biocytin).

The components of the receptor-targeting reagents described herein can be bound together in a molecular complex in any of numerous configurations or conformations. For example, a first targeting domain (a), a second targeting domain (b), and a toxic domain (c) can be bound together as:
  (a) bound to (b) bound to (c);
  (c) bound to (a) bound to (b);
  (a) bound to (c) bound to (b);
  (c) bound to (b) bound to (a);
  (b) bound to (a) bound to (c);
  (b) bound to (c) bound to (a); or
  (a) bound to (b), (b) bound to (c), (c) bound to (a).

The domains can be bound together by any interaction described herein. It is understood that any of the domains of the receptor targeting reagents can be bound together by a mixture of covalent and non-covalent bonds. For example, the first and second targeting domains can be bound together by a first an second member of a binding pair and a toxic domain can be bound to the first or second targeting domain (or both) by a covalent bond.

Two or more (or all) of the domains of the receptor-targeting reagents can be covalently bound together as a fusion protein. For example, the first and second targeting domains, the first or second targeting domain and the toxic domain, or the first and second targeting domains and the toxic domain can be covalently bound together as a single fusion protein.

Any of the receptor-targeting reagents described herein can include one or more (e.g., two or more, three or more, four or more, five or more, six or more, or seven or more) linker moieties, which link one or more (or all) of the domains (e.g., the first targeting domain, the second targeting domain, or the toxic domain) of the receptor-targeting reagent together. Such linker moieties can be useful, e.g., in minimizing steric hindrance between two or more domains of a receptor-targeting reagent (e.g., minimizing steric hindrance between the first and second targeting domains) or in preventing the toxic domain (if present) from interfering with the ability of one or more targeting domains from binding to a target cell. Linker moieties can include, e.g., a first and second member of a binding pair or a peptide linker. Linker peptides can be one amino acid in length, but can be longer in length. For example, a linker peptide can be at least two (e.g., at least three, at least four, at least five, at least six, at least seven, at least eight, at least nine, at least 10, at least 11, at least 12, at least 13, at least 14, at least 15, at least 16, at least 17, at least 18, at least 19, at least 20, at least 25, at least 30, at least 35, at least 40, at least 45, at least 50, or at least 55 or more) amino acids long. Linker peptides can contain any amino acids.

In some embodiments, the peptide linker can consist of, or contain, part of the human muscle aldolase (hma) protein (e.g., PSGQAGAAASESLFVSNHAY (SEQ ID NO:13)). In some embodiments, one or more peptide linkers can contain, or consist of, EASGGPE (SEQ ID NO:14). In some embodiments, one or more peptide linkers can contain, or consist of, (i) an aggregation reducing linker (ARL) having the amino acid sequence GSTSGSGKPGSGEGSTKG (SEQ ID NO:4) and/or (ii) a mono or poly-GGGGS sequence (e.g., GGGGSGGGGSGGGGS (SEQ ID NO:5)). In embodiments where the receptor-targeting reagent is a fusion protein, the one or more linker moieties can link two or more of the domains of the fusion protein. Exemplary linker moieties and their roles in linking two or more domains of a receptor-targeting reagent are described in the accompanying Examples.

Exemplary receptor-targeting reagents are described in the accompanying Examples and include, e.g., the DTEGF13 receptor-targeting reagent comprising: a biologically active variant of *Diphtheria* toxin (SEQ ID NO:10), a linker (SEQ ID NO:14), an epidermal growth factor (SEQ ID NO:6), a linker (SEQ ID NO:13), and an IL13 (SEQ ID NO:7), and with the following amino acid sequence:

(SEQ ID NO: 1)
MGADDVVDSSKSFVMENFSSYHGTKPGYVDSIQKGIQKPKSGTQGNYDDD

WKGFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRSVGSSL

SCINLDWDVIRDKTKTKIESLKEHGPIKNKMSESPNKTVSEEKAKQYLEE

FHQTALEHPELSELKTVTGTNPVFAGANYAAWAVNVAQVIDSETADNLEK

TTAALSILPGIGSVMGIADGAVHHNTEEIVAQSIALSSLMVAQAIPLVGE

LVDIGFAAYNFVESIINLFQVVHNSYNRPAYSPGHKTQPFEASGGPENSD

SECPLSHDGYCLHDGVCMYIEALDKYACNCVVGYIGERCQYRDLKWWELR

PSGQAGAAASESLFVSNHAYGPVPPSTALRELIEELVNITQNQKAPLCNG

SMVWSINLTAGMYCAALESLINVSGCSAIEKTQRMLSGFCPHKVSAGQFS

SLHVRDTKIEVAQFVKDLLLHLKKLFREGRFN;

the EGF13 receptor-targeting reagent comprising: an epidermal growth factor (SEQ ID NO:6), a linker (SEQ ID NO:13), and an IL13 (SEQ ID NO:7), and having the following amino acid sequence:

(SEQ ID NO: 2)
NSDSECPLSHDGYCLHDGVCMYIEALDKYACNCVVGYIGERCQYRDLKWW

ELRPSGQAGAAASESLFVSNHAYGPVPPSTALRELIEELVNITQNQKAPL

CNGSMVWSINLTAGMYCAALESLINVSGCSAIEKTQRMLSGFCPHKVSAG

QFSSLHVRDTKIEVAQFVKDLLLHLKKLFREGRFN;

the EGF13 KDEL receptor-targeting reagent comprising: an epidermal growth factor (SEQ ID NO:6), a linker (SEQ ID NO:13), an IL13 (SEQ ID NO:7), a linker (SEQ ID NO:14), a biologically active fragment of *Pseudomonas* toxin A (SEQ ID NO:12), and a KDEL (SEQ ID NO:15), and having the following amino acid sequence:

(SEQ ID NO: 3)
MENSDSECPLSHDGYCLHDGVCMYIEALDKYACNCVVGYIGERCQYRDLK

WWELRPSGQAGAAASESLFVSNHAYGPVPPSTALRELIEELVNITQNQKA

PLCNGSMVWSINLTAGMYCAALESLINVSGCSAIEKTQRMLSGFCPHKVS

AGQFSSLHVRDTKIEVAQFVKDLLLHLKKLFREGRFNEASGGPEPEGGSL

AALTAHQACHLPLETFTRHRQPRGWEQLEQCGYPVQRLVALYLAARLSWN

QVDQVIRNALASPGSGGDLGEAIREQPEQARLALTLAAAESERFVRQGTG

NDEAGAANADVVSLTCPVAAGECAGPADSGDALLERNYPTGAEFLGDGGD

VSFSTRGTQNWTVERLLQAHRQLEERGYVFVGYHGTFLEAAQSIVFGGVR

ARSQDLDAIWRGFYIAGDPALAYGYAQDQEPDARGRIRNGALLRVYVPRS

SLPGFYRTSLTLAAPEAAGEVERLIGHPLPLRLDAITGPEEEGGRLETIL

GWPLAERTVVIPSAIPTDPRNVGGDLDPSSIPDKEQAISALPDYASQPGK

PPKDEL.;

the DTEGF4 receptor-targeting reagent comprising: a biologically active fragment of *Diphtheria* toxin (SEQ ID NO:10), a linker (SEQ ID NO:14), an epidermal growth factor (SEQ ID NO:6), a linker (SEQ ID NO:13), and an IL4 (SEQ ID NO:17), and having the following amino acid sequence:

(SEQ ID NO: 18)
MGADDVVDSSKSFVMENFSSYHGTKPGYVDSIQKGIQKPKSGTQGNYDDD

WKGFYSTDNKYDAAGYSVDNENPLSGKAGGVVKVTYPGLTKVLALKVDNA

ETIKKELGLSLTEPLMEQVGTEEFIKRFGDGASRVVLSLPFAEGSSSVEY

INNWEQAKALSVELEINFETRGKRGQDAMYEYMAQACAGNRVRRSVGSSL

SCINLDWDVIRDKTKTKIESLKEHGPIKNKMSESPNKTVSEEKAKQYLEE

FHQTALEHPELSELKTVTGTNPVFAGANYAAWAVNVAQVIDSETADNLEK

TTAALSILPGIGSVMGIADGAVHHNTEEIVAQSIALSSLMVAQAIPLVGE

LVDIGFAAYNFVESIINLFQVVHNSYNRPAYSPGHKTQPFEASGGPENSD

SECPLSHDGYCLHDGVCMYIEALDKYACNCVVGYIGERCQYRDLKWWELR

PSGQAGAAASESLFVSNHAYMGLTSQLLPPLFFLLACAGNFVHGHKCDIT

LQEIIKTLNSLTEQKTLCTELTVTDIFAASKNTTEKETFCRAATVLRQFY

SHHEKDTRCLGATAQQFHRHKQLIRFLKRLDRNLWGLAGLNSCPVKEANQ

STLENFLERLKTIMREKYSKCSS;

the EGF4 KDEL receptor-targeting reagent comprising: a biologically active fragment of an epidermal growth factor (SEQ ID NO:6), a linker (SEQ ID NO:13), an IL4 (SEQ ID NO:17), a linker (SEQ ID NO:14), a biologically active fragment of *Pseudomonas* toxin A (SEQ ID NO:12), and a KDEL (SEQ ID NO:15), and having the following amino acid sequence:

(SEQ ID NO: 19)
MNSDSECPLSHDGYCLHDGVCMYIEALDKYACNCVVGYIGERCQYRDLKW

WELRPSGQAGAAASESLFVSNHAYMGLTSQLLPPLFFLLACAGNFVHGHK

CDITLQEIIKTLNSLTEQKTLCTELTVTDIFAASKNTTEKETFCRAATVL

RQFYSHHEKDTRCLGATAQQFHRHKQLIRFLKRLDRNLWGLAGLNSCPVK

EANQSTLENFLERLKTIMREKYSKCSSEASGGPEPEGGSLAALTAHQACH

LPLETFTRHRQPRGWEQLEQCGYPVQRLVALYLAARLSWNQVDQVIRNAL

ASPGSGGDLGEAIREQPEQARLALTLAAAESEREVRQGTGNDEAGAANAD

-continued
VVSLTCPVAAGECAGPADSGDALLERNYPTGAEFLGDGGDVSFSTRGTQN

WTVERLLQAHRQLEERGYVFVGYHGTFLEAAQSIVFGGVRARSQDLDAIW

RGFYIAGDPALAYGYAQDQEPDARGRIRNGALLRVYVPRSSLPGFYRTSL

TLAAPEAAGEVERLIGHPLPLRLDAITGPEEEGGRLETILGWPLAERTVV

IPSAIPTDPRNVGGDLDPSSIPDKEQAISALPDYASQPGKPPKDEL;
and the EGF4 receptor-targeting reagent comprising: an epidermal growth factor (SEQ ID NO:6), a linker (SEQ ID NO:13), and an IL4 (SEQ ID NO:17), and having the following amino acid sequence:

(SEQ ID NO: 20)
NSDSECPLSHDGYCLHDGVCMYIEALDKYACNCVVGYIGERCQYRDLKWW

ELR<u>PSGQAGAAASESLFVSNHAY</u>MGLTSQLLPPLFFLLACAGNFVHGHKC

DITLQEIIKTLNSLTEQKTLCTELTVTDIFAASKNTTEKETFCRAATVLR

QFYSHHEKDTRCLGATAQQFHRHKQLIRFLKRLDRNLWGLAGLNSCPVKE

ANQSTLENFLERLKTIMREKYSKCSS.

The linker regions of each of the above exemplary receptor-targeting reagents are underlined.

Any of the receptor-targeting reagents described herein can also include one or more (e.g., two or more, three or more, four or more, five or more, six or more, seven or more, eight or more, nine or more, or 10 or more) detectable labels. For example, a receptor-targeting reagent can include an enzyme (e.g., horseradish peroxidase, alkaline phosphatase, β-galactosidase, or acetylcholinesterase), a fluorescent material (e.g., umbelliferone, fluorescein, fluorescein isothiocyanate, rhodamine, dichlorotriazinylamine fluorescein, dansyl chloride, allophycocyanin (APC), or phycoerythrin), a luminescent material (e.g., europium, terbium), a bioluminescent material (e.g., luciferase, luciferin, or aequorin), or a radionuclide (e.g., any of the radionuclides described herein).

It is understood that any of the receptor-targeting reagents described herein can contain one or more (e.g., one, two, three, four, five, six, seven, eight, nine, or 10 or more) additional "targeting" domains and/or one or more (e.g., one, two, three, four, five, six, seven, eight, nine, or 10 or more) additional toxic domains. The receptor-targeting reagents can contain one or more of a first targeting domain, one or more of a second targeting domain, and/or one or more of a toxic domain. For example, a receptor-targeting reagent described herein can contain two or more EGFR-binding domains and/or two or more IL13R- or IL4R-binding domains.

The various domains (e.g., the first targeting domain, the second targeting domain, or the toxic domain) of the receptor-targeting reagents can be arranged in any orientation with respect to each other. For example, a toxic domain can be N-terminal or C-terminal to one or more (or all) targeting domains. In another example, the toxic domain can be between two targeting domains. Likewise, the targeting domains can be adjacent to each other or separated by, e.g., a toxic domain and/or a linker moiety (see above).

In some embodiments, any polypeptide described herein (e.g., a toxic polypeptide) can be modified in such a way as to reduce or prevent immunogenicity of the polypeptide in a subject. As used herein, a polypeptide modified to have a "reduced immunogenicity" is one that elicits less of an immune response in a given subject, or cohort of subjects, than the corresponding unmodified polypeptide. As exemplified in the working Examples, a nucleic acid encoding a polypeptide can be modified through standard molecular biology techniques (Sambrook et al., supra) such that the encoded polypeptide contains one or more substitutions effective to reduce the immunogenicity of the polypeptide in a subject.

A modified polypeptide can contain at least two (e.g., three, four, five, six, seven, eight, nine, 10, 11, 12, 13, 14, 15, 16, 17, 18, 19, 20, 21, 22, 23, 24, 25, 30, 32, 35, or 40 or more) amino acid substitutions. A modified polypeptide can contain less than 20 (e.g., 19, 18, 17, 16, 15, 14, 13, 12, 11, 10, nine, eight, seven, six, five, four, three, two, or one) amino acid substitutions. It is understood that a modified polypeptide can contain at least two, but less than 20 amino acid substitutions.

Suitable in vitro and in vivo methods for determining the immunogenicity of a polypeptide are known in the art and described in the working Examples. In vitro methods include, e.g., culturing lymphoid cells (including T and B lymphocytes) obtained from a mammalian subject with a polypeptide (e.g., modified or unmodified) described herein. The lymphoid cells can be from a subject pre-exposed to the polypeptide, to the protein from which the polypeptide was derived, or where the polypeptide is derived from a microorganism, to the microorganism that naturally produces the polypeptide. Alternatively, the donor of the lymphoid cells need not have been exposed to any of these entities. The cultures can be "restimulated" as often as necessary with either the polypeptide. The cultures can also be monitored at various times to ascertain what time of immune reactivity (e.g., antibody production or CD4+ helper T cell activity) has occurred. In such experiments, one set of cells would be contacted with a modified polypeptide and a identical second set of cells would be contacted with the corresponding unmodified polypeptide. A decrease in the immune response generated by the modified polypeptide as compared to the immune response generated by the unmodified polypeptide is an indication that the modified polypeptide has reduced immunogenicity.

In in vivo methods, the polypeptide itself can be administered to a subject. The polypeptides can be administered to a subject orally, transdermally, intrarectally, intravaginally, intranasally, intragastrically, intratracheally, or intrapulmonarily, or injected (or infused) intravenously, subcutaneously, intramuscularly, or intraperitoneally. The polypeptide can be delivered directly to an appropriate lymphoid tissue (e.g. spleen, lymph node, or mucosal-associated lymphoid tissue (MALT)). In studies where human subjects are used, a polypeptide can be administered subcutaneously and the occurrence, or severity, of a "wheel and flare" can be an indicate the immunogenicity of a polypeptide to that subject. In some embodiments, a modified polypeptide and the unmodified polypeptide can be administered to the same subject, e.g., using skin tests. Such assays test for both antibodies and pre-activated CD4+ T cells specific for the test antigen. A positive response within 12 hours is indicative of an antibody response, while a response that is optimal between 48 and 96 hours indicates the presence of CD4+ T cells that have previously been exposed to the relevant antigen. For example, a human subject can be administered subcutaneously a modified and an unmodified composition to different positions within the same region of the body, e.g., to different positions on the subject's back or abdomen. In some embodiments, such as animal experiments, one animal or group of animals (e.g., mice) can be administered the modified polypeptide and an identical animal or group of animals can be administered the corresponding unmodified polypeptide. As in the in vitro experiments, a decrease in the immune response generated by the modified polypeptide as compared to the immune response generated by the unmodified polypeptide is an indication that the modified polypeptide has reduced immunogenicity.

Methods for measuring the level of an immune response are known in the art, set forth in the detailed description, and exemplified in the working Examples. For example, methods for determining antibody production are described in the section entitled "Methods for Generating Antibodies."

Nucleic Acids and Methods of Making the Receptor-Targeting Reagents.

Also featured are nucleic acids encoding the polypeptide receptor-targeting reagents (e.g., full length polypeptide receptor-targeting reagents or polypeptide domains thereof) described herein and vectors containing the nucleic acids. The nucleic acids and vectors can be used, e.g., to express the polypeptide receptor-targeting reagents in a host cell (e.g., a bacterial, yeast, or mammalian cell). The nucleic acids and vectors can also be used in, e.g., ex vivo methods of treatment as described below.

A single nucleic acid can encode an entire receptor-targeting reagent, e.g., a receptor-targeting reagent fusion protein. A receptor-targeting reagent can be, in some instances, encoded by two or more (e.g., three or more, four or more, five or more, six or more, seven or more, eight or more, nine or more, or ten or more) different nucleic acids. For example, each domain of a receptor-targeting reagent can be encoded by a separate nucleic acid.

In some embodiments, the nucleic acids can be operably-linked to promoter and/or enhancer elements that direct the expression of the polypeptide receptor-targeting reagents encoded by the nucleic acids. The coding sequence for a given polypeptide receptor-targeting reagent can be contained within a single expression vector containing a nucleic acid sequence (e.g., a genomic DNA sequence or a cDNA sequence) or can be contained in two or more vectors. For example, a polypeptide receptor-targeting reagent containing three different domains (e.g., a first targeting domain, a second targeting domain, and a toxic domain) can be encoded by different nucleic acids that are present in three different vectors, where each vector contains, e.g., the coding sequence of one domain. In the latter case, the domains encoded within the respective vectors can be designed such that they associate post-translationally within the cell in which they are produced either by covalent (e.g., disulfide) bonds or non-covalent (e.g., hydrophobic or ionic) interactions. Alternatively, each of the separate domains can be isolated first and then bound together (e.g., chemically or enzymatically bound together) in a separate step.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3 phosphoglycerate kinase, the promoters of acid phosphatase, and the promoters of the yeast a mating factors, the adenoviral E1b minimal promoter, or the thymidine kinase minimal promoter.

Where a single fusion protein is encoded, the nucleic acid sequence encoding the targeting domains can be 5' of a nucleic acid encoding the toxic domain or vice versa. The two coding sequences will be in frame with each other and can be immediately adjacent to each other or separated by a linker region encoding a linker peptide which can serve, for example, to prevent steric hindrance by the toxic domain of binding of the first or second targeting domains to the surface of the target cell.

In some embodiments, the nucleic acids, or vectors containing the nucleic acids, can contain a leader sequence that encodes a signal peptide. The leader sequence can be at the 5' end of the sequence encoding, e.g., one or more of the domains of a receptor-targeting reagent or a fusion protein of the entire receptor-targeting reagent. The signal peptide can be immediately N-terminal of a mature polypeptide (e.g., a mature form of a first or second targeting domain or a fusion protein encoding the receptor-targeting reagent) but can be separated from it by one or more (e.g., 2, 3, 4, 6, 8, 10, 15 or 20) amino acids, provided that the leader sequence is in frame with the nucleic acid sequence encoding the fusion protein. The signal peptide, which is generally cleaved from the fusion protein prior to secretion, directs fusion proteins into the lumen of the targeting cell endoplasmic reticulum (ER) during translation and the fusion proteins are then secreted, via secretory vesicles, into the environment of the targeting cell. In this way, the targeting cells remain viable since interaction of the toxin with the protein synthetic machinery in the cytosol of the targeting cell is prevented by the membrane bilayers of the ER and secretory vesicles. Useful leader peptides can be the native leader peptide of the relevant targeting domain (of an IL-4, an EGF, or an IL13 or IL16 polypeptide) or a functional fragment of the native leader. Alternatively, the leader can be derived from another polypeptide. For example, the signal peptide can have the amino acid sequence MAISGVPVLGFFIIAVLMSAQESWA (SEQ ID NO:16). In addition, the peptide sequence KDEL (SEQ ID NO:15) has been shown to act as a retention signal for the ER. In some embodiments a signal polypeptide can be at the 3' end of nucleic acid encoding a polypeptide (that is, the carboxy-terminus of a protein encoded by the nucleic acid). For example, a KDEL (SEQ ID NO:15) sequence can be at the 3' end of a nucleic acid encoding a receptor-targeting reagent such as the EGF13 KDEL reagent described in the accompanying Examples. Other signal sequences are described in detail in U.S. Pat. No. 5,827,516, the disclosure of which is incorporated herein by reference in its entirety.

In some embodiments, the 5' end of a nucleic acid encoding a polypeptide receptor-targeting reagent (e.g., a fusion protein receptor-targeting reagent) or any of the polypeptide targeting domains, polypeptide toxic domains (or toxic polypeptides therein), can include a non-native ATG "start sequence." That is an ATG sequence can be added to, e.g., a nucleic acid encoding a biologically active fragment or variant of a full-length polypeptide to ensure that the protein is properly transcribed and translated. Although a leader sequence generally includes an ATG start sequence, in embodiments where it does not, the ATG sequence can be added at the 5' end of a nucleic acid encoding the leader sequence. Naturally, this will result in a non-native methionine residue amino acid in the corresponding sequence of a polypeptide receptor-targeting reagent.

Suitable methods for constructing nucleic acids and expression vectors are well known to those skilled in the art and described in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; the disclosure of which is incorporated herein by reference in its entirety.

A recombinant nucleic acid can be introduced into a cell using a variety of methods, which methods can depend, at least in part, on the type of cell into which the nucleic acid is introduced. For example, bacterial cells can be transformed using methods such as electroporation or heat shock. Methods for transfecting yeast cells include, e.g., the spheroplast technique or the whole-cell lithium chloride yeast transformation method (see, e.g., U.S. Pat. No. 4,929,555; Hinnen et al. (1978) Proc. Nat. Acad. Sci. USA 75:1929; Ito et al. (1983) J. Bacteriol. 153:163; U.S. Pat. No. 4,879,231; and Sreekrishna et al. (1987) Gene 59:115, the disclosures of each of which are incorporated herein by reference in their entirety). Transfection of animal cells can feature, for example, the introduction of a vector to the cells using calcium phosphate, electroporation, heat shock, liposomes, or transfection reagents such as FUGENE® or LIPO-FECTAMINE®, or by contacting naked nucleic acid vectors with the cells in solution (see, e.g., Sambrook et al., supra).

Expression systems that may be used for small or large scale production of the receptor-targeting reagents described herein include, but are not limited to, microorganisms such as bacteria (for example, E. coli and B. subtilis) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention; insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing fusion protein nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter, a CMV promoter, an SV40 promoter, or the vaccinia virus 7.5K promoter). Also useful as host cells are primary or secondary cells obtained directly from a mammal, transfected with a plasmid vector or infected with a viral vector (e.g., viral vectors such as herpes viruses, retroviruses, vaccinia viruses, attenuated vaccinia viruses, canary pox viruses, adenoviruses and adeno-associated viruses, among others; see Ex Vivo Methods below).

Following the expression of any of the receptor-targeting reagents described herein, the receptor-targeting reagents can be isolated from the cultured cells, or from the media in which the cells were cultured, using standard techniques (see Sambrook et al., supra). Methods of isolating proteins are known in the art and include, e.g., liquid chromatography (e.g., HPLC), affinity chromatography (e.g., metal chelation or immunoaffinity chromatography), ion-exchange chromatography, hydrophobic-interaction chromatography, precipitation, or differential solubilization.

Smaller receptor-targeting reagents (or domains thereof), e.g., receptor-targeting reagents or domains having less than 200 (e.g., less than 175, less than 150, less than 125, less than 100, less than 90, less than 80, less than 70, or less than 60) amino acids can be chemically synthesized by standard chemical means.

In some embodiments, the isolated receptor-targeting reagents can be frozen, lyophilized, or immobilized and stored under appropriate conditions, which allow the proteins to retain activity (e.g., immunotoxic activity or the ability to bind to a cell).

Where one or more domains or agents (e.g., a targeting domain or toxic agent) have been produced independently, each domain or agent can be linked to together by covalent or non-covalent bonds using methods known in the art. For example, a terminal or internal cysteine residue on one domain (or agent) can be utilized to form a disulfide bond with a terminal or internal cysteine residue on another domain or agent.

Domains or agents can also be cross-linked using any of a number of known chemical cross linkers. Examples of such chemical cross-linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable chemical cross-linker, 4-succinimidyloxycarbonyl-α-methyl-α(2-pyridyldithio)toluene (SMPT), forms such a linkage between two domains (or agents) utilizing a terminal lysine on one of the domains (or agents) and a terminal cysteine on the other. Heterobifunctional reagents which cross-link by a different coupling moiety on each domain (e.g., each domain polypeptide) or agent (e.g., a toxic small molecule or radionuclide). Thus, the coupling moiety on one domain or agent could be a cysteine residue and on the other a lysine residue. In this way, the resulting dimers will be heterodimers rather than either homodimers or a mixture of homodimers and heterodimers. Other useful cross-linkers include, without limitation, chemicals that link two amino groups (e.g., N-5-Azido-2-nitrobenzoyloxysuccinimide), two sulfhydryl groups (e.g., 1,4-Bis-maleimidobutane) an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanadium group that is present in the side chain of arginine (e.g., p-azidophenyl glyoxal monohydrate).

While these cross-linking methods can involve residues ("coupling moieties") that are native to any of the domains or agents, they can also be used to cross-link non-native ("heterologous") sequences (e.g., linker sequences) incorporated into the polypeptide chains. While not necessarily the case, such sequences will generally be composed of amino acids (e.g., cysteine, lysine, arginine, or any N-terminal amino acid). Non-amino acid moieties include, without limitation, carbohydrates (e.g., on glycoproteins) in which, for example, vicinal diols are employed (Chamow et al. (1992) J. Biol. Chem. 267, 15916-15922). The cross-linking agent 4-(4-N-maleimidophenyl)butyric acid hydrazide (MPBH), for example, can be used to cross-link a carbohydrate residue on one domain (or agent) and a sulfhydryl group on another. They can be added during, for example, chemical synthesis of a domain (or agent) or a part of the domain or agent. Alternatively, they can be added by standard recombinant nucleic acid techniques known in the art.

The heterologous coupling moieties can be positioned anywhere in a domain or agent of a fusion protein, provided that the activity of the resulting receptor-targeting reagent is not compromised. Thus, the linkage must not result in disruption of the structure of a targeting domain such that it is substantially unable to bind to the cell-surface molecule for which it is specific. Furthermore, the linkage must not result in the disruption of the structure of the toxic domain (or agent) such that it is substantially unable to inhibit the proliferation of (or kill) its respective target cell. Using standard binding and toxicity assays known to those in the art (and detailed in the accompanying Examples), candidate receptor-targeting reagents employing linkages involving different residues on the domains can be tested for their ability to bind and inhibit the proliferation of (or kill) target cells of interest. Using molecular modeling techniques, it will frequently be possible to predict regions on a targeting domain or toxic domain (or agents) that would be appropriate for the insertion of moieties by which inter-domain linkages could be formed. Thus, for example, regions predicted to be on the exterior surface of a targeting domain, but unlikely to be involved in binding to a target molecule, could be useful regions in which to an insert an appropriate moiety in the targeting domain. Similarly, regions predicted to be on exterior surface of a toxic domain (or agent), but unlikely to be involved in the toxic activity, could be useful regions in which to an insert an appropriate moiety in the toxic domain.

The coupling moieties will preferably be at the termini (C or N) of the domains. They can be, as indicated above, a cysteine residue on each domain (or agent), or a cysteine on one and a lysine on the other. Where they are two cysteine residues, cross-linking can be effected by, for example, exposing the domains (or agents) to oxidizing conditions.

It can be desirable in some cases to eliminate, for example, one or more native cysteine residues in a domain or agent in order to restrict cross-linking to only non-native moieties inserted into the domains or agents. A potentially troublesome cysteine could, for example, be replaced by an alanine or a tyrosine residue. This can be done by, for example, standard recombinant techniques. Naturally, these replacements should not compromise the activity of the resulting receptor-targeting reagent.

Where more than two domains (or more than two agents) are to be joined, at least one of the domains (or agents) can have more than one cross-linking moiety. Such multimers can be constructed "sequentially," such that each domain or agent is joined to the next such that the terminal two domains (or agents) in the chain only have one residue involved in an inter-domain (or inter-agent) bond while the "internal" domains (or agents) each have two moieties involved in inter-domain bonds. Alternatively, one domain could be linked to multiple (e.g., 2, 3, 4, or 5) other domains or agents.

Additional Processing of Receptor-Targeting Reagents.

Following the expression or synthesis of any of the polypeptide receptor-targeting reagents described herein, the reagents can be further processed. For example, the further processing can include chemical or enzymatic additions of one or more domains to the receptor-targeting reagent or modifications to existing domains present in the receptor-targeting domain or both. The additional processing of the receptor-targeting molecule can include the addition (covalent or non-covalent joining) of a heterologous amino acid sequence such as a polymer, a carrier, or any of the other heterologous sequences described above. The processing can include the additional of, e.g., a radionuclide to the receptor-targeting reagent. The radionuclide can be toxic (as described above) or generally non-toxic or of low toxicity such as radionuclides used in in vivo diagnostics. Examples of diagnostic-type radionuclides include, but are not limited to, $^{186}$Re, $^{188}$Re, $^{64}$Cu, $^{67}$Cu, $^{212}$Bi, $^{123}$I, $^{131}$I, $^{211}$At, $^{177}$Lu, $^{47}$Sc, $^{105}$Rh, $^{109}$Pd, $^{153}$Sm, $^{199}$Au, $^{99m}$Tc, $^{111}$In, $^{124}$I, $^{18}$F, $^{11}$C, $^{198}$Au, $^{75}$Br, $^{76}$Br, $^{77}$Br, $^{13}$N, $^{34m}$Cl, $^{52m}$Mn, $^{55}$Co, $^{62}$Cu, $^{68}$Ga, $^{72}$As, $^{76}$As, $^{72}$Se, $^{73}$Se, or $^{75}$Se. Methods of attaching the radionuclide atoms (or larger molecules/chelates containing them; see above) to a receptor-targeting reagent are known in the art and can involve incubating the receptor-targeting reagent with the radionuclide under conditions (e.g., pH, salt concentration, and/or temperature) which facilitate binding of the radionuclide atom or radionuclide atom-containing molecule or chelate to the receptor-targeting reagent (see, e.g., U.S. Pat. No. 6,001,329, the disclosure of which is incorporated herein by reference in its entirety).

The further processing can also involve enzymatic or chemical treatment of the receptor-targeting reagent. For example, enzymatic treatment can involve contacting the altered target molecule with, e.g., one or more proteases, phosphatases, or kinases for a time sufficient to induce modification of the receptor-targeting reagent. Enzymatic treatment can involve contacting the receptor-targeting reagent with one or more enzymes (e.g., an oligosaccharyltransferase or a mannosidase) capable of glycosylating, or modifying the glycosylation of, the receptor-targeting reagents.

Pharmaceutical Compositions Containing Receptor-Targeting Reagents.

Any of the receptor-targeting reagents described herein can be incorporated into pharmaceutical compositions. Such compositions typically include the receptor-targeting reagent and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. A receptor-targeting reagent can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc. Supplementary active compounds (e.g., one or more chemotherapeutic agents) can also be incorporated into the compositions.

A pharmaceutical composition is generally formulated to be compatible with its intended route of administration. Examples of routes of administration include oral, rectal, and parenteral, e.g., intravenous, intramuscular, intradermal, subcutaneous, inhalation, transdermal, or transmucosal. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contamination by microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of contamination by microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be facilitated by including in the composition an agent that delays absorption, for example, aluminum monostearate and gelatin.

Sterile injectable solutions can be prepared by incorporating the receptor-targeting reagents in the required amount in an appropriate solvent with one or a combination of ingredients enumerated above, as required, followed by filtered sterilization. Generally, dispersions are prepared by incorporating the receptor-targeting reagent into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the receptor-targeting reagent can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The powders and tablets can contain from 1% to 95% (w/w) of the receptor-targeting reagent. In certain embodiments, the receptor-targeting reagent ranges from 5% to 70% (w/w). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the receptor-targeting reagent with encapsulating material as a carrier providing a capsule in which the receptor-targeting reagent with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

For administration by inhalation, the compounds are delivered in the form of an aerosol spray from pressured container or dispenser which contains a suitable propellant, e.g., a gas such as carbon dioxide, or a nebulizer.

A receptor-targeting reagent suitable for topical administration can be formulated as, e.g., a cream, a spray, a foam, a gel, an ointment, a salve, or a dry rub. A dry rub can be rehydrated at the site of administration. A receptor-targeting reagent can also be formulated for direct infusion into (e.g., soaked into and dried) a bandage, gauze, or patch for topical administration. The receptor-targeting reagents can also be formulated in a semi-liquid, gelled, or fully-liquid state in a bandage, gauze, or patch for topical administration (see, e.g., U.S. Pat. No. 4,307,717, the content of which is incorporated herein by reference in its entirety).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the receptor-targeting reagents are formulated into ointments, salves, gels, or creams as generally known in the art.

The receptor-targeting reagents can also be prepared in the form of suppositories (e.g., with conventional suppository bases such as cocoa butter and other glycerides) or retention enemas for rectal delivery.

In one embodiment, the receptor-targeting reagents are prepared with carriers that will protect the receptor-targeting reagent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form, as used herein, refers to physically discrete units suited as unitary dosages for the subject to be treated, each unit containing a predetermined quantity of receptor-targeting reagent calculated to produce the desired therapeutic effect in association with the required pharmaceutical carrier. Dosage units can also be accompanied by instructions for use.

Any of the pharmaceutical compositions described herein can be included in a container, pack, or dispenser together with instructions for administration as described in the following section.

Methods for Generating Antibodies

Methods of making an antibody specific for an EGFR (e.g., HER1, HER2, HER3, or HER4), IL13R, or IL4R described herein are known in the art. For example, methods for generating antibodies or antibody fragments specific for a protein encoded by one or more genes can be generated by immunization, e.g., using an animal, or by in vitro methods such as phage display. A polypeptide that includes all or part of a target protein (e.g., all or part of an EGFR, an IL13R, or an IL4R) can be used to generate an antibody or antibody fragment.

A peptide can be used to prepare antibodies by immunizing a suitable subject, (e.g., rabbit, goat, mouse, or other mammal) with the peptide. An appropriate immunogenic preparation can contain, for example, a chemically synthesized peptide or a recombinantly expressed peptide. The preparation can further include an adjuvant, such as Freund's complete or incomplete adjuvant, or similar immunostimulatory agent. Immunization of a suitable subject with an immunogenic peptide preparation induces a polyclonal anti-peptide antibody response.

The term antibody as used herein refers to immunoglobulin molecules and immunologically active portions of immunoglobulin molecules (i.e., molecules that contain an antigen binding site that specifically bind to the peptide). An antibody that specifically binds to a peptide described herein is an antibody that binds the peptide, but does not substantially bind other molecules in a sample. Examples of immunologically active portions of immunoglobulin molecules include F(ab) and F(ab')$_2$ fragments.

The anti-peptide antibody can be a monoclonal antibody or a preparation of polyclonal antibodies. The term monoclonal antibody, as used herein, refers to a population of antibody molecules that contain only one species of an antigen binding site capable of immunoreacting with the peptide. A monoclonal antibody composition thus typically displays a single binding affinity for a particular peptide with which it immunoreacts.

Polyclonal anti-peptide antibodies can be prepared as described above by immunizing a suitable subject with a peptide immunogen. The anti-peptide antibody titer in the immunized subject can be monitored over time by standard techniques, such as with an enzyme linked immunosorbent assay (ELISA) using immobilized peptide. If desired, the antibody molecules directed against the peptide can be isolated from the mammal (e.g., from the blood) and further purified by techniques such as protein A chromatography to obtain the IgG fraction. At an appropriate time after immunization, e.g., when the anti-peptide antibody titers are highest, antibody-producing cells can be obtained from the subject and used to prepare monoclonal antibodies by standard techniques, such as the hybridoma technique originally described by Kohler and Milstein (1975) Nature 256:495-497, the human B cell hybridoma technique (Kozbor et al. (1983) Immunol. Today 4:72), or the EBV-hybridoma technique (Cole et al. (1985), Monoclonal Antibodies and Cancer Therapy, Alan R. Liss, Inc., pp. 77-96). Any of the many well known protocols used for fusing lymphocytes and immortalized cell lines can be applied for the purpose of generating an anti-peptide monoclonal antibody (see, e.g., Current Protocols in Immunology, supra; Galfre et al. (1977) Nature 266: 55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402).

As an alternative to preparing monoclonal antibody-secreting hybridomas, a monoclonal anti-peptide antibody can be identified and isolated by screening a recombinant combinatorial immunoglobulin library (e.g., an antibody phage display library) with a peptide described herein to isolate immunoglobulin library members that bind the peptide.

An anti-peptide antibody (e.g., a monoclonal antibody) can be used to isolate the peptide by techniques such as affinity chromatography or immunoprecipitation. Moreover, an anti-peptide antibody can be used to detect the peptide in screening assays described herein. An antibody can optionally be coupled to a detectable label such as any of those described herein or a first or second member of a binding pair (e.g., streptavidin/biotin or avidin/biotin), the second member of which can be conjugated to a detectable label.

Non-human antibodies to an EGFR, an IL13R, or an IL4R can also be produced in non-human host (e.g., a rodent) and then humanized, e.g., as described in U.S. Pat. No. 6,602,503, EP 239 400, U.S. Pat. No. 5,693,761, and U.S. Pat. No. 6,407,213.

EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al., 1988, Nature 332, 323-327; Verhoeyen et al., 1988, Science 239, 1534-1536. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (e.g., at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213, the disclosure of which is incorporated herein by reference in its entirety.

Fully human monoclonal antibodies that bind to an EGFR, an IL13R, or an IL4R can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798,230, the disclosures of each of which are incorporated herein by reference in their entirety. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with an EGFR, an IL13R, or an IL4R.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762, the disclosures of each of which are incorporated herein by reference in their entirety. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 kDa or 214 amino acids) are encoded by a variable region gene at the NH2-terminus (about 110 amino acids) and a kappa or lambda constant region gene at the COOH-terminus. Full-length immunoglobulin "heavy chains" (about 50 kDa or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest (i.e., an EGFR, an IL13R, or an IL4R). Examples of binding fragments encompassed within the term "antigen-binding fragment" of a full length antibody include: (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scF$_v$). See e.g., Bird et al. (1988) Science 242:423-426; and Huston et al. (1988) Proc. Natl. Acad. Sci. USA 85:5879-5883, the disclosures of each of which are incorporated herein by reference in their entirety.

Methods for Binding a Receptor-Targeting Reagent to a Cell

The present disclosure provides a variety of in vitro, in vivo, and ex vivo methods for binding a receptor-targeting reagent to a cell. Where the receptor-targeting reagent is immunotoxic (i.e., the receptor-targeting reagent contains one or more toxic domains), the methods can be used to inhibit the proliferation of (or kill) a cell (e.g., a cancer cell or an immune cell mediating an inflammatory disorder). In embodiments where the receptor-targeting reagents are detectably labeled, such reagents can be useful for detecting the presence of a cell (e.g., a cancer cell or an immune cell mediating an inflammatory disorder) expressing one or more of an EGFR, an IL13R, or an IL4R. Thus, the in vivo or ex vivo methods are useful, inter alia, in the treatment and/or diagnosis of cancers or inflammatory disorders, which conditions include any of the cancers or inflammatory disorders (e.g., autoimmune diseases) described herein.

In some embodiments, the methods for binding a receptor-targeting reagent to a cell can also be, e.g., methods for contacting a receptor-targeting reagent to a cell, methods for killing a cell, methods for inhibiting the proliferation of a cell, or methods for detecting the presence or absence of a cell.

In Vitro Methods for Binding a Receptor-Targeting Reagent to a Cell.

Provided herein are in vitro methods for binding a receptor-targeting reagent to a cell. The method is useful, for example, in studies evaluating the efficacy of an immunotoxic receptor-targeting reagent at inhibiting the proliferation of (or killing) cancer cells in culture or in diagnostic assays for identifying one or more cells expressing certain receptors (e.g., an EGFR, an IL13R, or an IL4R). For examples, a detectably-labeled receptor-targeting reagent can be contacted to a cell sample obtained from a subject to determine if one or more cells of the cell sample express an EGFR, an IL13R, or IL4R. The methods can also serve as a "positive control" in assays to identify compounds having similar activity (e.g., similar ability to bind to a cell or where the receptor-targeting reagent is immunotoxic, similar immunotoxic properties).

The in vitro methods of binding a receptor-targeting reagent to a cell include the step of contacting a cell with any of the receptor-targeting reagents described herein. Methods for contacting a cell with a receptor-targeting reagent described herein are detailed in the accompanying Examples. For example, adherent cells can be plated on solid support matrix (e.g., a plastic tissue culture plate, or a multi-well (96 or 386-well) tissue culture plate) and grown in appropriate medium such as DMEM or RPMI medium. After seeding the cells on the solid support, the receptor-targeting reagents can be added to medium in which the cells are cultured (at various concentrations) and incubated with the cells (for varying amounts of time) under conditions that allow for the binding of the receptor-targeting reagent to the cell to occur.

The method can also, optionally, include the step of determining if the cell expresses an EGFR, an IL13R, or IL4R. Expression can be mRNA or protein expression of an EGFR, an IL13R, or an IL4R. Suitable methods of detecting protein or mRNA expression are well known to those of skill in the art and described, e.g., in Sambrook et al. (supra). These methods can include, for example, sodium dodecyl sulfate-polyacrylamide gel electrophoresis (SDS-PAGE)/western blotting techniques using antibodies specific for the target protein (see above under "Methods of Generating Antibodies"), or RT-PCR or northern blotting techniques for detection of mRNA expression.

The method can also, optionally, include the step of, after contacting the receptor-targeting reagent with the cell, determining if the receptor-targeting reagent bound to the cell. For example, a receptor-targeting reagent can be detectably-labeled as described above and after contacting the cell with the detectably-labeled receptor-targeting reagent, the binding of the reagent to the cell can be detected by detecting the presence of the detectable label. Alternatively, after contacting the cell with a non detectably-labeled receptor-targeting reagent, the binding of the receptor-targeting reagent to the cell can be detected by contacting the receptor-targeting reagent with an detectably-labeled antibody that specifically binds to the receptor-targeting reagent.

Methods of detecting and/or for quantifying a detectable label depend on the nature of the label and are known in the art. Examples of detectors useful for detecting a detectable label include, without limitation, x-ray film, radioactivity counters, scintillation counters, spectrophotometers, colorimeters, fluorometers, luminometers, and densitometers.

Suitable methods for determining if the receptor-targeting reagent bound to the cell are also detailed in the accompanying Examples.

The cells can express one or more of an EGFR (e.g., a HER1, a HER2, a HER3, or a HER4), an IL13R, or an IL4R. The cells include both prokaryotic (e.g., bacterial cells) and eukaryotic cells. Eukaryotic cells can include, for example, fungus (e.g., yeast), insect, plant, fish, reptile, and mammalian cells (e.g., mouse, rat, rabbit, guinea pig, dog, cat, pig, horse, goat, cow, whale, monkey, or human). The cells can be normal, transformed, or malignant and of any histological type, e.g., without limitation, epithelial cells, fibroblasts, lymphoid cells, macrophages/monocytes, granulocytes, keratinocytes, or muscle cells. Cancer cells can include cells from cancers such as, but not limited to, lung cancer, breast cancer, colon cancer, pancreatic cancer, renal cancer, stomach cancer, liver cancer, bone cancer, hematological cancer, neural tissue cancer (e.g., glioblastoma), melanoma, thyroid cancer, ovarian cancer, testicular cancer, prostate cancer, cervical cancer, vaginal cancer, or bladder cancer. Suitable cell lines include those recited in the accompanying Examples, e.g., glioblastoma or prostate cancer cell lines.

In embodiments where the in vitro method includes contacting a cell with an immunotoxic receptor-targeting reagent (such as any of those described herein), the methods can also be methods of inhibiting the proliferation of (or killing) a cell such as a cancer cell or an immune cell mediating an inflammatory disorder. The method can, optionally, include the step of determining if the immunotoxic receptor-targeting reagent killed the cell (or inhibited the proliferation of the cell). Generally, cells can be killed, e.g., through necrosis (cells swell and break open) or through programmed cell death (apoptosis). Methods for determining whether a cell is killed are known in the art and described in the accompanying Examples. For example, the number of viable cells in a cell population remaining after contact with an immunotoxic receptor-targeting reagent are compared to the number of viable cells in a control cell population that were not contacted with the reagent.

One method for determining the viability of a cell (or a population of cells) is trypan blue exclusion analysis. For example, cells from a well of a tissue culture dish can be trypsinized from the plate, washed, stained with a dye (e.g., typan blue), and counted using a microscope or mechanical cell counter (e.g., Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population.

Another method for determining the viability of a cell (or a population of cells) is a metabolic assay, for example, an MTT-metabolic assay (e.g., an MTT-metabolic assay from Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer. Other commonly used methods of detecting increased cell death include monitoring DNA synthesis in a population of cells (i.e., a reduction in the amount of DNA synthesis in a population of cells). Cells grown, for example, in the presence or absence of an immunotoxic receptor-targeting reagent are also treated with a nucleotide analog that can incorporate into the DNA of the cell upon cell division. Examples of such nucleotide analogs include, for example, BrdU or $^3$H-thymidine. In each case, the amount of label incorporated into the cells (grown in the presence and absence of a given inhibitory agent) is quantified, and the amount of label incorporation is directly proportional to the amount of remaining viable cells in the cell population. In this context, cell viability (e.g., cancer cell viability) can be decreased by at least 10% (e.g., at least 15%, at least 20%, at least 25%, at least 30%, at least 35%, at least 40%, at least 50%, at least 55%, at least 60%, at least 65%, at least 70%, at least 75%, at least 80%, at least 85%, at least 90%, at least 95%, or at least 99% or more) relative to the cell viability in the absence of the immunotoxic receptor-targeting reagent.

It is understood that the above methods can also be used to determine if a receptor-targeting reagent has inhibited the growth of a target cell.

Comparisons of the extent of apoptosis between cells cultured with and without an immunotoxic receptor-targeting reagent can be accomplished by measuring a host of indicators, for example, DNA fragmentation, caspase activity, loss of mitochondrial membrane potential, increased production of reactive oxygen species (ROS), intracellular acidification, chromatin condensation, phosphatidyl serine levels at the cell surface, or an increased cell permeability.

DNA fragmentation can be measured, e.g., by with the TUNEL assay (terminal deoxynucleotide transferase dUTP nick end labeling). Commercial versions of the assay are widely available, for example, APO-BrdU™ TUNEL Assay Kit (Invitrogen), APO-DIRECT™ Kit (BD-Biosciences-Pharmingen) and ApoAlert™ DNA fragmentation Assay Kit (Clontech).

Caspase activity can be measured via fluorogenic, chromogenic, and luminescent substrates specific for a given caspase (e.g., Caspase 3 or Caspase 9). Commercial kits are available for a variety of caspases such as caspase 3, caspase 7, caspase 8, and caspase 9 (see BD-Pharmingen or Invitrogen).

Loss of mitochondrial membrane potential can be measured with fluorescent dyes that selectively accumulate in various compartments of the mitochondria based on their integrity and functionality. One non-limiting example of such a dye is Mitotracker Red (Invitrogen).

Production of reactive oxygen species can be monitored with fluorescent dyes such as H2DCFDA.

Chromatin condensation can be measured with dyes such as Hoechst 33342 or propidium iodide.

Phosphotidyl serine (PS) levels can be measured at the cell surface. For example, Annexin V having a high affinity for PS, can be used to as a probe for PS on a cell surface. Numerous commercially available assay kits are suitable for such measurements (see BD-Biosciences Pharmingen).

In Vivo Methods for Binding a Receptor-Targeting Reagent to a Cell.

Also featured are in vivo methods for binding a receptor-targeting reagent to a cell. The method includes the step of delivering to a subject any of the receptor-targeting reagents described herein. The subject can be any mammal, e.g., a human (e.g., a human patient) or a non-human primate (e.g., chimpanzee, baboon, or monkey), mouse, rat, rabbit, guinea pig, gerbil, hamster, horse, a type of livestock (e.g., cow, pig, sheep, or goat), a dog, cat, or a whale. The subject can be one having, suspected of having, or at risk of developing a cancer or an inflammatory disorder.

Where the receptor-targeting reagent is immunotoxic (i.e., the receptor-targeting reagent contains one or more toxic domains), the in vivo methods for binding a receptor-targeting reagent to a cell can be methods of inhibiting the proliferation of (or killing) a cancer cell.

Generally, the receptor-targeting reagents delivered to the subject will be suspended in a pharmaceutically-acceptable carrier (e.g., physiological saline) and administered orally, rectally, or parenterally, e.g., injected intravenously, subcutaneously, intramuscularly, intrathecally, intraperitoneally, intrarectally, intravaginally, intranasally, intragastrically, intratracheally, or intrapulmonarily (as described above). The receptor-targeting reagents can also be delivered directly to cells or a tissue (e.g., tumor cells). Where the receptor-targeting reagents are immunotoxic, the methods can be used to kill tumor cells or immune cells mediating an inflammatory disorder or, e.g., to kill any residual tumor cells in a tumor bed following surgical resection of a tumor.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of receptor-targeting reagents and the differing efficiencies of various routes of administration. For example, oral administration may require higher dosages than administration by intravenous injection. Variations in these dosage levels can be adjusted using standard empirical routines for optimization as is well understood in the art.

Administrations can be single or multiple (e.g., 2-, 3-, 4-, 6-, 8-, 10-, 20-, 50-, 100-, 150-, or more fold). Encapsulation of the receptor-targeting reagent in a suitable delivery vehicle (e.g., polymeric microparticles or implantable devices) may increase the efficiency of delivery, particularly for oral delivery.

Alternatively, a polynucleotide containing a nucleic acid sequence encoding the receptor-targeting reagent can be delivered to appropriate cells in a mammal. Expression of the coding sequence can be directed to any cell in the body of the subject. However, expression will preferably be directed to the target cells themselves or in some instances, in the vicinity of the cells whose viability it is desired to decrease. This can be achieved by, for example, the use of polymeric, biodegradable microparticle or microcapsule delivery devices known in the art. Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995), J. Mol. Med. 73:479, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated subject. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Schedules and co-administration can be any of those described herein (see, for example, "Methods of Treatment").

In some embodiments, the in vivo methods can include the step of determining whether a subject has a cancer or an inflammatory disorder. Where the subject has (or is determined to have) a cancer or an inflammatory disorder, the methods can include the step of determining if one or more cells of the subject's cancer or one or more immune cells mediating the subject's inflammatory condition express an EGFR, an IL13R, or an IL4R. Methods for determining expression of an EGFR, an IL13R, or an IL4R are described above.

Immunotoxic receptor-targeting reagents or pharmaceutical compositions thereof, can in some embodiments, be administered to a subject after the subject is administered an non-immunotoxic receptor-targeting reagent, e.g., to decrease the number or severity of one or more side-effects associated with a immunotoxic therapy (see below).

Any of the receptor-targeting reagents can also, in some instances, be co-administered with one or more additional therapies or therapeutic agents such as chemotherapeutic agents. Methods for co-administration and exemplary additional therapies and therapeutic agents that can be co-administered with any of the receptor-targeting reagents described herein are detailed below.

Where the receptor-targeting reagent delivered to the subject is detectably-labeled, the in vivo methods can be used to detect the presence of a cell, e.g., a cell expressing an EGFR, an IL13R, or an IL4R. That is, any of the detectably-labeled receptor-targeting reagents described herein can be used as probes, e.g., to guide surgery or detect a disease. For example, an area suspected of containing cancer cells (e.g., a primary tumor or microscopic metastases) can be exposed to a receptor-targeting reagent capable of binding to the cell (through an EGFR, an IL13R, or an IL4R). Thus, all cancer cells to which the receptor-targeting reagent binds will be differentiated from the non-cancer cells and can aid in the treatment of the cancer (e.g., surgical removal of the cancer or targeted chemotherapy). In another example, cells detectably labeled by a receptor-targeting reagent described herein can be isolated away from non-labeled cells. For example, certain types or populations of cells (e.g., B cell or T cell populations (e.g., B cell or T cell populations mediating an inflammatory disorder) or stem cell populations) can be detected and isolated from non-detectably labeled cells. Detectably labeled cells can also be visualized in vivo to determine, e.g., their localization. In vivo methods of detecting the receptor-targeting reagents depend of course on the nature of the detectable label and can include, e.g., bioluminescence imaging, micro positron emission tomography/single photon emission commuted tomography, magnetic resonance imaging, and intravital microscopy (see, e.g., Dustin (2003) Arthritis Res. Ther. 5:165-171, the disclosure of which is incorporated herein by reference in its entirety).

Further description of suitable in vivo methods (e.g., methods of treatment using the receptor-targeting reagents described herein) can be found under "Methods of Treatment."

Ex Vivo Methods for Binding a Receptor-Targeting Reagent to a Cell.

An ex vivo strategy can involve transfecting or transducing cells obtained from the subject to be treated (or another subject) with a polynucleotide encoding a receptor-targeting reagent (e.g., an immunotoxic receptor-targeting reagent) that, e.g., is capable of binding to a target cell or killing a target cell. The transfected or transduced cells are then administered to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the receptor-targeting reagent for as long as they survive in the subject. Alternatively, tumor cells or inflammatory cells (e.g., immune cells), preferably obtained from the subject (autologous) but potentially from a subject of the same species other than the subject (allogeneic), can be transfected or transformed by a vector encoding the receptor-targeting reagent. The tumor cells, preferably treated with an agent (e.g., ionizing irradiation) that ablates their proliferative capacity, are then introduced into the subject, where they secrete the receptor-targeting reagent.

The ex vivo methods include the steps of harvesting cells from a subject, culturing the cells, transducing them with an expression vector, and maintaining the cells under conditions suitable for expression of the receptor-targeting reagent. These methods are known in the art of molecular biology. The transduction step is accomplished by any standard means used for ex vivo gene therapy, including calcium phosphate, lipofection, electroporation, viral infection, and biolistic gene transfer (also see above). Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the same or another subject.

In some embodiments, the ex vivo methods can be used to purge a cell population from a mixture of cells. For example, a mixture of cells (e.g., bone marrow or any other stem cell population) obtained from a subject with cancer (e.g., any of the cancers described herein) can be purged of any cancer cells therein. The mixture of cells can be contacted with an immunotoxic receptor-targeting reagent described herein to kill cancer cells contained therein. Following the killing of the cancer cells, the mixture of cells can be returned to the subject, e.g., after the subject has been treated with a chemotherapeutic agent.

Methods for Pre-Conditioning a Subject for an Immunotoxic Therapy

Also featured are in vivo and ex vivo methods for pre-conditioning a subject for an immunotoxic therapy. As set forth in the accompanying Examples, administering to a mammal a non-immunotoxic receptor-targeting reagent prior to administering to the mammal an immunotoxin significantly reduced the toxic side-effects associated with the immunotoxin. Thus, the methods described herein are useful in decreasing the number and/or the severity of one or more (e.g., two or more, three or more, four or more, five or more, six or more, seven or more, or eight or more) side-effects associated with an immunotoxic therapy.

As used herein, an "immunotoxin" refers to any immunotoxic agent that contains at least one targeting domain that directs the agent to target cells of interest (e.g., cancer cells or immune cells mediating an inflammatory disorder) and at least one toxic domain that inhibits the proliferation (or kills)

the target cell. Immunotoxins can include the immunotoxic receptor-targeting reagents described herein.

As used herein, a "non-immunotoxic receptor-targeting reagent" is a receptor-targeting reagent that does not include a toxic domain (such as any of the toxic domains described herein). Thus, as used herein, a non-immunotoxic receptor-targeting reagent is a receptor-targeting agent that contains one or more targeting domains that direct the agent to target cells of interest (e.g., cancer cells or immune cells mediating an inflammatory disorder) but no toxic domain. These receptor targeting agents are sometimes stated herein to consist essentially of one or more of such targeting domains. For example, a non-immunotoxic receptor-targeting reagent can consist essentially of: (a) an epidermal growth factor receptor (EGFR)-binding agent and (b) an IL-13 receptor (IL13R)-binding agent or an IL-4 receptor (IL4R)-binding agent, wherein (a) is bound to (b). However, it is understood that a receptor-targeting reagent that consists essentially of one or more targeting domain(s) can include components other than a toxic domain such as, but not limited to, a linker, a detectable label, or a post-translation modification such as, e.g., a phosphorylation or a glycosylation (see above).

Side-effects associated with an immunotoxic therapy vary depending on, e.g., the nature of the immunotoxin (the toxic domain of a receptor-targeting reagent), the general health of the subject so treated, the dosage of the immunotoxin, and/or the duration for which the immunotoxin is administered to the subject. Side-effects can include, e.g., muscle effects (e.g., drooping eyelids, paralysis of the tongue, or difficulty swallowing), difficulty breathing, weight loss, hepatotoxicity, hypoalbuminemia, vascular leak syndrome, myalgias, or a combination of one or more of any of the foregoing. In some instances, the immunotoxic therapy can cause extreme toxicity (near fatal toxicity) in the subject.

In Vivo Methods for Pre-Conditioning a Subject for an Immunotoxic Therapy.

In vivo methods for pre-conditioning a subject for an immunotoxic therapy (methods of reducing one or more side-effects associated with an immunotoxic therapy) include the step of prior to delivering to a subject an immunotoxin, delivering to the subject a non-immunotoxic reagent that binds to the same target as the immunotoxin but does not comprise a toxic domain (i.e., is not immunotoxic).

The immunotoxin (e.g., an immunotoxic receptor-targeting reagent) can specifically bind to any of a variety of target analytes. For example, the immunotoxin can bind to any number of cell-surface molecules such as receptors (e.g., an EGFR, an interleukin receptor (e.g., a receptor to any one of interleukins 1-30 such as an IL13R or an IL4R), adhesion molecules (e.g., integrins, adhesins, cohesins, or cadherins), or cell specific markers (e.g., a cell-specific marker for a B cell or T cell mediating an immunological disorder or for a cancer such as). The immunotoxin can be a monospecific or a multi-specific (e.g., bispecific or trispecific) immunotoxin. For example, the immunotoxin can contain an epidermal growth factor receptor (EGFR)-binding agent, an IL-13 receptor (IL13R)-binding agent, or an IL-4 receptor (IL4R)-binding agent. The immunotoxin can contain, e.g.: (a) a first targeting domain comprising an epidermal growth factor receptor (EGFR)-binding agent; and (b) a second targeting domain comprising an IL-13 receptor (IL13R)-binding agent or an IL-4 receptor (IL4R)-binding agent.

The immunotoxin can contain one or more of any of the toxic domains described herein. For example, the immunotoxin can contain one or more of a radionuclide, a toxic small molecule, a toxic polypeptide (e.g., a *Diphtheria* toxin or a *Pseudomonas* toxin A) as described above.

Additional immunotoxins for use in the methods for pre-conditioning a subject for an immunotoxic therapy are described in, e.g., U.S. Publication No. 20020048550 and U.S. Pat. No. 7,101,542, the disclosures of each of which are incorporated by reference in their entirety.

Generally, an immunotoxin and a non-immunotoxic reagent will have the same specificity in terms of target and valency. For example, in instances where the immunotoxin is monospecific (e.g., comprises an EGFR-binding domain), the non-immunotoxic reagent can also be monospecific (e.g., comprising an EGFR-binding domain). In instances where the immunotoxin is multi-specific (e.g., bispecific), the non-immunotoxic reagent can also be multi-specific. That is, where a multi-specific immunotoxin binds to target A and target B, the non-immunotoxic reagent can also bind to target A and target B. However, the non-immunotoxic reagent can be monospecific. For example, where a multi-specific immunotoxin binds to target A and target B, the non-immunotoxic reagent can bind to target A or target B.

In embodiments where the immunotoxin is multi-specific and the non-immunotoxic reagent is monospecific, more than one monospecific non-immunotoxic reagent can be administered before the immunotoxin. For example, a mixture of a monospecific non-immunotoxic reagent specific for target A and a monospecific non-immunotoxic reagent specific for target B can be administered to a subject prior to administering to the subject a multi-specific immunotoxin specific for target A and target B.

The immunotoxin and the non-immunotoxic reagent can differ only in the presence of a toxic domain, but can otherwise be identical. For example, an immunotoxin can consist of an EGFR-binding domain and a *Diphtheria* toxin and the non-immunotoxic reagent can consist of the EGFR-binding domain.

In some embodiments, the non-immunotoxic reagent can be administered to a subject at less than 24 hours (e.g., less than 22 hours, less than 20 hours, less than 16 hours, less than 15 hours, less than 12 hours, less than 11 hours, less than 10 hours, less than nine hours, less than eight hours, less than six hours, less than five hours, less than three hours, less than two hours, less than 90 minutes, less than 60 minutes, less than 55 minutes, less than 50 minutes, less than 45 minutes, less than 40 minutes, less than 35 minutes, less than 30 minutes, less than 25 minutes, less than 20 minutes, less than 15 minutes, less than 10 minutes, less than nine minutes, less than eight minutes, less than seven minutes, less than six minutes, less than five minutes, less than four minutes, less than three minutes, less than two minutes, or less than 1 minute) prior to administering the immunotoxin to the subject.

In some embodiments, the non-immunotoxic reagent can be administered to a subject at the same time (simultaneously) with the corresponding immunotoxin.

In some embodiments, the non-immunotoxic reagent can be administered to the subject as a single dose. In some embodiments, the non-immunotoxic reagent can be administered to the subject in multiple (e.g., two, three, four, five, six, seven, eight, nine, 10, 11, 12, 13, 14, 15, 16, 17, 18, 19, 20, or 25 or more) discrete doses.

In some embodiments, the in vivo methods of pre-conditioning a subject for an immunotoxic therapy include prior to delivering to a subject any of the immunotoxic receptor-targeting reagents described herein, delivering to the subject a corresponding (e.g., in specificity and valency) a non-immunotoxic receptor-targeting reagent described herein. For example, the immunotoxic receptor-targeting reagent can contain: (a) an epidermal growth factor receptor (EGFR)-binding agent; (b) an IL-13 receptor (IL13R)-binding agent or an IL-4 receptor (IL4R)-binding agent, and a toxic domain; wherein (a) is bound to (b), and the non-immunotoxic receptor-targeting reagent can contain: (a) an epidermal growth factor receptor (EGFR)-binding agent and (b) an IL-13 receptor (IL13R)-binding agent or an IL-4 receptor (IL4R)-binding agent, wherein (a) is bound to (b), and wherein the receptor-targeting reagent does not comprise a toxic domain.

Any of the in vivo methods for pre-conditioning can also include the step of, e.g., determining if a subject has a cancer or an inflammatory disorder or, if the subject has (or has been determined to have) a cancer or an inflammatory disorder, determining if one or more cells of the subject's cancer or one or more immune cells mediating the inflammatory disorder express the analyte targeted by the immunotoxin or non-immunotoxic reagent. For example, where an immunotoxin (and/or a non-immunotoxic reagent) contains an EGFR-binding domain and an IL13R-binding domain, the expression (e.g., mRNA or protein expression) of EGFR and/or IL13R could be determined as described above.

Alternatively, the in vivo methods for pre-conditioning can include the step of determining if one or more target analytes are present on one or more cells of the subject's cancer or one or more immune cells mediating the inflammatory disorder. For example, the presence of one or more specific receptors (e.g., an EGFR, an IL13R, or an IL4R) could be determined and then an appropriate immunotoxin and corresponding non-immunotoxic reagent(s) can be selected and/or administered to the subject.

The in vivo methods can also include the step of determining if the number or severity of one or more side-effects of an immunotoxic therapy have been reduced. Such side-effects are described above and methods for evaluating the number or severity of the side-effects are known in the medical arts.

As described above, the pre-conditioning of a subject for an immunotoxic therapy (that is decreasing one or more side-effects of an immunotoxic therapy) can involve ex vivo techniques of transfecting or transducing cells obtained from the subject to be treated (or another subject) with a polynucleotide encoding a receptor-targeting reagent (e.g., a receptor-targeting reagent that does not contain a toxic domain) that, e.g., is capable of preconditioning a subject for an immunotoxic therapy.

Further description of suitable in vivo methods for preconditioning a subject for an immunotoxic therapy (e.g., dosing, use in combination therapy, etc) can be found under "Methods of Treatment."

Diseases Treatable by a Therapy Comprising a Receptor-Targeting Reagent

The receptor-targeting reagents (e.g., the immunotoxic receptor-targeting reagents) described herein can be used to treat a variety of proliferative disorders and/or inflammatory disorders. Proliferative disorders include, e.g., cancers, certain immune disorders (such as inflammatory disorders, or warts). Examples of some specific disorders that can be treated (or in some instances prevented) by the administration of one or more receptor-targeting reagents are reviewed in the following sections.

Cancer

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer (e.g., glioblastoma such as glioblastoma multiforme), melanoma, thyroid cancer, ovarian cancer, testicular cancer, prostate cancer, cervical cancer, vaginal cancer, or bladder cancer.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a subject can also be one "at risk of developing a cancer" when the subject has been exposed to mutagenic or carcinogenic levels of certain compounds (e.g., carcinogenic compounds in cigarette smoke such as acrolein, arsenic, benzene, benz{a}anthracene, benz{a}pyrene, polonium-210 (Radon), urethane, or vinyl chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like.

In addition to the administration of one or more receptor-targeting reagents described herein, a cancer can also be treated by chemotherapeutic agents, ionizing radiation, immunotherapy agents, or hyperthermotherapy agents. Chemotherapeutic agents include, but are not limited to, cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, and methotrexate. As described above, any of these non-receptor-targeting reagent therapies can be co-administered (administered in a combination therapy regimen) with any of the receptor-targeting reagents described herein (see below under "Methods of Treatment").

Inflammatory Disorders

An "inflammatory disorder," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such immune cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be a response that is inappropriate in magnitude or duration, e.g., anaphylaxis. Thus, the inappropriately targeted response can be due to the presence of a microbial infection (e.g., viral, bacterial, or fungal). Types of inflammatory disorders (e.g., autoimmune disease) can include, but are not limited to, osteoarthritis, rheumatoid arthritis (RA), spondyloarthropathies, POEMS syndrome, Crohn's disease, graft-versus host disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Barre syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory disorders are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory disorders can also include ulcerative colitis and asthma.

A subject "at risk of developing an inflammatory disorder" refers to a subject with a family history of one or more inflammatory disorders (e.g., a genetic predisposition to one or more inflammatory disorders) or one exposed to one or more inflammation-inducing conditions. For example, a subject can have been exposed to a viral or bacterial superantigen such as, but not limited to, Staphylococcal enterotoxins (SEs), a *Streptococcus pyogenes* exotoxin (SPE), a *Staphylococcus aureus* toxic shock-syndrome toxin (TSST-1), a *Streptococcal* mitogenic exotoxin (SME) and a *Streptococcal* superantigen (SSA). From the above it will be clear that subjects "at risk of developing an inflammatory disorder" are not all the subjects within a species of interest.

A subject "suspected of having an inflammatory disorder" is one who presents with one or more symptoms of an inflammatory disorder. Symptoms of inflammatory disorders are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain.

In addition to the administration of one or more altered receptor-targeting reagents described herein, an inflammatory disorder can also be treated by non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept). As described above, any of these non-receptor-targeting reagent therapies can be co-administered (administered in a combination therapy regimen) with any of the receptor-targeting reagents described herein (see below under "Methods of Treatment").

Methods for Selecting an Appropriate Therapeutic Modality for a Subject

Also provided herein are methods for selecting an appropriate therapeutic modality for a subject (e.g., a human such as one having a cancer or inflammatory disorder), which methods are useful to, e.g., medical professionals in effectively and appropriately treating subjects having disorders such as cancers or inflammatory disorders.

The method can include the step of selecting as a therapeutic agent for the subject having cancer or an inflammatory disorder any of the receptor-targeting reagents described herein (e.g., any of the immunotoxic receptor-targeting reagents described herein) if one or more cancer cells of the subject's cancer, or one or more immune cells mediating a subject's inflammatory disorder, express an IL13R, and IL4R, or an EGFR. The method can also include the step of determining if one or more cancer cells of the subject's cancer, or one or more immune cells mediating a subject's inflammatory disorder, express an IL13R, an EGFR, or an IL4R. Methods for determining whether a cell expresses an IL13R, an IL4R, or an EGFR receptor are described above.

In some instances where a medical practitioner selects for a subject a therapy comprising an immunotoxic receptor-targeting reagent, the practitioner may also select a therapy comprising a non-immunotoxic receptor-targeting reagent. For example, the medical professional can select a first therapy comprising a non-immunotoxic receptor-targeting reagent and a second therapy comprising an immunotoxic receptor-targeting reagent. It is understood that two different therapies (e.g., a therapy comprising an immunotoxic receptor-targeting reagent and a therapy comprising a non-immunotoxic receptor-targeting reagent) can be selected for a subject by different medical professionals. For example, one medical professional can select for a subject a first therapy comprising an immunotoxic receptor-targeting reagent and a second medical professional can select for the subject a therapy comprising a non-immunotoxic receptor-targeting reagent.

In accordance with the methods described herein, any medical practitioner (e.g., a doctor or a nurse) can select an appropriate therapeutic modality for the subject so identified as having one or more cancer cells (or immune cells mediating an inflammatory disorder) that express an EGFR, an IL13R, or an IL4R. Selecting a therapy for a subject can be, e.g.: (i) writing a prescription for a medicament; (ii) giving (but not necessarily administering) a medicament to a subject (e.g., handing a sample of a prescription medication to a patient while the patient is at the physician's office); (iii) communication (verbal, written (other than a prescription), or electronic (email, post to a secure site)) to the patient of the suggested or recommended therapeutic modality (e.g., an immunotoxic receptor-targeting reagent described herein); or (iv) identifying a suitable therapeutic modality for a subject and disseminating the information to other medical personnel, e.g., by way of patient record. The latter (iv) can be useful in a case where, e.g., more than one therapeutic agent are to be administered to a patient by different medical practitioners. It is understood that an electronic communication can be, e.g., one stored on a computer or other electronic media such as a DVD, CD, or floppy disk) or in a written (e.g., printed) form.

After selecting an appropriate therapeutic modality for a subject, a medical practitioner (e.g., a doctor or a nurse) can administer the appropriate therapeutic modality to the subject (e.g., any of the receptor-targeting reagents described herein). Methods of administering a receptor-targeting reagent (e.g., an immunotoxic receptor-targeting reagent) to a mammal are described below and in the accompanying Examples.

Methods of Treatment

Administration of a receptor-targeting reagent described herein or pharmaceutical composition thereof can be systemic or local. As described above, pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted receptor-targeting reagent production cells). See, e.g., U.S. Pat. Nos. 4,407,957, 5,798,113, and 5,800,828, each incorporated herein by reference in their entirety. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984), incorporated herein by reference in its entirety); microencapsulation (see, e.g., U.S. Pat. Nos. 4,352,883; 4,353,888; and 5,084,350, herein incorporated by reference in its entirety); continuous release polymer implants (see, e.g., Sabel, U.S. Pat. No. 4,883,666, incorporated herein by reference in its entirety); macroencapsulation (see, e.g., U.S. Pat. Nos. 5,284,761, 5,158,881, 4,976,859 and 4,968,733 and published PCT patent applications WO92/19195, WO 95/05452, the disclosures of each of which are incorporated herein by reference in their entirety); injection, either subcutaneously, intravenously, intra-arterially, intramuscularly, or to other suitable site; or oral administration, in capsule, liquid, tablet, pill, or prolonged release formulation.

Therapeutically effective amounts of a pharmaceutical composition can be administered to a subject in need thereof in a dosage regimen ascertainable by one of skill in the art. For example, a composition can be administered to the subject, e.g., systemically at a dosage from 0.001 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a receptor-targeting reagent (e.g., an immunotoxic receptor-targeting reagent) can be first administered at different dosing regimens. The unit dose and regimen depend on factors that include, e.g., the species of mammal, its immune status, the body weight of the mammal. Typically, levels of a receptor-targeting reagent in a tissue can be monitored using appropriate screening assays as part of a clinical testing procedure, e.g., to determine the efficacy of a given treatment regimen.

The frequency of dosing for a receptor-targeting reagent is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such receptor-targeting reagents (e.g., immunotoxic receptor-targeting reagents) or pharmaceutical compositions thereof can be determined by known pharmaceutical procedures in, for example, cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the $ED_{50}$ with little or no toxicity. The dosage may vary within this range depending upon the dosage form employed and the route of administration utilized. For a pharmaceutical composition used as described herein (e.g., for treating a proliferative disorder in a subject), the therapeutically effective dose can be estimated initially from cell culture assays. A dose can be formulated in animal models to achieve a circulating plasma concentration range that includes the $IC_{50}$ (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography. Methods for determining an $IC_{50}$ for a receptor-targeting reagent in cell culture are detailed in the accompanying Examples.

As defined herein, a "therapeutically effective amount" of a receptor-targeting reagent is an amount of the reagent that is capable of producing a medically desirable result (e.g., amelioration of one or more symptoms of a proliferative disorder, decreased proliferation of cancer cells or immune cells mediating an inflammatory disorder, or a decrease in one or more side-effects associated with an immunotoxic therapy) in a treated subject. A therapeutically effective amount of a receptor-targeting reagent (i.e., an effective dosage) includes milligram, microgram, nanogram, or picogram amounts of the reagent per kilogram of subject or sample weight (e.g., about 1 nanogram per kilogram to about 500 micrograms per kilogram, about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any of those described herein, e.g., a mammal such as a human.

A receptor-targeting reagent or pharmaceutical composition thereof described herein can be administered to a subject as a combination therapy with another treatment, e.g., a treatment for a proliferative disorder (e.g., a cancer or an inflammatory disorder). For example, the combination therapy can include administering to the subject (e.g., a human patient) one or more additional agents that provide a therapeutic benefit to the subject who has, or is at risk of developing, (or suspected of having) a proliferative disorder. Thus, the receptor-targeting reagent or pharmaceutical composition and the one or more additional agents can be administered at the same time. Alternatively, the receptor-targeting reagent can be administered first in time and the one or more additional agents administered second in time. The one or more additional agents can be administered first in time and the receptor-targeting reagent administered second in time. The receptor-targeting reagent can replace or augment a previously or currently administered therapy. For example, upon treating a subject with a receptor-targeting reagent, administration of the one or more additional agents can cease or diminish, e.g., be administered at lower levels. Administration of the previous therapy can also be maintained. In some instances, a previous therapy can be maintained until the level of the receptor-targeting reagent (e.g., the dosage or schedule) reaches a level sufficient to provide a therapeutic effect. The two therapies can be administered in combination.

It will be appreciated that in instances where a previous therapy is particularly toxic, administration of a receptor-targeting reagent can be used to offset and/or lessen the amount of the previously therapy to a level sufficient to give the same or improved therapeutic benefit, but without the same level of toxicity. Of course, prior to administering to the subject an immunotoxic receptor-targeting reagent, a medical practitioner can administer to the subject a non-immunotoxic receptor-targeting reagent.

In some instances, when the subject is administered a receptor-targeting reagent or pharmaceutical composition of the invention the first therapy is halted. The subject can be monitored for a first pre-selected result, e.g., an improvement in one or more symptoms of a proliferative disorder such as any of those described herein (e.g., see above). In some cases, where the first pre-selected result is observed, treatment with the receptor-targeting reagent is decreased or halted. The subject can then be monitored for a second pre-selected result after treatment with the receptor-targeting reagent is halted, e.g., a worsening of a symptom of a proliferative disorder. When the second pre-selected result is observed, administration of the receptor-targeting reagent to the subject can be reinstated or increased, or administration of the first therapy is reinstated, or the subject is administered both a receptor-targeting reagent and first therapy, or an increased amount of the receptor-targeting reagent and the first therapeutic regimen.

The receptor-targeting reagent can also be administered with a treatment for one or more symptoms of a disease (e.g., proliferative disorder). For example, the receptor-targeting reagent can be co-administered (e.g., at the same time or by any combination regimen described above) with, e.g., a pain medication.

It is understood that the Methods of Treatment described in this section augment, where applicable, the in vivo methods described above.

Kits and Articles of Manufacture

Also provided herein are kits containing one or more of any of the receptor-targeting reagents described herein and, optionally, instructions for administering the one or more receptor-targeting reagents to a subject (e.g., a human or any of the subjects described herein). The subject can have, or be suspected of having, a cancer or an inflammatory disorder. The kits can also, optionally, include one or more pharmaceutically acceptable carriers or diluents.

Also featured are kits useful for detecting expression of an EGFR, IL4R, and/or an IL13R. The kits can contain one or more reagents for detecting expression of an IL13R, IL4R, or EGFR; and instructions for administering any of the receptor-targeting reagents described herein (e.g., the immunotoxic receptor-targeting reagents described herein) if the expression of an IL13R, an IL4R, or an EGFR is detected.

The kits can optionally include, e.g., a control sample that is known to contain (positive control), or not to contain (negative control), an EGFR, an IL4R, or an IL13R mRNA or protein. In some embodiments, the kits can include one or more reagents for processing a sample (e.g., a cell sample). For example, a kit can include reagents for isolating mRNA or protein from a sample and/or reagents for amplifying isolated mRNA (e.g., reverse transcriptase, primers for reverse transcription or PCR amplification, or dNTPs) and/or detecting protein expression (e.g., one or more antibodies specific for an EGFR, an IL13R, or an IL4R).

The disclosure also provides an article of manufacture containing: a container and a composition contained within the container. The composition is an active agent for treating cancer (or an inflammatory disorder) in a mammal. The active agent in the composition can contain, or consist of, any of the immunotoxic receptor-targeting reagents described herein and the container can have a label indicating that the composition is for use in treating cancer (or an inflammatory disorder) in a mammal. The label can further indicate that the composition is to be administered to the mammal if one or more cancer cells of the mammal's cancer (or one or more immune cells mediating an inflammatory disorder) express an IL13R, an IL4R, or an EGFR. The article of manufacture can also contain instructions for administering the composition (e.g., the rehydrated composition) to the mammal.

In some embodiments, the composition can be dried or lyophilized. The composition can be ready to administer without need for rehydration or further formulation.

The following examples are intended to illustrate, not limit, the invention.

EXAMPLES

Example 1

Materials and Methods

Figure 1B:
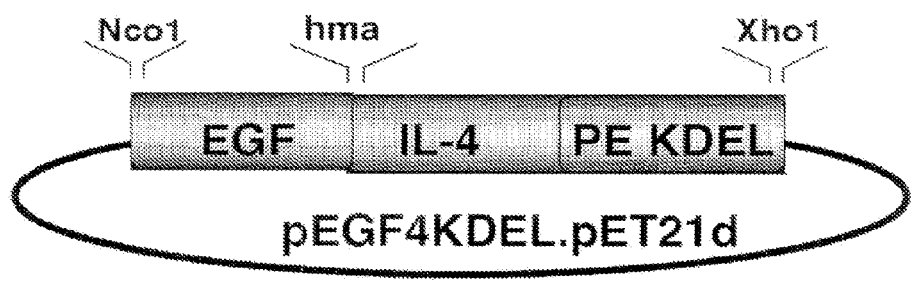
FIG. 1B is a schematic diagram depicting the EGF4KDEL construct. The gene fragment encoding the single-chain bispecific immunotoxin EGF4KDEL was created using overlap extension PCR. This construct consisted of (from 5' to 3') nucleic acid encoding a truncated human epidermal growth factor (EGF), a flexible 20 amino acid segment of human muscle aldolase (hma), human interleukin-4 (IL-4), a biologically active fragment of *Pseudomonas* exotoxin (PE) A (SEQ ID NO:12), and a KDEL (SEQ ID NO:15) amino acid sequence. Using the NcoI/XhoI restriction sites the nucleic acid sequence encoding EGF4 KDEL was cloned in the pET21d bacterial expression vector.

Construction of DTEGF13. The synthesis and assembly of hybrid genes encoding the single chain bispecific immunotoxin (BIT) DTEGF13 was accomplished using DNA shuffling and DNA cloning techniques. The fully assembled fusion construct (from 5' end to 3' end) consisted of an Nco1 restriction enzyme site, an ATG transcription initiation codon, a nucleotide sequence encoding the first 389 amino acids of the *Diphtheria* toxin (DT) molecule (hereinafter referred to as $DT_{390}$), a nucleotide sequence encoding the 7 amino acid EASGGPE (SEQ ID NO:14) linker, nucleotide sequences encoding human epidermal growth factor (EGF), the nucleotide sequence encoding a 20 amino acid segment (PSGQAGAAASESLFVSNHAY (SEQ ID NO:13) of human muscle aldolase (hma), a nucleotide sequence encoding an interleukin 13 (IL13), and a XhoI restriction site. The resultant 1,755 base pair (bp) NcoI/XhoI-flanked fragment gene was cloned into the pET21d expression vector under the control of an isopropyl-β-D-thiogalactopyranoside (IPTG) inducible T7 promoter (FIG. 1). DNA sequencing analysis (Biomedical Genomics Center, University of Minnesota) was used to verify that the nucleotide sequence of the cloned gene was correct and was in frame. Nucleotide sequences encoding monospecific immunotoxins (MIT)-fusion proteins of $DT_{390}$ and human EGF (DTEGF) or $DT_{390}$ and human IL13 (DTIL13) were constructed using the same techniques.

An additional bispecific fusion protein containing the $DT_{390}$ fragment was created for a specificity control. The DT2222 control was constructed by joining two repeating sFv molecules specific for human anti-CD22 antibodies to $DT_{390}$.

Construction of DT2219EA. Using standard molecular biology techniques, a variation of DT2219 was constructed DT2219EA. The DT2219EA construct contained a nucleic acid sequence containing an Nco I restriction site, followed by a downstream ATG initiation codon, a nucleic acid sequence encoding the first 389 amino acids of the DT ($DT_{390}$), the $V_H$ and $V_L$ regions of anti-CD22 (sFv) and anti- CD 19 linked by a 20 amino acid segment of human muscle aldolase (hma), and a Xho1 compatible restriction site. Three amino acids Thr-His-Trp (THW) were substituted for Ser-Ser-Tyr (SSY) at positions 100, 100A, and 100B in the CDR3 region of the $V_H$ of the anti-CD22 sFv enhanced its affinity for CD22, so these same amino acids were mutated in the assembled plasmid called pDT2219hmaEA (or Enhanced Affinity).

Construction of DT2219ARL. The hybrid gene encoding DT2219ARL was constructed using assembly PCR. The two major differences between DT2219ARL and DT2219EA were: 1) reversal of the orientation of the $V_H$ and $V_L$ chains. In DT2219ARL, the $V_L$ proceded the $V_H$; and 2) The VL and VH genes of each sFv were conjoined by a fragment encoding the ARL linker (GSTSGSGKPGSGEGSTKG; SEQ ID NO:21) and the two sFv genes were linked by a fragment encoding $G_4S$ linker. In its final configuration, the DT2219ARL Nco1/Xho1 gene fragment encoded a start codon followed first 389 amino acids of DT390, and then a 7 amino acid linker EASPEEA (SEQ ID NO:22), followed by the anti-CD22 sFv, and then the CD19 sFv. The final target gene was cloned using standard molecular biology techniques into the pET21d vector expression vector to allow for expression in bacteria.

Inclusion Body Isolation. Expression plasmids encoding the above-described fusion proteins were transformed into *E. coli* strain BL21(DE3) (Novagen, Madison, Wis.) bacteria. Following an overnight culture, the bacteria were grown in 800 ml of Luria broth (LB) containing 50 mg/ml carbenicillin in a 2-liter flask at 37° C. with shaking. Expression of the fusion proteins was induced when the culture media reached an $OD_{600}$ of 0.65 by adding 8 ml of 100 mM isopropyl-β-D-thiogalactopyranoside (FisherBiotech, Fair Lawn, N.J.). Two hours after induction commenced, bacteria were harvested by centrifugation. Bacterial cell pellets were resuspended and homogenized in a buffer solution (50 mM Tris, 50 mM NaCl, and 5 mM EDTA pH 8.0) using a polytron homogenizer. Following homogenization, the bacterial homogenate was subjected to centrifugation and the resulting pellets were resuspended and washed with a buffer containing: 0.3% sodium deoxycholate (DOC), 5% Triton X-100, 10% glycerin, 50 mmol/L Tris, 50 mmol/L NaCl, 5 mmol/L EDTA (pH 8.0).

Refolding and Purification. Inclusion bodies were dissolved at 20:1 (mg wet weight:mL) in solubilization buffer (7 M Guanidine Hydrochloride, 50 mM Tris, 50 mM NaCl, 5 mM EDTA and 50 mM DTT, pH 8.0). Following a one hour incubation at 37° C., the mixture was subjected to centrifugation and the pellet discarded. The supernatant was diluted 20-fold with refolding buffer (50 mM Tris-HCl, 50 mM NaCl, 0.8 mM L-arginine, 20% glycerin, 5 mM EDTA and 1 mM GSSG, pH 8.0) and incubated at 4° C. for 2 days. The guanidine hydrochloride was removed from the solution by dialysis: 10-fold dialysis against 20 mM Tris-HCl, pH 9.0. Refolded proteins were purified using fast protein liquid chromatography-ion exchange chromatography (Q sepharose Fast Flow™, Sigma, St. Louis, Mo.) with a continuous salt gradient from 0.2 to 0.5 M NaCl in 20 mM Tris-HCl (pH 9.0) over four column volumes.

Cell Culture. The human prostate cancer cell lines DU-145 and PC-3, the human colorectal cancer cell line HT-29, the human Burkitt's Lymphoma cell line Daudi, and Calu-3 (a human lung adenocarcinoma) were obtained from the American Type Culture Collection (ATCC, Rockville Md.). The human glioblastoma cell lines U-87 and U-118 were derived from patients with glioblastoma multiforme (GBM) and were also obtained from the ATCC. U87 and U118 cells were grown in DMEM whereas the other cell lines were maintained in RPMI-1640 media (Cambrex, East Rutherford N.J.) supplemented with 10% fetal bovine serum, 2 mmol/L L-glutamine, 100 units/mL penicillin, and 100 μg/mL streptomycin. All carcinoma cells were grown as monolayers, whereas the Daudi cells were cultured in suspension using culture flasks. Cell cultures were incubated in a humidified 37° C. atmosphere containing 5% $CO_2$. When adherent cells were 80-90% confluent, they were passaged using trypsin-EDTA to detach the cells from the culture dish. Only cells with viability >95%, as determined by trypan blue exclusion, were used for the experiments described herein (see below).

Bioassays to measure cell proliferation. To determine the effect of DTEGF13 on DU-145, U118, U87-MG, HT-29, Daudi cells, and other cell lines described below, proliferation assays measuring $^3$H-thymidine incorporation were used. Cells were seeded (at $10^4$ cells per well) in a 96-well flat-bottomed plate and incubated overnight at 37° C. with 5% $CO_2$ to allow cells to adhere. The immunotoxins in varying concentrations were added to wells in triplicate. The treated cells were incubated at 37° C. and 5% $CO_2$ for 72 hours. For the final 8 hours of the incubation, [methyl $^3$H]-thymidine (GE Healthcare, UK) was added (1 μCi per well) to each well. Following the incubation, plates were frozen to detach cells and the detached cells were then harvested onto a glass fiber filter, washed, dried, and counted using standard scintillation methods. Background scintillation counts in untreated wells ranged from 73,820±8,499 counts per minute (cpm) to 104,372±11,359 cpm. Due to the inability of PC-3 cells to incorporate $^3$H-thymidine, the effect of DTEGF13 on these cells was analyzed by measuring protein synthesis as indicated by $^3$H-leucine incorporation. Assays measuring $^3$H-leucine uptake differed from $^3$H-thymdine assays only in that they were performed in leucine-free media and incubation with labeled leucine lasted 24 hours, instead of 8 hours. Data from each of these proliferation assays were reported as percentage of control counts.

In several instances, inhibition of cell proliferation was also determined by trypan blue exclusion experimentation. Briefly, cells treated with immunotoxin (as above) or control, non-treated cells were harvested, washed, stained with trypan blue, and counted. A reduced number of cells were obtained from culture wells containing the immunotoxin as compared to the number of cells obtained from wells that did not contain the immunotoxin. In addition, an increase in the amount of cell death (i.e., an increase in the number of trypan blue positive cells) was observed in cells treated with immunotoxin as compared to the amount of cell death in control cells. These results indicated that immunotoxin treatment of cells resulted in cell killing.

Blocking studies were also conducted to test the specificity of DTEGF13. Briefly, anti-EGF or anti-IL13 (R&D Systems, Minneapolis Minn.) antibodies were added to media containing 0.1 nM DTEGF13 at a final concentration of 50 μg/ml. Resulting mixtures were added to wells containing PC-3 or U87 cells. PC-3 cell proliferation was measure by $^3$H-leucine uptake. The mouse leukocyte-specific antibody Ly 5.2 was included as a negative control.

Binding and internalization of radiolabeled ITs. In order to measure the binding and internalization efficiency of DTEGF13, an aliquot of the protein was labeled with $^{111}$In. Briefly, the MX-DTPA 1B4M chelating agent was conjugated to proteins at a 2.5:1 molar ratio using a conjugation buffer consisting of 5 mM sodium bicarbonate, 15 mM sodium chloride, and 0.5 mM EDTA at pH 9.2. Approximately 250 μg of 1B4M-chelated DTEGF13 was labeled with 20 μCi of $^{111}$In with a labeling efficiency >90%. PC-3 cells ($3\times10^5$/tube) were then suspended in 100 μl of RPMI and placed at 4° C. for thirty minutes. 100 µl of 600 nM $^{111}$In-labeled DTEGF13 in ice-cold RPMI was then added to each tube and then cells were incubated for 30 minutes at 4° C. in order to prevent internalization. Following two washes with cold PBS, the cells were resuspended and cultured at 37° C. for specified incubation time periods. Two cell samples were reserved to calculate initially-bound protein. Following incubation periods, cells were pelleted and media was aspirated from each tube. Cells were washed 2× with 500 µl PBS. All incubation media and PBS from washes were pooled for each tube and saved as unbound fraction. PC-3 cells were then washed 2× with RPMI (pH 3.0) to release bound protein and media was saved as bound fraction. Cell pellets were also saved and associated radioactivity was counted as internalized protein. The radioactivity present in all tubes was counted using a gamma counter (Perkin-Elmer, Wellesley Mass.). The percentage of initially bound activity present in each fraction was calculated for each sample.

In vivo efficacy studies of DTEGF13 against PC-3 flank tumors. Male nu/nu mice were purchased from the National Cancer Institute, Frederick Cancer Research and Development Center, Animal Production Area (Frederick, Md.) and housed in an Association for Assessment and Accreditation of Laboratory Animal Care-accredited specific pathogen-free facility under the care of the Department of Research Animal Resources, University of Minnesota. Animal research protocols were approved by the University of Minnesota Institutional Animal Care and Use Committee. All animals were housed in microisolator cages to minimize the potential of contaminating virus transmission.

For flank tumor studies, mice were injected in the left flank with 4×10$^6$ (experiment 1) or 6×10$^6$ (experiment 2) PC-3 cells suspended in 100 µl of a 1:1 RPMI/Matri-Gel mixture. Once palpable tumors had formed (day 18), mice were divided into groups and treated with multiple injections of DTEGF13. All ITs were administered by intratumoral (i.t.) injection using 3/10 cc syringes with 29 gauge needles. All treatments were given in a 100 µl volume of sterile PBS. Tumor size was measured using a digital caliper and volume was determined as a product of length, width, and height.

In vivo efficacy studies of DTEGF13 against PC-3 flank tumors. For flank tumor studies, female nu/nu mice were injected with 6×10$^6$ U87 cells and once tumors reached a size of approximately 200 mm$^3$ (about day 14), mice were divided into groups and treated with either DTEGF13, DTEGF, DTIL13, or DT2222. All immunotoxins were administered by i.t. injection in 100 µl volume of sterile PBS and given on a schedule (see below). Tumor size was measured using a digital caliper, and volume was determined as a product of length, width, and height (as above). Treatment-related toxicity was monitored by measuring animal body weight.

Effect of DTEGF13 chemoilluminescent U87 Flank Tumors. The effect of i.t. administration of DTEGF13 against U87 xenografts was also measured using bioilluminescent imaging. U87/Luc cells stably expressing the firefly luciferase gene were kindly provided by Dr. John Ohlfest (University of Minnesota). U87/Luc cells were identical to parental U87 cells in their growth characteristics and susceptibility to DTEGF13. To initiate the xenografts, female nude mice were injected in the flank with 6×10$^6$ U87/Luc cells in 100 µl PBS. Once tumors had reached a volume of approximately 75 mm$^3$ (day 12), treatment with i.t. administration 2.5 µg DTEGF13 was initiated. Mice were treated with DTEGF13 on day 12, 14, 16, 21, 24, 26, 31, and 33. The treated mice were imaged on day 12 (pretreatment), 17, and 34 to monitor the level of luciferase activity. Images were captured using Xenogen Ivis imaging system and analyzed with Living Image 2.5 software (Xenogen Corporation, Hopkington, Mass.). Prior to imaging, the mice were anesthetized by intraperitoneal administration of a cocktail of 200 µl of a 8 mg/ml ketamine, 1 mg/ml azepromazine, and 0.1 mg/ml butorphanol. All mice received 100 µl of a 30 mg/ml D-luciferin aqueous solution (Gold Biotechnology, St. Louis Mo.) 10 minutes before imaging. All images represent a 10 second exposure time and all regions of interest (ROI) are expressed in units of photons/sec.

Figure 17A:
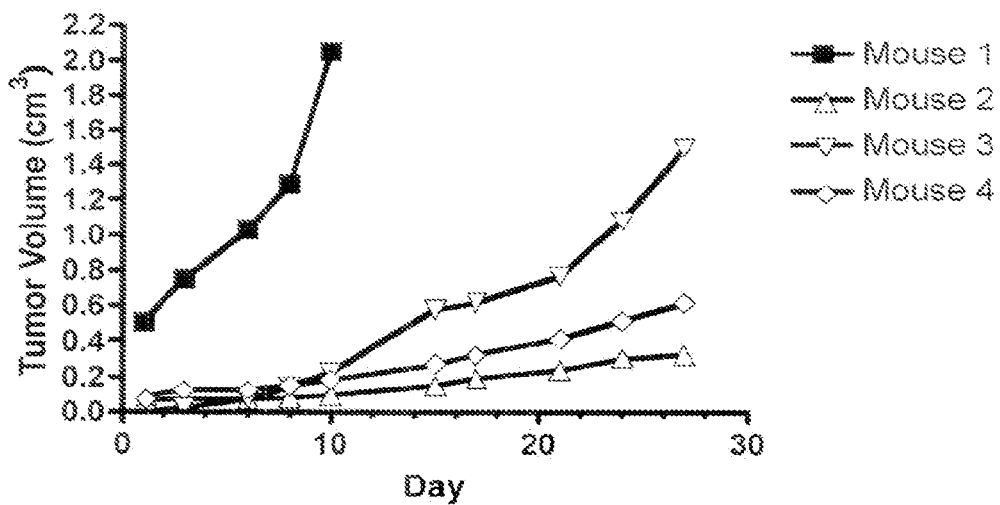
FIGS. 17A and 17B are a pair of line graphs depicting the effect of i.t. injection of DTEGF13 on MIA PaCa-2 flank tumors (Experiment 1). MIA PaCa-2 flank tumors were established by injecting $1 \times 10^7$ MIA PaCa-2 cells into the left flank of male nude mice. Once palpable tumors were established (approximately day 22), the mice were divided into two groups.
Figure 17B:
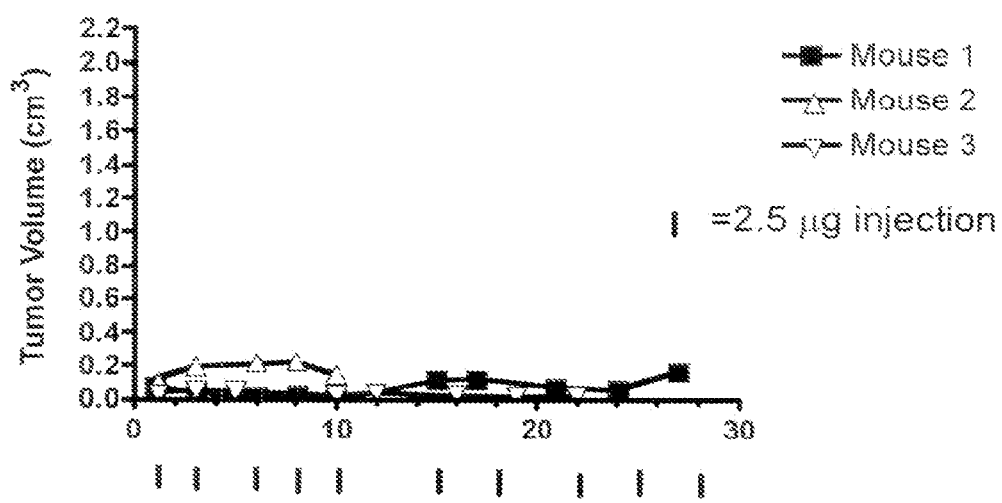

MIAPaCa-2 cell flank tumor model, Experiment 1. Flank tumors were initiated by injecting 1×10$^7$ MIA PaCa-2 cells in DMEM into the left flank of nude mice (n=20). On day 22, mice with palpable tumors were randomized into DTEGF13 treatment or no treatment groups. Treated mice received 2.5 µg DTEGF13 in 100 µl PBS injected i.t. A total of 10 injections were given as often as indicated on graph (FIG. 17B).

MIAPaCa-2 cell flank tumor model, Experiment 2. One day prior to cell injection, male nude mice were irradiated with 300 rad using an X-ray irradiator. Flank tumors were established by injecting 1×10$^7$ MIA PaCa-2 cells in a 1:1 mixture of DMEM and Matrigel (BD Biosciences, San Jose Calif.). When tumors reached approximately 50 mm$^3$ (day 18), mice were divided into groups (n=5/group) and treatment was initiated. Four injections of 2.5 µg DTEGF13, DTEGF, or DTIL13 were given intratumorally every other day (q.o.d.). Mice in the control group received intratumoral injections of 100 µl PBS.

MIAPaCa-2 cell flank tumor model, Experiment 3. For the Experiment 3 flank tumor study, nude mice were injected with 1×10$^7$ MIA PaCa-2 cells in a 1:1 mixture of DMEM and matrigel. On day 15 when flank tumors were approximately 75 mm$^3$, mice were divided into treatment groups (n=6/group). Treatment mice received a total of 6 intratumoral injections of 2.5 µg of either DTEGF13 or the B-cell targeting immunotoxin DT2222. Injections were given three times a week for two weeks.

Statistical analyses. Groupwise comparisons of continuous data were made by Student's t-test. A computer program for compiling life table and statistical analysis by the Log-Rank test was used to analyze survival data. Probability (p) values <0.05 were considered significant.

Example 2

Construction and Purification of DTEGF13

After NcoI/XhoI digestion, the DNA fragment encoding the bispecific IT DTEGF13 was cloned into the pET21d expression vector under control of an isopropyl-β-D-thiogalactopyranoside (IPTG) inducible T7 promoter (FIG. 1). Constructs containing the monospecific IT genes (DTEGF and DTIL13) were also synthesized. DNA sequencing analysis, which was performed by the University of Minnesota Microchemical Facilities (University of Minnesota, Minneapolis, Minn.), confirmed the correctness of the construct sequences. Following purification (as described above), DTEGF was determined to have the predicted molecular weight of 63.6 kDa. All ITs were >95% pure when analyzed by SDS-PAGE.

Example 3

Determining the Ability of DTEGF13 to Kill Prostate and Glioblastoma Cells

Figure 2A:
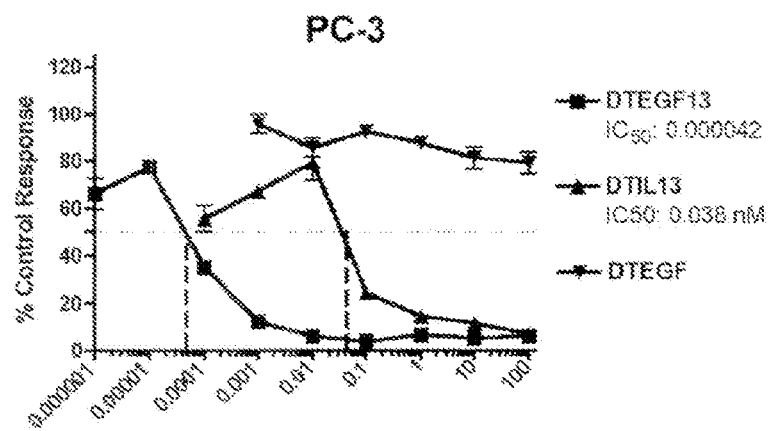
FIG. 2A is a line graph depicting the specific cytotoxicity of DTEGF13 in EGFR+/IL13R+ PC-3 cells as determined by a proliferation assay. DTEGF13, DTIL13, or DTEGF were cultured with PC-3 prostate cancer cells for 72 hours. Data points on the graph represent the mean of triplicate samples±SD. $IC_{50}$ (or inhibitory concentration 50%) is the concentration of the immunotoxin that inhibits 50% of the percent of cell growth in the absence of the immunotoxin. The X-axis represents the concentration of each immunotoxin in nanomolar (nM). The Y-axis represents the % cell growth as compared to control (untreated) cells (% control response).
Figure 2B:
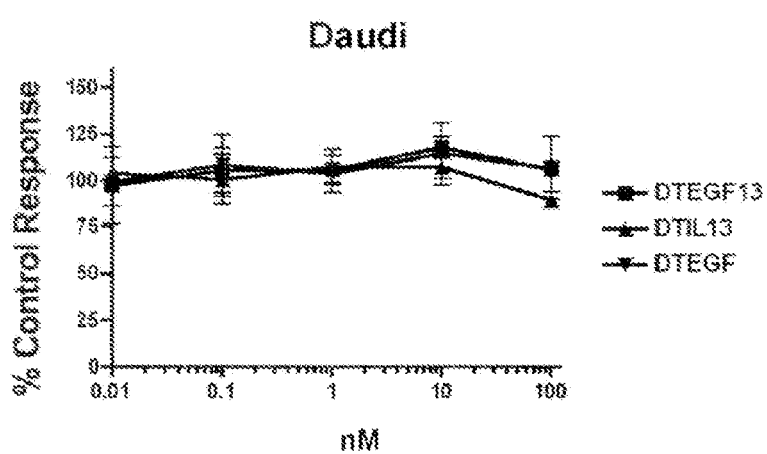
FIG. 2B is a line graph depicting the specific cytotoxicity of DTEGF13 in EGFR−/L13R− Daudi cells as determined by a proliferation assay. DTEGF13, DTIL13, or DTEGF were cultured with Daudi cells for 72 hours. Data points on the graph represent the mean of triplicate samples±SD (standard deviation). The X-axis represents the concentration of each immunotoxin in nM. The Y-axis represents the % cell growth as compared to control (untreated) cells (% control response).

To determine the ability of DTEGF13 to kill epidermal growth factor receptor (EGFR)- and interleukin 13 receptor (IL13R)-expressing carcinoma cells, the EGFR+ and IL13R+ prostate cancer cell line PC-3 was treated with DTEGF13 and inhibition of PC-3 cell growth was measured by a cell proliferation assay. The monospecific DTIL13 was able to kill PC-3 cells with an $IC_{50}$ of 0.038 nM (FIG. 2A). The monospecific immunotoxin DTEGF was much less effective in killing PC-3 cells with only 20% inhibition of growth at 100 nm. However, the bispecific cytotoxin (CT) DTEGF13 showed an $IC_{50}$ of 0.042 pM, representing a 905-fold increase in activity as compared to DTIL13 and at least a 7 log increase in activity as compared to DTEGF. DTEGF13 and the monospecific ITs exhibited minimal cell growth inhibition of the EGF13R and IL13R negative cell line Daudi (FIG. 2B).

Figure 3:
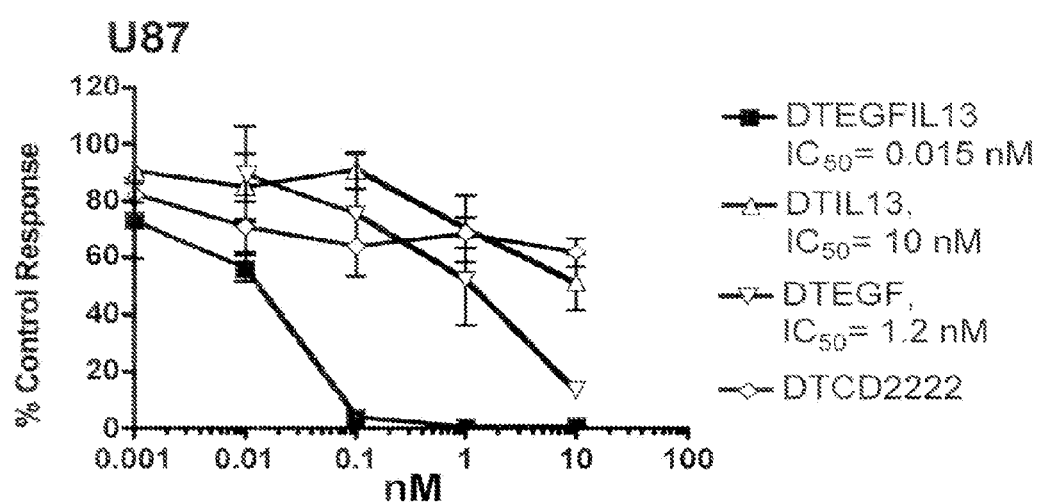
FIG. 3 is a line graph depicting the specific cytotoxicity of DTEGF13 in EGFR+/IL13R+ U87 cells as determined by a proliferation assay. DTEGF13, DTIL13, or DTEGF were cultured with U87 cells for 72 hours. Data points on the graph represent the mean of triplicate samples±SD. The X-axis represents the concentration of each immunotoxin in nM. The Y-axis represents the % cell growth as compared to control (untreated) cells (% control response).

The DTEGF13 was also tested against the EGFR+ and IL13R+ glioblastoma cell line U87 MG. FIG. 3 shows that the monospecific DTEGF was able to kill U87 cells with an $IC_{50}$ of 1.2 nM. Monospecific DTIL13 was less effective with an $IC_{50}$ of 10 nM. However, DTEGF13 showed an $IC_{50}$ of 0.015 nM, representing a 80-fold increase in activity as compared to DTEGF and a 665-fold increase in activity as compared to DTIL13. DTEGF13 showed minimal activity against the EGF13R-IL13R-B lymphoma cell line Daudi and the T cell leukemia lines Jurkat and CEM.

An EGF13 protein devoid of $DT_{390}$ was also synthesized (see above) with a purity of greater than 95%. As much as 1,000 nM of the EGF13 protein added to PC-3 cells or U87 cells was not inhibitory, indicating that the EGF13 moiety, by itself, had no anti-cancer activity.

Example 4

Figure 4:
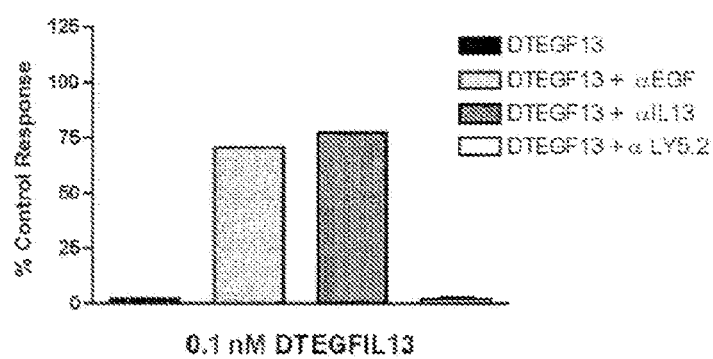
FIG. 4 is a bar graph depicting the ability of anti-EGF and anti-IL13 antibodies to block the inhibition of PC-3 cell growth by DTEGF13 as determined by a proliferation assay. DTEGF13 (0.1 nM) was cultured with PC-3 cells for 72 hours in the presence or absence of an anti-EGF antibody, an anti-IL13 antibody, or a control antibody (Ly5.2). The X-axis represents each experimental test. The Y-axis represents the % cell growth as compared to control (untreated) cells (% control response).

Determining the Ability of Anti-EGF and Anti-IL13 Antibodies or EGF13 to Block DTEGF13-Induced Killing To confirm that EGF and IL13 were both important for DTEGF13-induced killing of PC-3 cells, a blocking experiment was performed. 50 μg/ml of anti-EGF or anti-IL13 antibodies were tested for their ability to block the killing of PC-3 cells by DTEGF13 (FIG. 4). When added to 0.1 nM DTEGF13, both antibodies were capable of blocking about 70-80% of the anti-proliferative effect, but neither of the antibodies when added singly completely blocked DTEGF13-induced PC-3 killing, likely because the monospecific blocking agents could only block one ligand, leaving the other free. Blocking with both antibodies resulted in 100% blocking. In contrast, the addition of control anti-mouse Ly5.2 antibodies had no blocking effect. Similar results were obtained using U87 MG cells (FIG. 2C).

Taken together, these data indicated that both ligands (EGF and IL13) were important for the activity of the DTEGF13 molecule.

To determine whether a non-immunotoxic form of the DTEGF13 receptor-targeting reagent was capable of reducing DTEGF13-induced killing of MiaPaCa-2 human pancreatic cancer cells in vitro, a blocking experiment was performed. Cells were contacted with various concentrations of DTEGF13 in the presence of 1 nM, 10 nM, 100 nM, or 1000 nM EGF13, or without EGF13 as a control. The results of the experiment demonstrated that EGF13 (a non-immunotoxic receptor-targeting reagent) was effective to reduce DTEGF13-induced killing of MiaPaCa-2 cells.

Example 5

Determining the ability of DTEGF13 to Kill the Prostate Cell Line DU-145 and the Glioblastoma Cell Line U118

Figure 5:
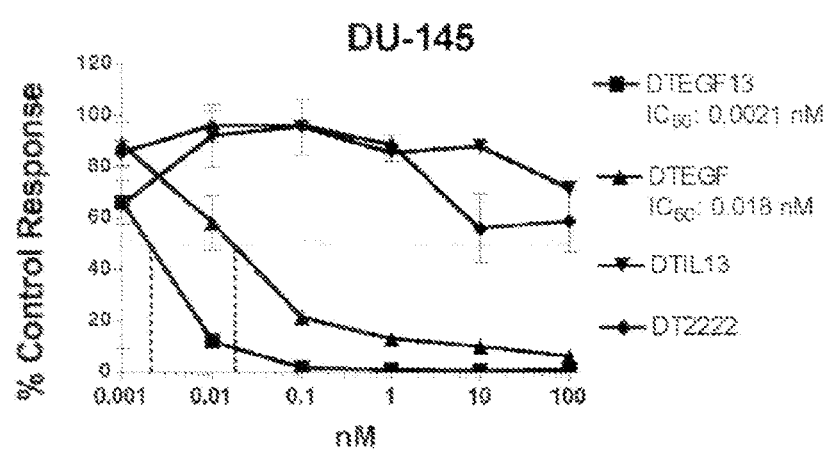
FIG. 5 is a line graph depicting the specific cytotoxicity of DTEGF13 in EGFR+/IL13R+ DU-145 cells as determined by a proliferation assay. DTEGF13, DTIL13, or DTEGF were cultured with DU-145 cells for 72 hours. Data points on the graph represent the mean of triplicate samples±SD. The X-axis represents the concentration of each immunotoxin in nM. The Y-axis represents the % cell growth as compared to control (untreated) cells (% control response).

DTEGF13 was tested against a second prostate cancer cell line, DU-145. The monospecific DTIL13 exhibited low killing activity against DU-145 cells having an $IC_{50}$ of greater than 100 nM (FIG. 5). The monospecific immunotoxin DTEGF, an $IC_{50}$ of 0.018 nM, was more effective than DTIL13. However, the DTEGF was incapable of entirely inhibiting the DU-145 response, even at 100 nM. In contrast DTEGF13 ($IC_{50}$ of 0.0021 nM) entirely inhibited the DU-145 response at 0.1 nM. DT2222, a negative control IT, was substantially less inhibitory. Similar findings with the DTEGF13 and monospecific ITs were observed with the LNCaP-derived C4-2 prostate cancer cell line.

Figure 6:
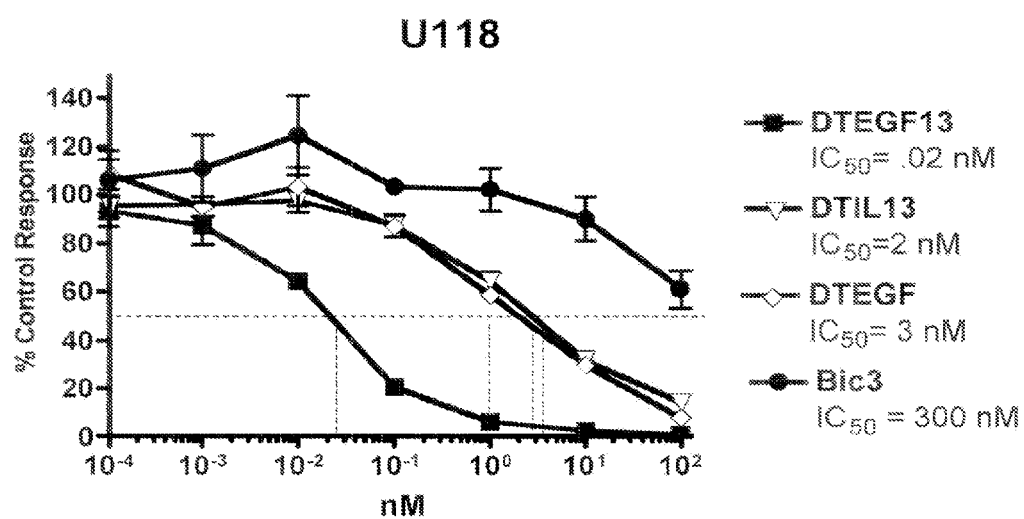
FIG. 6 is a line graph depicting the specific cytotoxicity of DTEGF13 in $EGFR^+/IL13R^+$ U118 cells as determined by a proliferation assay. DTEGF13, DTIL13, DTEGF, or Bic3 (a control) were cultured with U118 cells for 72 hours. Data points on the graph represent the mean of triplicate samples±SD. The X-axis represents the concentration of each immunotoxin in nM. The Y-axis represents the % cell growth as compared to control (untreated) cells (% control response).

DTEGF13 was tested against a second glioblastoma cell line, U118. FIG. 6 shows that, against U-118 cells, monospecific DTIL13 showed an $IC_{50}$ of 2 nM. Monospecific DTEGF showed an $IC_{50}$ of 3 nM. In contrast, DTEGF13 had an $IC_{50}$ of 0.02 nM against U118 cells, an increase of at least 100-fold. Bic3, a negative control IT was less inhibitory and showed an $IC_{50}$ of >300 nM.

Similar results were obtained from experiments using the PANC-1 (DTEGF13 $IC_{50}$ of 0.035 nM), SW-1990 (DTEGF13 $IC_{50}$ of 0.00013 nM), and ASPC-1 (DTEGF13 $IC_{50}$ of 0.052 nM) human pancreatic cancer cell lines.

Together, these cell line data indicated that BITs combining an EGF ligand and an IL13 ligand on a single chain molecule increased the immunotoxic potency against a number of different prostate cancer lines compared to either monospecific ITs.

Example 6

Figure 7:
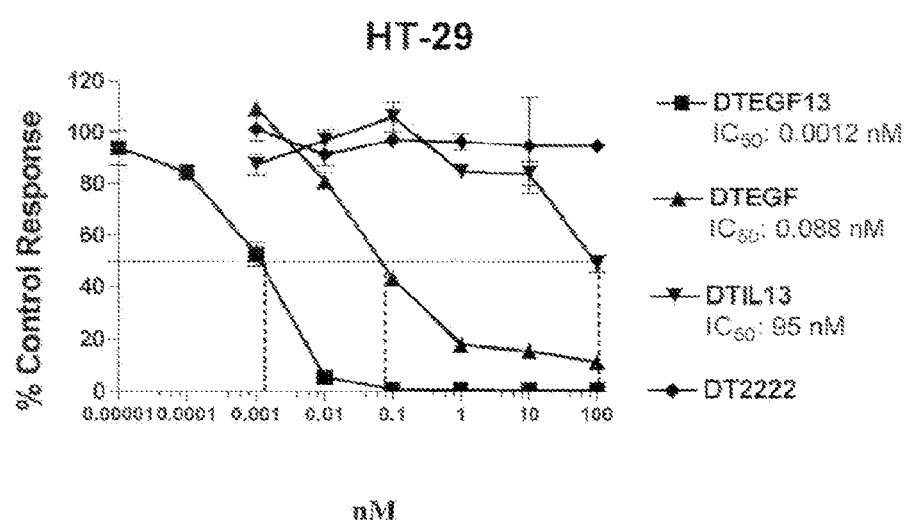
FIG. 7 is a line graph depicting the specific cytotoxicity of DTEGF13 in $EGFR^+/IL13R^+$ HT-29 cells as determined by a proliferation assay. DTEGF13, DTIL13, DTEGF, or DT222 (a negative control) were cultured with HT-29 cells for 72 hours. Data points on the graph represent the mean of triplicate samples±SD. The X-axis represents the concentration of each immunotoxin in nM. The Y-axis represents the % cell growth as compared to control (untreated) cells (% control response).

Selective Cytotoxicity of DTEGF13 Against HT-29 Human Colorectal Cancer Cells and Calu-3 Human Lung Adenocarcinoma Cells To determine the cytotoxic efficacy of DTEGF13 against HT-29 human colorectal cancer cells, the cells were treated with DTEGF13, DTEGF, or DTIL13 and the effect of the immunotoxins on their growth was measured (as above). DTEGF13 was highly active against the HT-29 human colorectal cancer cell line (FIG. 7). As in the case of DU-145, DTIL13 was less effective than DTEGF13, having an $IC_{50}$ of 95 nM. DTEGF13 was more effective with an $IC_{50}$ of 0.088 nM. DTEGF13 was more active than either of the monospecific ITs with an $IC_{50}$ of 0.0012 nM. In this experiment, the negative control DT2222 had no effect on HT-29 cell growth.

Figure 8:
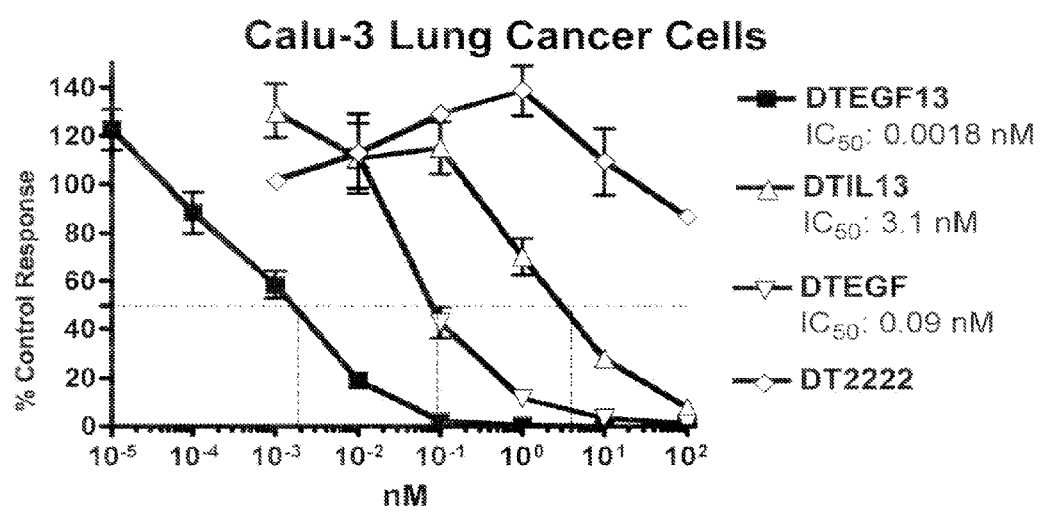
FIG. 8 is a line graph depicting the specific cytotoxicity of DTEGF13 in $EGFR^+/IL13R^+$ Calu-3 cells as determined by a proliferation assay. DTEGF13, DTIL13, DTEGF, or DT222 (a control) were cultured with Calu-3 cells for 72 hours. Data points on the graph represent the mean of triplicate samples±SD. The X-axis represents the concentration of each immunotoxin in nM. The Y-axis represents the % cell growth as compared to control (untreated) cells (% control response).

In Calu-3 cells, DTEGF13 was also more effective than DTEGF or DTIL13, exhibiting an $IC_{50}$ of 0.0018 nM (FIG. 8). DTEGF showed an $IC_{50}$ of 0.09 nM and DTIL13-showed an $IC_{50}$ of 3.1 nM (the negative control had minimal effect).

Together, these results demonstrate that DTEGF13 is also more effective against other forms of carcinoma than its monomeric counterparts.

Example 7

Figure 9:
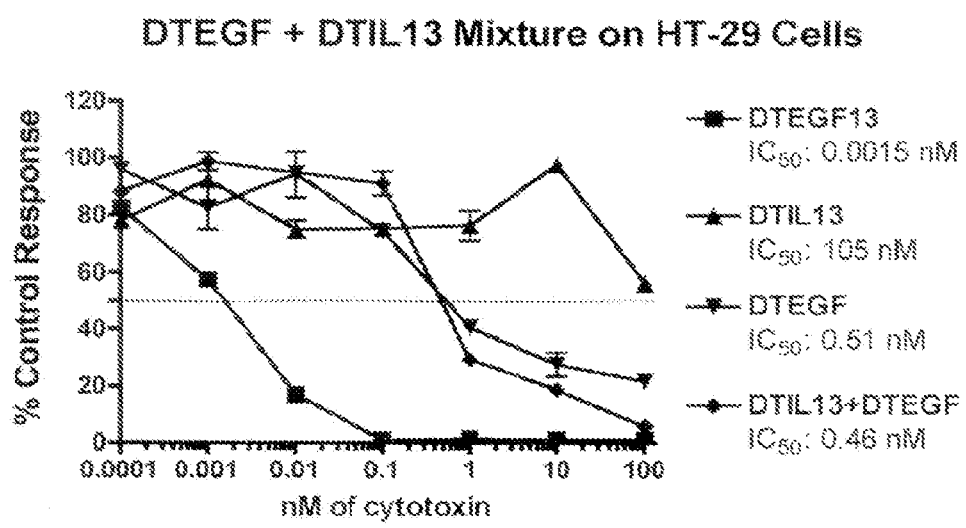
FIG. 9 is a line graph depicting the cytotoxicity of the bispecific DTEGF13 immunotoxin compared to a mixture of DTEGF and DTIL13 monospecific immunotoxins. The mixture is such that a 1 nM solution is 0.5 nM DTEGF and 0.5 nM DTIL13. DTEGF13, DTIL13, DTEGF, or DTEGF and DTIL13 were cultured with HT-29 cells for 72 hours. Data points on the graph represent the mean of triplicate samples±SD. The X-axis represents the concentration of each immunotoxin in nM. The Y-axis represents the % cell growth as compared to control (untreated) cells (% control response).

Increased Activity of DTEGF13 is Due the Presence of EGF and IL13 Ligands on a Single Molecule To determine if the increased activity of DTEGF13 was due to the presence of its two different ligands, proliferation assays were performed comparing HT-29 cells treated with DTEGF13 to HT-29 cells treated with a mixture of monomeric DTEGF and DTIL13 (or each individual monomeric form). This mixture of monospecific immunotoxins included a 1:1 number of binding molecules equivalent to the number of binding molecules on single chain DTEGF13. The mixture of DTEGF and DTIL13 exhibited the same cytoxic effect on HT-29 cells as the DTEGF alone (FIG. 9). In contrast, the DTEGF13 molecule had an $IC_{50}$ of 0.0015 nM, which was 307-fold more potent than the $IC_{50}$ of the DTEGF and DTIL13 mixture.

Figure 10:
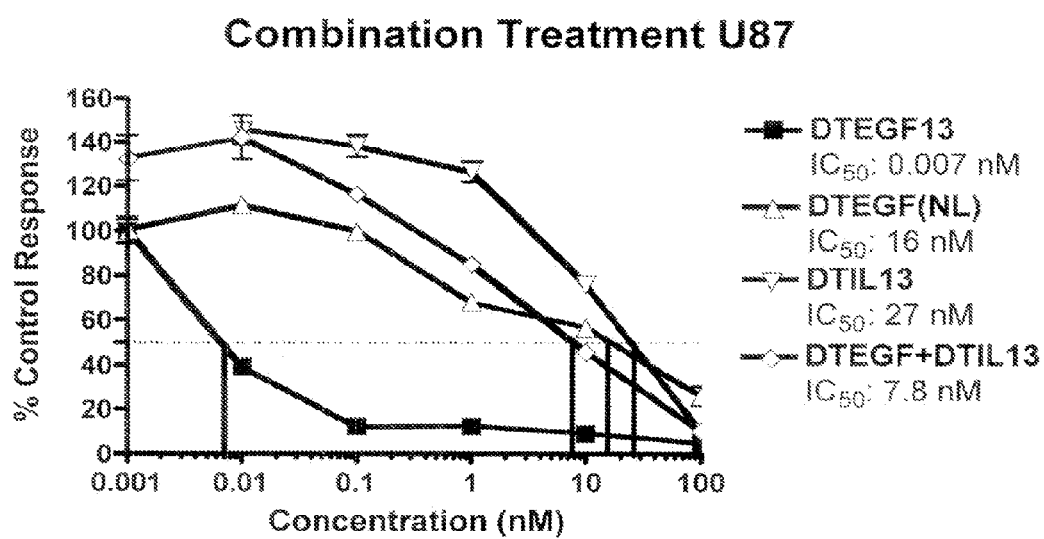
FIG. 10 is a line graph depicting the cytotoxicity of the bispecific DTEGF13 immunotoxin compared to a mixture of DTEGF and DTIL13 monospecific immunotoxins DTEGF13, DTIL13, DTEGF, or DTEGF and DTIL13 were cultured with U87 cells for 72 hours. Data points on the graph represent the mean of triplicate samples±SD. The X-axis represents the concentration of each immunotoxin in nM. The Y-axis represents the % cell growth as compared to control (untreated) cells (% control response).

Similar experiments were also carried out using U87 cells, wherein proliferation assays were performed comparing U87 cells treated with DTEGF13 to U87 cells treated with a mixture of monomeric DTEGF and DTIL13 (or each individual monomeric form). This mixture of monospecific immunotoxins also included a 1:1 number of binding molecules equivalent to the number of binding molecules on single chain DTEGF13. The mixture of DTEGF and DTIL13 exhibited the same cytotoxic effect on U87 cells as the DTEGF alone (FIG. 10). In contrast, the DTEGF13 molecule had an $IC_{50}$ of 0.007 nM, which was over 1000-fold more potent than the $IC_{50}$ of the DTEGF and DTIL13 mixture.

Similar results were also obtained from experiments using MIAPaCa-2 human pancreatic cancer cells and H2981-T3 human lung cancer cells.

These data demonstrate that the increased activity observed with DTEGF13 is, in large part, due to the presence of the two different ligands in DTEGF13.

Example 8

Binding and Internalization of DTEGF13

Figure 11:
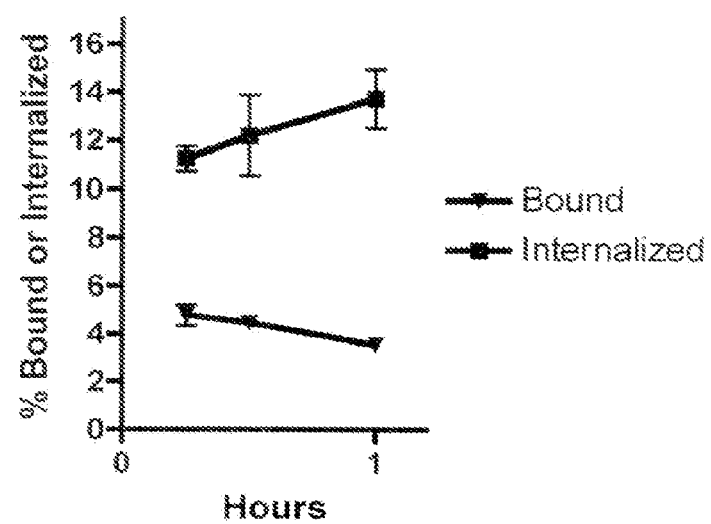
FIG. 11 is a line graph depicting the binding and internalization of DTEGF13 by PC-3 cells. PC-3 cells were incubated with $^{111}$In-labeled DTEGF13 for various times (X-axis). Data are presented as percentage of initially bound protein in each fraction (Y-axis). Each data point represents the sample mean±SD.

In order to measure the binding and internalization of DTEGF13, DTEGF13 was radiolabeled-labeled with $^{111}$In and incubated with PC-3 cells or U87 MG cells for varying amounts of time from 0 to 2 hours. Following the incubation, the bound fraction of each protein was preferentially released, and all remaining radioactivity associated with the cells was considered to be the result of internalized DTEGF13. The amount of the bound and internalized fractions of labeled DTEGF13 over a one hour period for PC-3 cells is shown in FIG. 11 (similar results obtained for U87 MG cells). The binding of DTEGF13 decreased as the immunotoxin was internalized by the cells. Similar results were also observed for the monomeric immunotoxin molecules DTEGF and DTIL13.

Example 9

DTEGF13 in Intratumoral Nude Mouse Flank Tumor Models

Figure 12A:
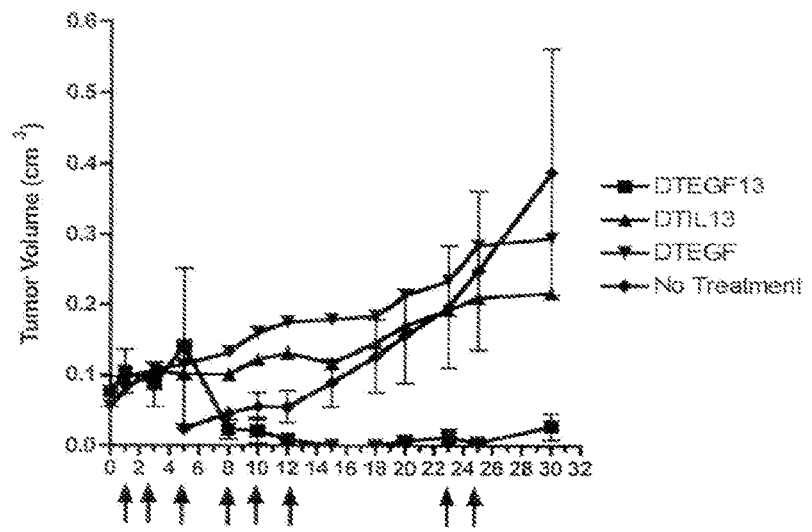
FIG. 12A is a line graph depicting the effect of DTEGF13 treatment on tumor growth using a PC-3 prostate tumor mouse model. Nude mice bearing PC-3 flank tumors were treated intra-tumorally (i.t.) with DTEGF13, DTIL13, or DTEGF (n=4–5/treatment group). The mean tumor volumes of mice are shown in each treatment group. The arrows under the abscissa indicate days of injection.

PC-3 flank tumor model. To test the ability of DTEGF13 to inhibit tumor growth in vivo, PC-3 cells were injected into the left flank of nude mice in two separate experiments. Once the tumors were established and palpable, mice were treated with multiple i.t. injections of DTEGF13. DTEGF13 was studied in a mouse model because the human EGF and IL13 (of DTEGF13) binds to mouse EGFR and IL13R, respectively. FIG. 12A shows the mean tumor volume data from the first experiment in which groups of mice (n=4–5/group) were given i.t. injections (2.5 µg/injection) of either DTEGF13, DTEGF, DTIL13, or untreated on days 1, 3, 5, 8, 10, 12, 23, 25. The multiple injections of DTEGF13 were significantly effective in preventing tumor growth compared to the untreated controls until injections were halted on day 25. On day 29, in DTEGF13 treated mice, tumors had reoccurred in 2 of 4 mice and were undetectable in 2 of 4 mice. DTEGF and DTIL13 treated tumors grew at a similar rate to the untreated control tumors and thus had no significant inhibitory affect.

Figure 12B:
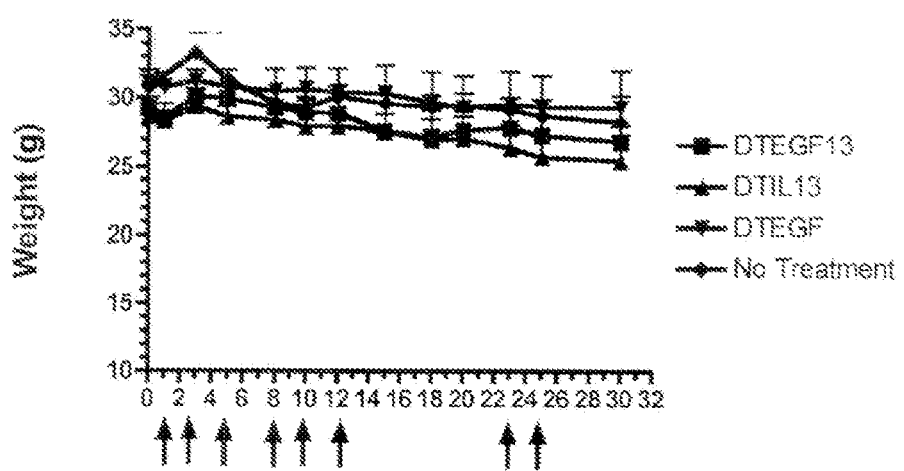
FIG. 12B is a line graph depicting the effect of DTEGF13 treatment on weight loss using a PC-3 prostate tumor mouse model. Nude mice bearing PC-3 flank tumors were treated i.t. with DTEGF13, DTIL13, or DTEGF (n=4–5/treatment group). The mean weights of the mice are shown in each treatment group. The arrows under the abscissa indicate days of injection.

Weight loss is frequently used in cytotoxin (CT) and immunotoxin (IT) studies as an indication of toxicity. FIG. 12B shows that weight loss resulting from the DTEGF13 treatment at the termination of the experiment after the multiple doses did not exceed 10% of the pre-treatment weight. Thus, this dosage of DTEGF13 was tolerated.

Figure 13:
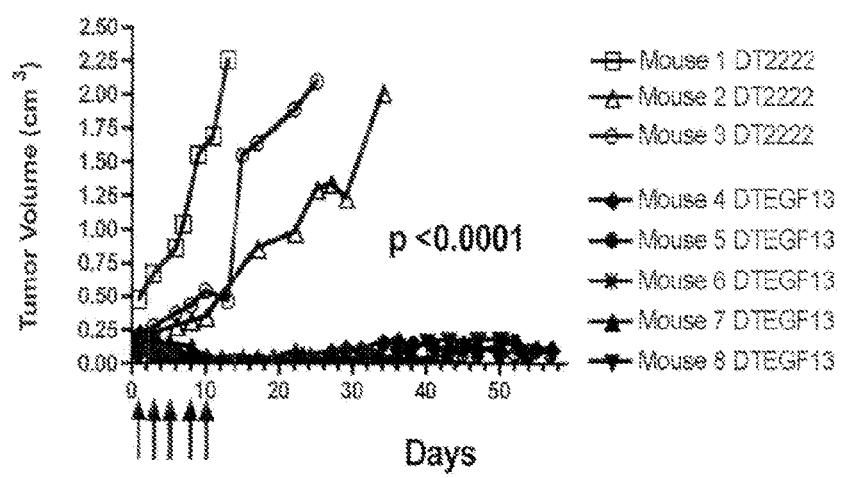
FIG. 13 is a line graph depicting the effect of DTEGF13 treatment on tumor growth using a PC-3 prostate tumor mouse model. Nude mice bearing PC-3 flank tumors received five i.t. 2.5 injections of DTEGF13 or DT222 (n=4–5/treatment group). The arrows under the abscissa indicate days of injection. The growth of individual tumors is plotted over time.

In a second experiment, established PC-3 tumors were treated every other day (q.o.d.) between days 1 and 10 (total of 5 injections) with i.t. injections of DTEGF13 or negative control DT2222 (FIG. 13). Tumor volumes are shown for individual treated mice. Tumors treated with DT2222 continued to escalate in size despite treatment. In contrast, treatment with DTEGF13 in 5 of 5 mice, inhibited tumor growth and kept the tumor growth in check even on day 57, despite the fact that treatments were stopped on day 10. Differences in the tumor volumes between the DT2222 treated mice and DTEGF13-treated mice were significant (p<0.0001). There was no significant weight loss in DTEGF13-treated mice.

Figure 14:
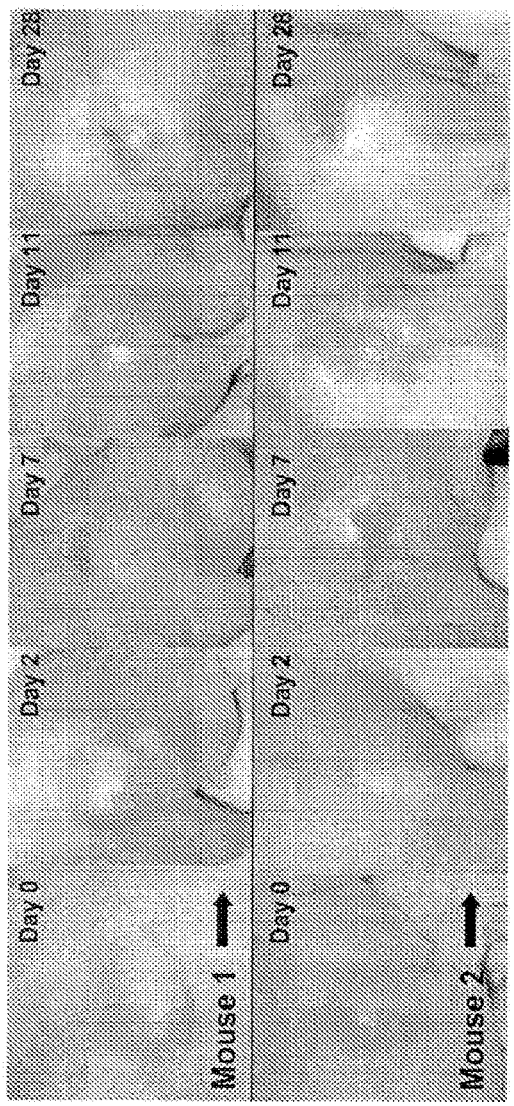
FIG. 14 is a series of photographs depicting the regression of PC-3 flank tumors treated with DTEGF13. Two female nude mice having palpable PC-3 flank tumors were each treated with i.t. injections of DTEGF13. The progressive effect on the tumor volume over time is shown in the photographs. Mouse 1 was injected a total of 9 times between day 0 and day 28, whereas Mouse 2 was injected 5 times (every other day; q.o.d.) between days 0 and 10.

In an independent study, the tumors of two mice receiving multiple DTEGF13 treatments were photographed at various times after treatment (FIG. 14). Animals received 5 injections into their tumors (which were about 0.2 cm3) over a 10-day interval. The tumor on mouse 1 regressed more slowly showing slight signs of ulceration as early as day 2. By day 28, it shrunk about 80% of its original tumor size. By day 47 it was entirely undetectable. The tumor on mouse 2 shrunk more quickly. Tumor size was reduced 100% by day 10. This tumor recurred 20 days later.

Figure 15A:
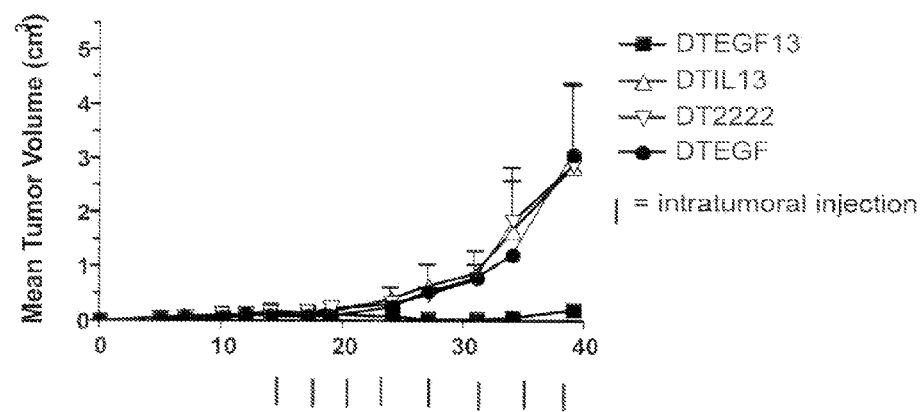
FIG. 15A is a line graph depicting the effect of DTEGF13 treatment on tumor growth using a U87 tumor mouse model. Nude mice bearing U87 flank tumors were treated i.t. with DTEGF13, DTIL13, or DTEGF (n=5/treatment group). The mean tumor volumes of mice are shown in each treatment group. The lines under the abscissa indicate days of injection.

U87 flank tumor model. To further test the ability of DTEGF13 to inhibit tumor growth in vivo, U87 cells were injected into the flank of nude mice. Once the tumors reached a volume of about 0.2 cm$^3$, mice were treated with multiple i.t. injections of DTEGF13 as described above. FIG. 15A shows mean tumor volume data from the first experiment in which groups of mice (n=5/group) were given injections (2.5 µg/injection) of either DTEGF13, DTEGF, DTIL13, or DT2222 on day 14, 17 20, 24, 27, 31, 34, and 38. The multiple injections of DTEGF13 were significantly effective in preventing tumor growth compared to the DT2222 negative controls (p<0.04 on days 27 and 31). DTEGF and DTIL13 treated tumors grew at a similar rate to the DT2222-treated control tumors and thus had no significant inhibitory affect.

Figure 15B:
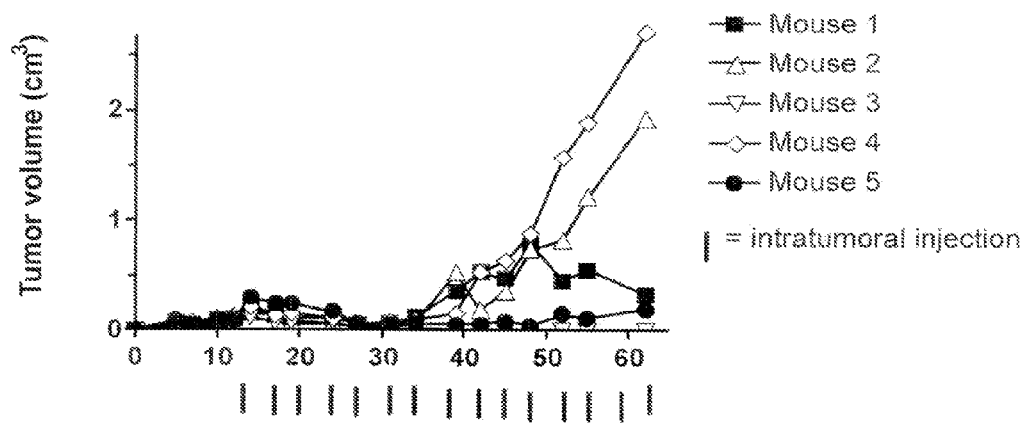
FIG. 15B is a line graph depicting the long-term effect of DTEGF13 treatment on tumor growth using a U87 tumor mouse model. Nude mice bearing U87 flank tumors were treated i.t. with DTEGF13, DTIL13, or DTEGF. The lines under the abscissa indicate days of injection. The growth of individual tumors is plotted over time.

In FIG. 15B, the individual mouse data is plotted for the DTEGF13 group. Following day 38, two of five tumors relapsed and grew through treatment. Three of five tumors continued to respond to additional DTEGF13 treatment until day 62 when the experiment was terminated.

Figure 15C:
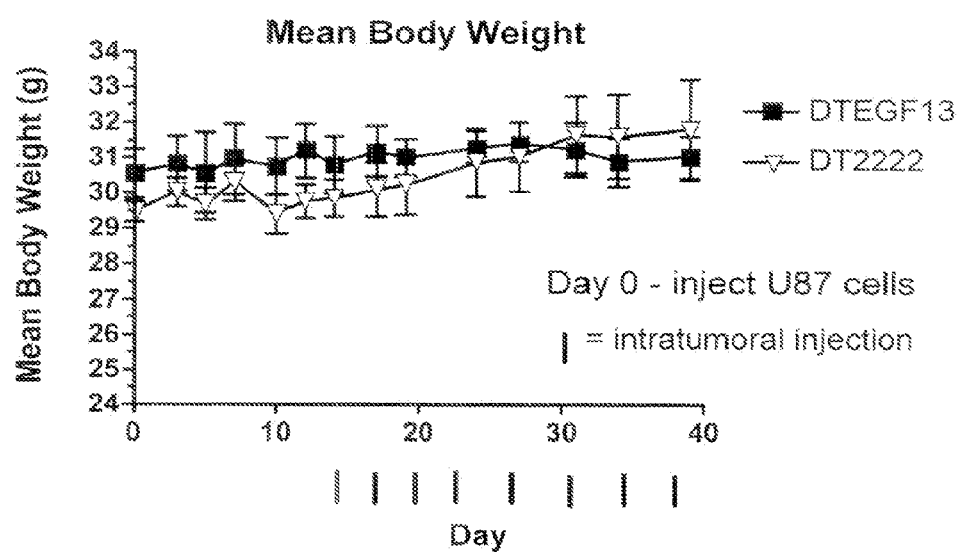
FIG. 15C is a line graph depicting the effect of DTEGF13 treatment on weight loss using a U87 tumor mouse model. Nude mice bearing U87 flank tumors were treated i.t. with DTEGF13 or DT2222 (n=4–5/treatment group). The mean weights of the mice are shown in each treatment group. The lines under the abscissa indicate days of injection.

Weight loss associated with DTEGF13 treatment was not a significant problem in these studies and the DTEGF13 treatment dosage was tolerated (FIG. 15C).

In a second experiment, DTEGF13 was tested against U87 cells stably expressing the firefly luciferase gene. The cells (U87/luc) showed a similar response to DTEGF13 in vitro. Cells were injected into the flank of athymic nude mice. Once tumors were established and palpable (day 12), each of the four mice were imaged for luciferase activity. Treatments were begun on day 12 and mice were treated on days 12, 14, 16, 21, 24, 26, 31, and 33. Three patterns of response were noted. In pattern one, tumors fully regressed in mouse 1 and 3 imaged on days 17 and 34, respectively. In mouse 4, tumor growth slowed, but the tumor did not regress. In mouse 5, tumor regressed by day 17, but then reappeared on day 34.

Together, these studies using two different tumor models showed that in a model in which the human EGF and IL13 of DTEGF13 is cross-reactive with mouse EGF and IL13, DTEGF13 is a highly effective anti-tumor agent. These findings also showed that the agent is highly active in its action against prostate cancer and glioblastoma and that the positioning of both EGF and IL13 moieties on the same molecule contributes to its superior anti-tumor effect.

Example 10

Figure 16:
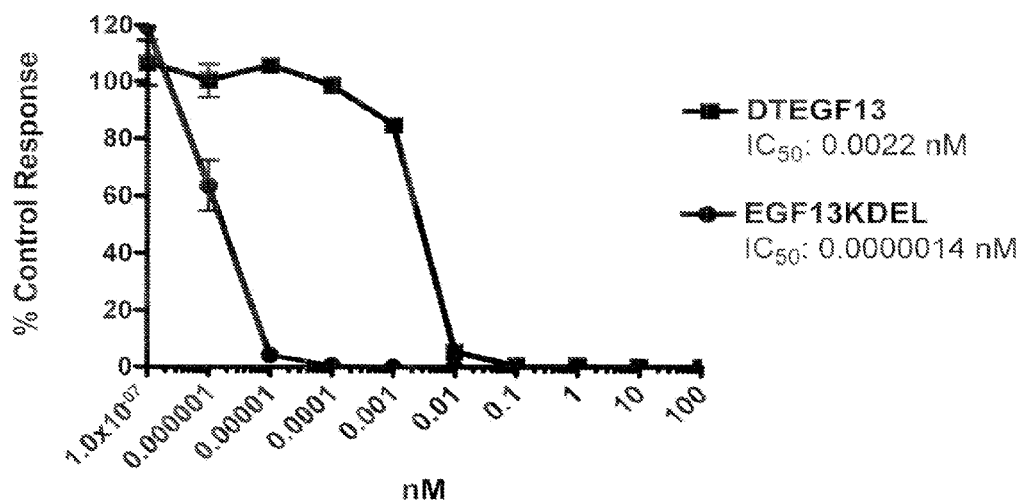
FIG. 16 is a line graph depicting cytotoxic effect of DTEGF13 and EGF13 KDEL on MIAPaCa-2 cells in culture. DTEGF13 or EGF13 KDEL were cultured with MIAPaCa-2 cells for 72 hours. Data points on the graph represent the mean of triplicate samples±SD. The X-axis represents the concentration of each immunotoxin in nM. The Y-axis represents the % cell growth as compared to control (untreated) cells.

Effect of DTEGF13 and EGF13 KDEL on MIAPaCa-2 Pancreatic Adenocarcinoma Tumor Cells To determine whether other toxin moieties would work as effectively as $DT_{390}$ in the EGF13 immunotoxin, the nucleic acid sequence of the $DT_{390}$ moiety was removed from EGF13 coding sequence and a nucleic acid sequence encoding the with the *Pseudomonas* exotoxin A KDEL sequence was added to the 3' end of the EGF13 moiety using standard molecular biology techniques. MiaPaCa-2 pancreatic adenocarcinoma tumor cells were treated with either DTEGF13 or EGFKDEL at various concentrations for 72 hours. Cell proliferation was measured after 72 hours by $^3$H-thymidine incorporation and reported as percentage of control cells (FIG. 16). The EGF13 KDEL immunotoxin exhibited an $IC_{50}$ value of 0.0000014 nM as compared to DTEGF13 with an $IC_{50}$ value of 0.0022 nM. These data indicate that additional toxic domains are effective in immunotoxic EGF13 compositions.

Example 11

DTEGF13 in a MIA PaCa-2 Intratumoral Nude Mouse Flank Tumor Model

To test the ability of DTEGF13 to inhibit pancreatic tumor growth in vivo, human MIA PaCa-2 cells were xenografted into the flank of nude mice. Once the tumors were established and palpable, mice were treated with multiple i.t. injections of DTEGF13 as described above. For Experiment 1 shown in FIG. 17 (FIGS. 17A and 17B), $1 \times 10^7$ tumor cells suspended in DMEM were injected into the flanks of mice that had not been subjected to total body irradiation (TBI). This method yielded poor tumor establishment rates (<40% of injected animals). Three of the animals that developed tumors were given an aggressive course of 10 injections of DTEGF13 over the course of three weeks. In this experiment, control tumor growth was slower than desired in most animals (FIG. 17A). However, DTEGF13 treatment was effective at blocking tumor growth over the duration of the study (FIG. 17B).

Figure 17C:
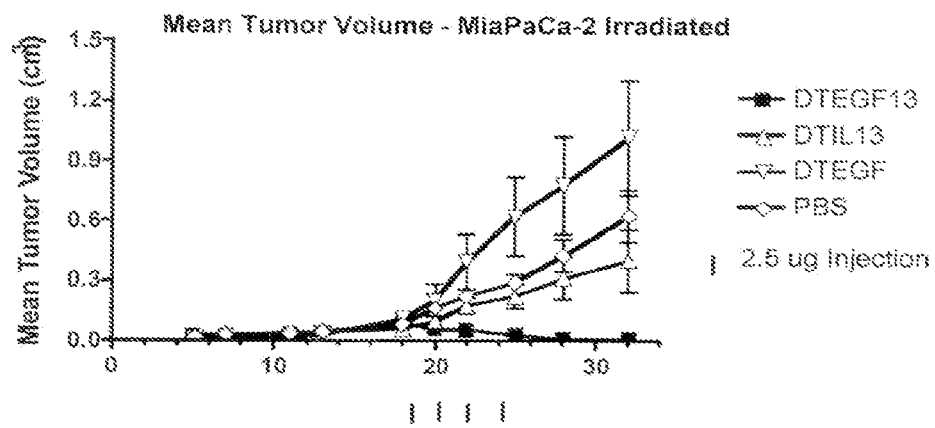
FIGS. 17C, 17D, and 17E are a series of line graphs depicting the effect of i.t. injection of DTEGF13 on MIA PaCa-2 flank tumors in Experiment 2. Prior to injection of tumor cells, male nude mice were irradiated with 300 Rad (Radiation Absorbed Dose) using an x-ray irradiator. Flank tumors were then established by injecting $1 \times 10^7$ MIA PaCa-2 cells in a 1:1 mixture of DMEM:matrigel. When tumors reached approximately 50 mm$^3$, mice were divided into groups and treated with i.t. injections of 2.5 µg DTEGF13, DTIL13, DTEGF, or PBS. Four injections were given q.o.d. as indicated by lines under each graph.
Figure 17D:
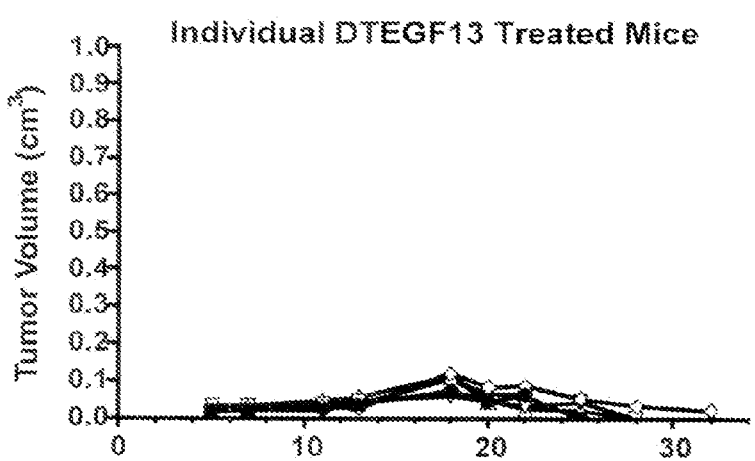
Figure 17E:
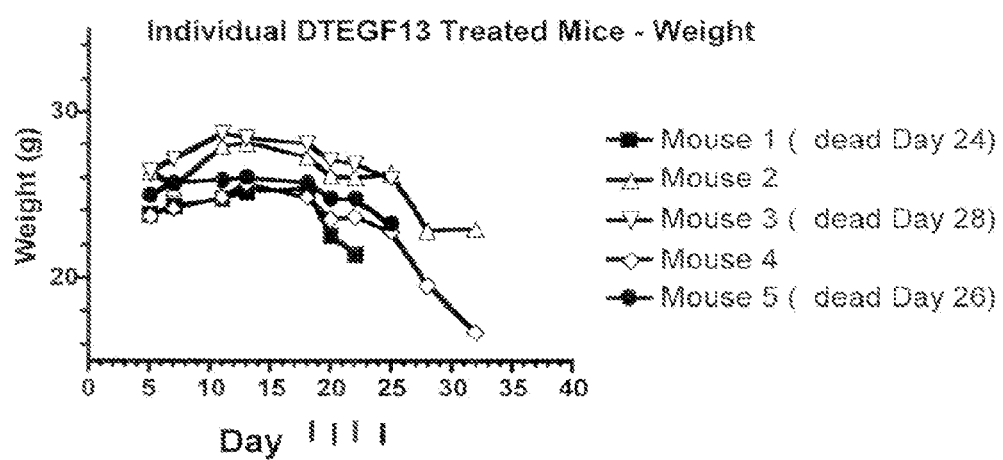

In Experiment 2, animals were exposed to 300 Rad (Radiation Absorbed Dose) TBI one day prior to the injection of $1 \times 10^7$ MIA PaCa-2 cells. Cells were injected in a 1:1 mixture of DMEM and Matrigel in order to promote better tumor growth. The combination of TBI and Matrigel increased the tumor take rate to >95%. At day 18 post-tumor implantation, experimental mice received four i.t. injections of 2.5 μg of either DTEGF13, DTEGF, or DTIL13 given q.o.d., whereas the control mice received i.t. injections of PBS on the same schedule. FIG. 17C shows that the highest degree of anti-tumor efficacy was achieved with DTEGF13 administration and FIG. 17D shows the tumor volumes of the individual animals in the DTEGF13 treatment group. Each of the animals showed a noticeable decrease in tumor volume with one tumor completely regressing. However, treatment-related toxicity was heightened by the total body irradiation given to the animals in this experiment (FIG. 17E). Weight loss and mortality (⅗ animals) occurred despite following a previously well-tolerated treatment regimen.

Figure 18A:
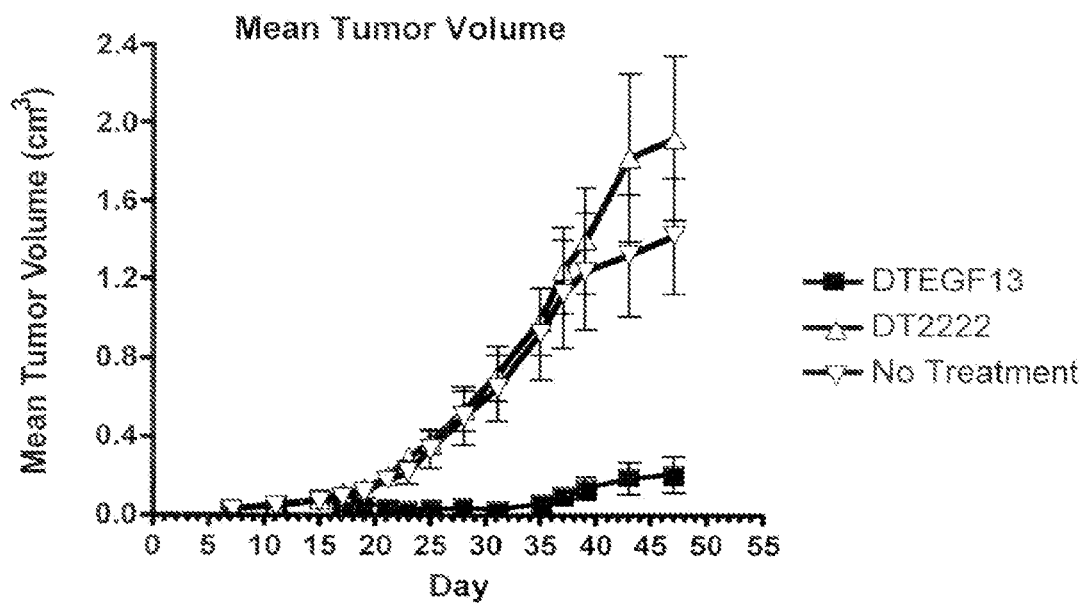
FIGS. 18A and 18B are a pair of line graphs depicting the effect of i.t. administration of DTEGF13 on MIA PaCa-2 flank tumors (Experiment 3).
Figure 18B:
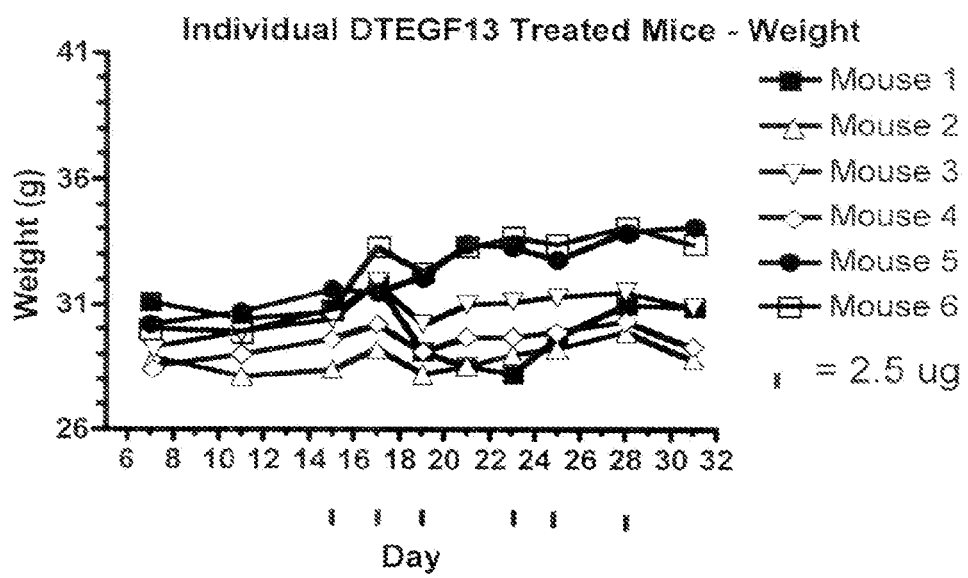
Figure 19A:
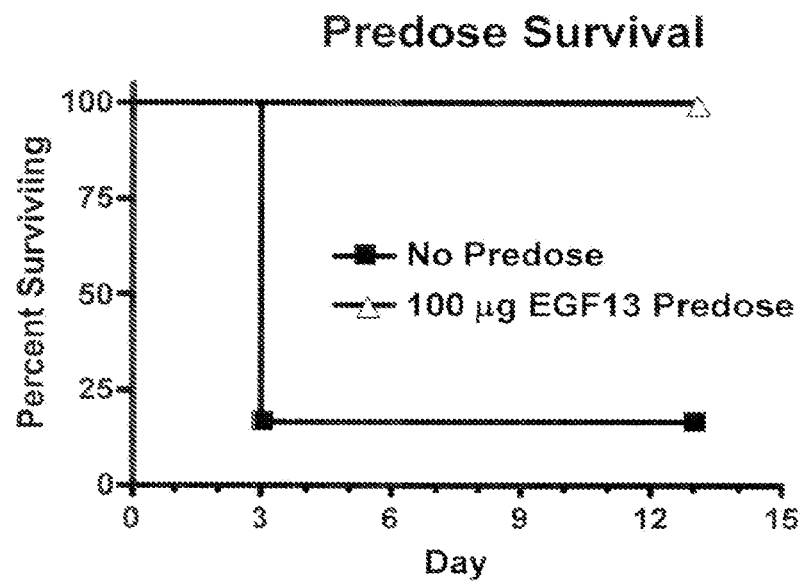
FIG. 19A is a Kaplan-Meier plot depicting the protective effect of a EGF13 predose on the survival of mice administered a lethal dose of DTEGF13. Normal C57BL/6 mice (n=6/group) were administered a 100 µg predose of EGF13 protein or a control, followed immediately by a lethal dose (5 µg i.p.) of DTEGF13. The controls received no EGF13 protein. The Y-axis represents % survival and the X-axis represents the number of days post-administration of the lethal dose.
Figure 19B:
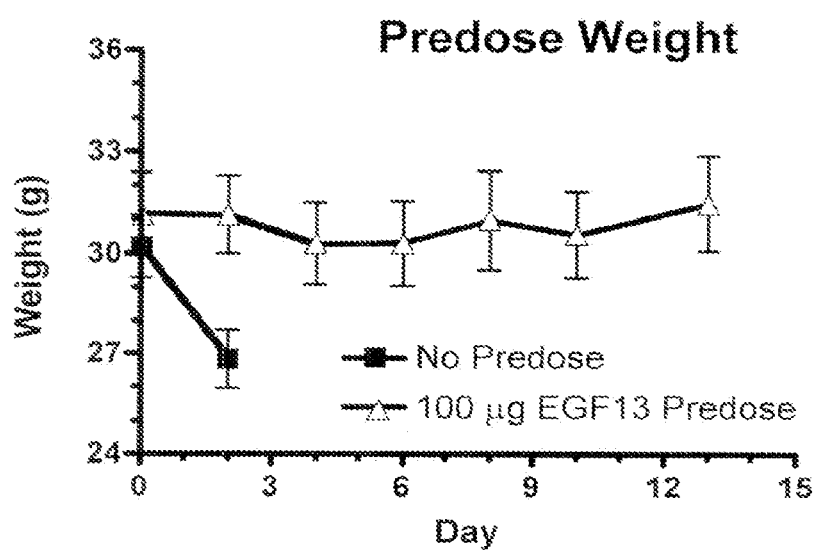
FIG. 19B is a line graph depicting the protective effect of a EGF13 predose on the weight loss of mice administered a lethal dose of DTEGF13. Normal tein were injected into the spleen of mice and at day 61 post injection, the mice were sacrificed and organs removed. Each panel shows an organ (identified by name) with and without bioluminescent imaging. All images represent a 30 second exposure time and all regions of interest (ROI) are expressed in units of photons/sec/cm2/sr. The number shown below the bioluminescent image represents the photons/second/cm2/sr measured for each of the organs. Images were captured using Xenogen IVIS™ imaging system (University of Minnesota) and analyzed with Living Image 2.5.
Figure 20:
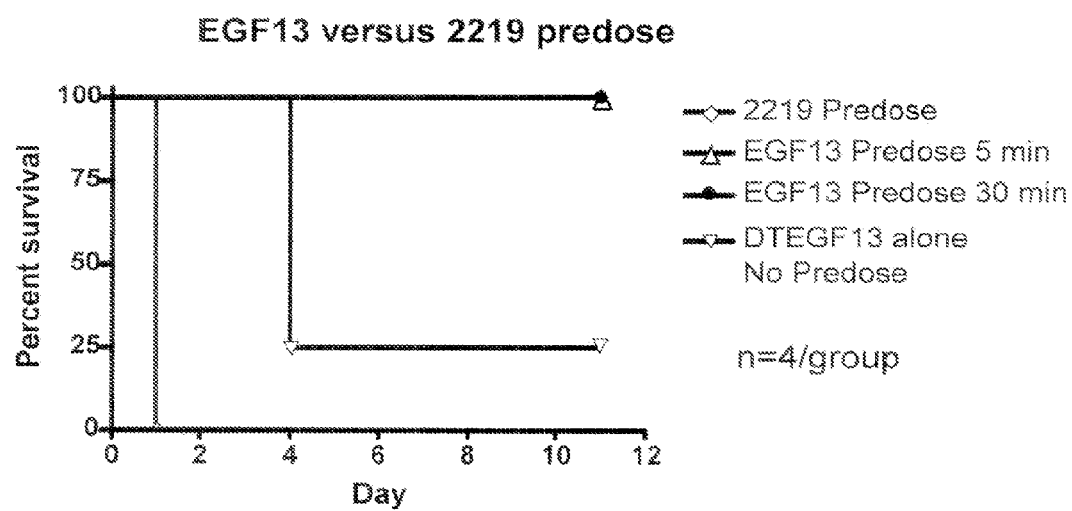

For Experiment 3, non-irradiated mice were injected subcutaneously in the left flank with $1 \times 10^7$ MIA PaCa-2 cells suspended in 100 μl of a 1:1 mixture of DMEM and Matrigel. This method facilitated 100% tumor establishment without introducing the unwanted side effects related to TBI. FIG. 18A shows significant anti-tumor effect of DTEGF13 as compared to the tumor progression observed in groups of mice the were untreated or were treated with the negative control DT2222. Tumor growth in the mice was inhibited by DTEGF13 treatment, but some relapses did occur following cessation of DTEGF13 treatment. A course of 6 i.t. injections of 2.5 μg DTEGF13 was tolerated with no significant toxicity as evidenced by animal weight (FIG. 18B).

Together, these studies show that in a model in which the human EGF and IL-13 of DTEGF13 are cross-reactive with mouse EGFR and IL-13R, DTEGF13 is a highly effective anti-tumor agent. The reagent is highly effective against human pancreatic cancer and that both EGF and IL-13 moieties present in the same molecule contribute to its superior anti-tumor effect.

Example 12

Pre-Dosing EGF13 Protects Mice from Lethal DTEGF13 Dose

Figure 21A:
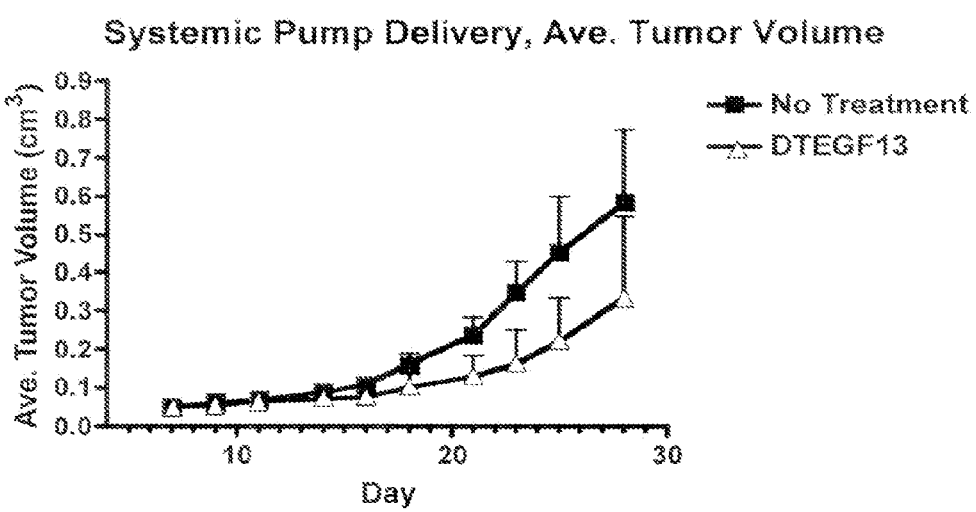
Figure 21B:
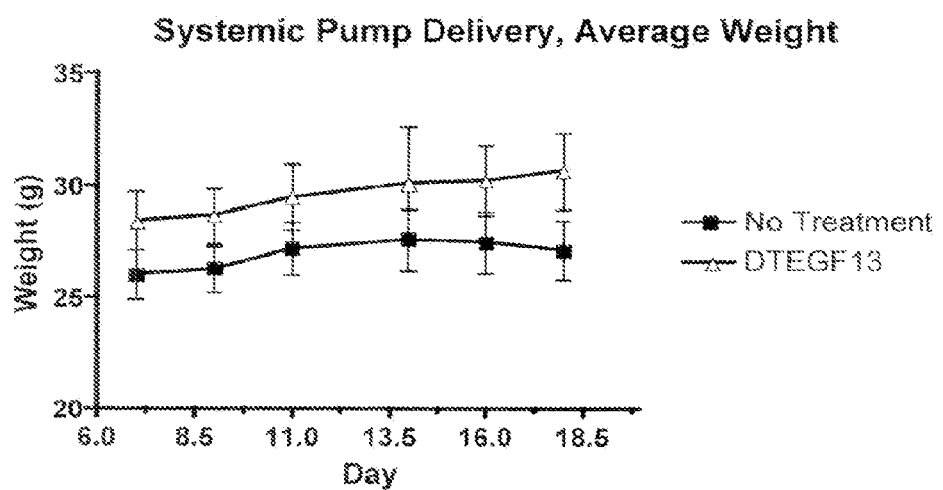

To determine whether administering an EGF13 polypeptide without an DT390 toxic domain could protect mice from a lethal dose of DTEGF13, normal mice were predosed intraperitoneally (i.p.) with EGF13 (or a control saline solution) and then i.p. administered a lethal dose of DTEGF13 (5 μg). The weight and survival of each animal was monitored over a 13 day period (FIG. 19). 80% of the control mice receiving no EGF13 predose prior to the lethal dose of DTEGF13 exhibited weight loss and died by day 3 (FIG. 19A). In contrast, none of the mice given the predose of EGF13 exhibited substantial weight loss and all of these mice survived to day 13 of the study (FIG. 19B). These results indicate that a predose of EGF13 protects mice against a lethal challenge of DTEGF13.

To determine whether the timing of a predose of the EGF13 is important for its protective effect of mice against a lethal dose of DTEGF13, normal mice were administered a predose of EGF13 (or a control protein "2219") either 5 minutes or 30 minutes prior to the administration of the DTEGF13. The "2219" protein consisted of an sFv immunoglobulin fragment specific for CD22 protein bound to an sFv immunoglobulin fragment specific for CD19 protein. This protein was not capable of recognizing the EGF receptor or the IL13 receptor and thus served as a control for these studies. The predose protected all of the animals regardless of the timing. Almost all of the control mice given unreactive 2219 protein or no predose died by day 5. In contrast, all of the mice predosed at 5 or 30 minutes prior to DTEGF13 administration survived to day 11 of the study (FIG. 20). These results indicate that the timing of the predose does not substantially affect its protective effect against a lethal dose of DTEGF13.

Example 13

Delivery of DTEGF13 to Mice Using a Systemic Pump

To determine the efficacy of delivering the DTEGF13 immunotoxin by systemic pump on tumor growth in mice, $10^7$ MIAPaca-2 cells in a 1:1 mixture of cells:matrigel were administered to male nude mice flank. On day 11 post tumor injection, Alzet 1007D osmotic pumps were implanted near the right scapulas (opposite the left flank tumors) and used to deliver to the mice 50 μg DTEGF13 (or vehicle control). Tumor growth in the mice was measured with digital calipers. As shown in FIG. 21A, systemic pump delivery of DTEGF13 reduced the average tumor volume in treated mice as compared to no treatment. Systemic pump-delivered DTEGF13 did not result in weight loss in the treated animals (FIG. 21B).

Example 14

Efficacy of DTEGF13 in a U87 (Glioblastoma) Tumor Model in Rats

Figure 22A:
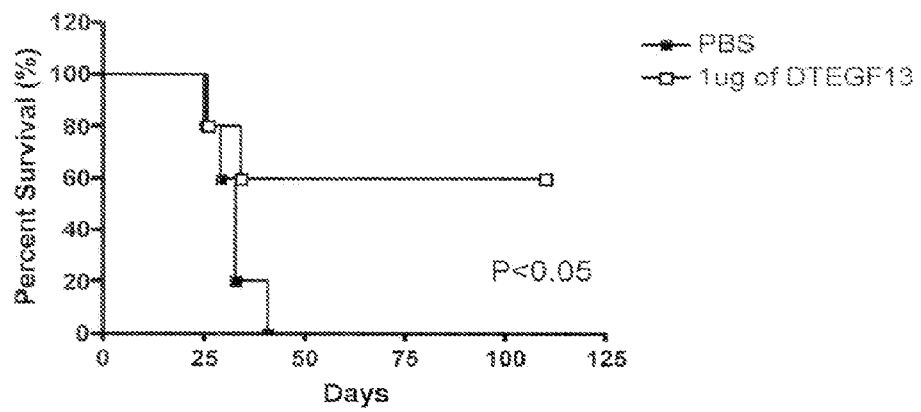
Figure 22B:
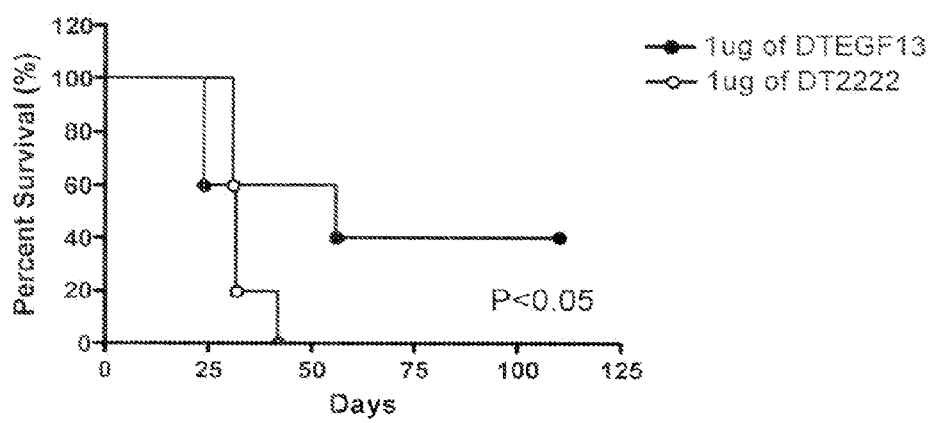
Figure 22C:
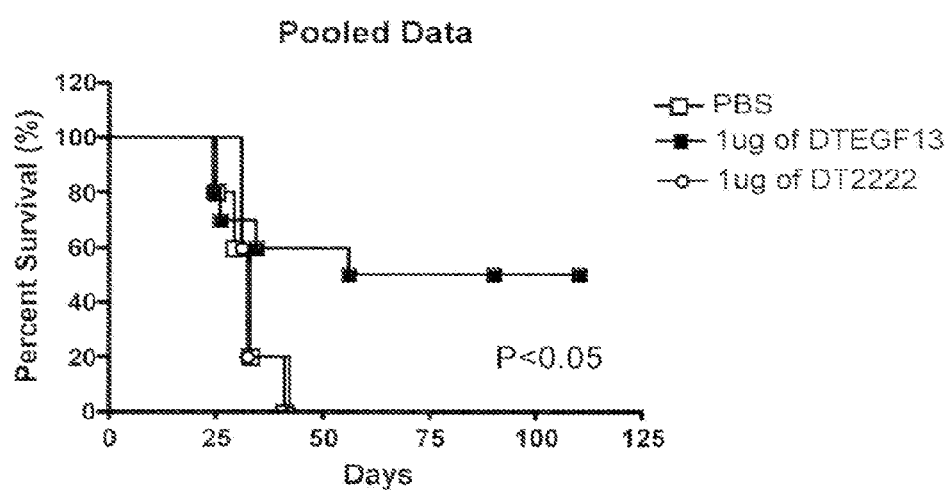

To test the ability of DTEGF13 to inhibit glioblastoma growth in vivo, human U87-luc cells (U87 glioblastoma cells stably expressing a nucleic acid encoding a luciferase protein) were injected intracranially into athymic nude rats. DTEGF13 (totaling 1 µg) was injected intracranially by microinfusion pump into a group of the rats (N=5) bearing U87-luc tumors at day 8 and 15 post tumor injection. Three of five of the treated rats showed complete tumor regression as compared to a group of 5 control rats receiving a placebo (phosphate buffered saline; PBS) that all died by day 42 (FIGS. 22A and 22C). In addition, minimal weight loss was detected after injection of DTEGF13, indicating that the compound is well tolerated in the rats. The human EGF and IL13 in the DTEGF13 compound do bind to mouse EGFR and IL13R, demonstrating the on-target effect of DTEGF13 in the rat model.

In a second experiment, human U87-luc cells (U87 glioblastoma cells stably expressing a nucleic acid encoding a luciferase protein) were injected intracranially into athymic nude rats. DTEGF13 (totaling 1 µg) was injected intracranially by microinfusion pump into a group of the rats (N=5) bearing U87-luc tumors at day 8 and 15 post tumor injection. In this case, 2 of 5 of the rats treated with DTEGF13 showed complete tumor regression. There was one rat, which exhibited initial regression with a later relapse. Four of five control rats receiving DT2222 (described above) control immunotoxin died by day 42 (FIGS. 22B and 22C).

These results demonstrated that DTEGF13 can inhibit, and in some cases lead to complete regression of, human glioblastoma growth in vivo.

Example 15

Determining the Maximum Tolerated Dose and Evaluating Toxicity of DTEGF13

Figure 23:
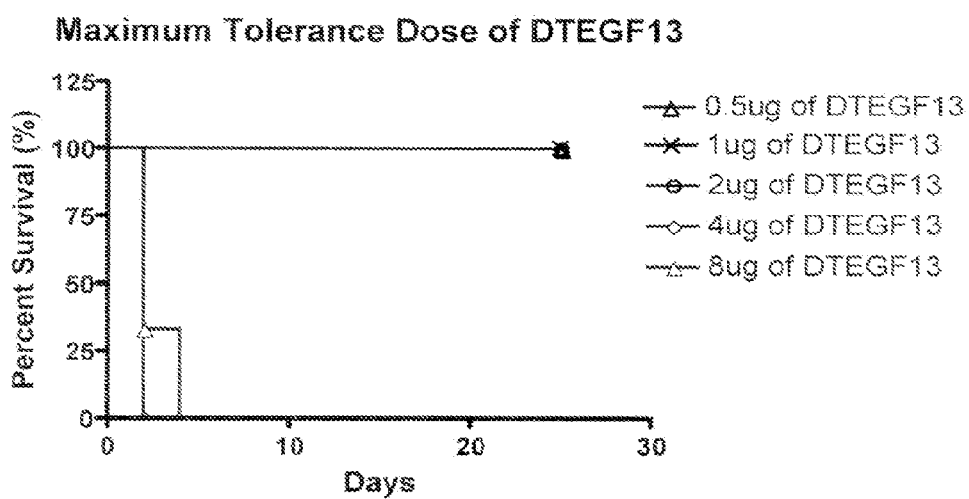

To determine the maximum tolerated dose (MTD) of DTEGF13 in rats, normal rats (n=3/group) were injected intracranially with various concentrations (0.5, 1, 2, 4, and 8 µg) of DTEGF13 or PBS as a control on day 0 and day 7. Physical appearance of and behavioral changes in the animals were monitored daily. A survival curve is shown in FIG. 23. The results of this experiment indicated that the MTD for intracranial injection of DTEGF13 in rats is 1 µg/injection.

Figure 24A:
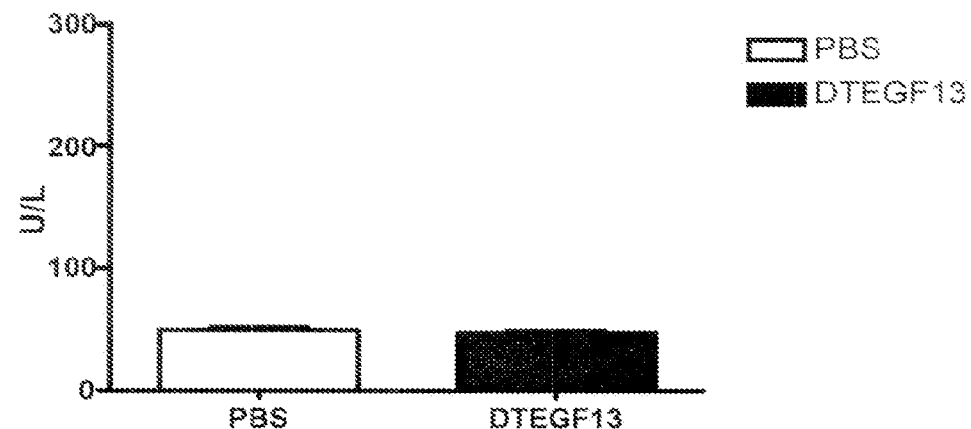
Figure 24B:
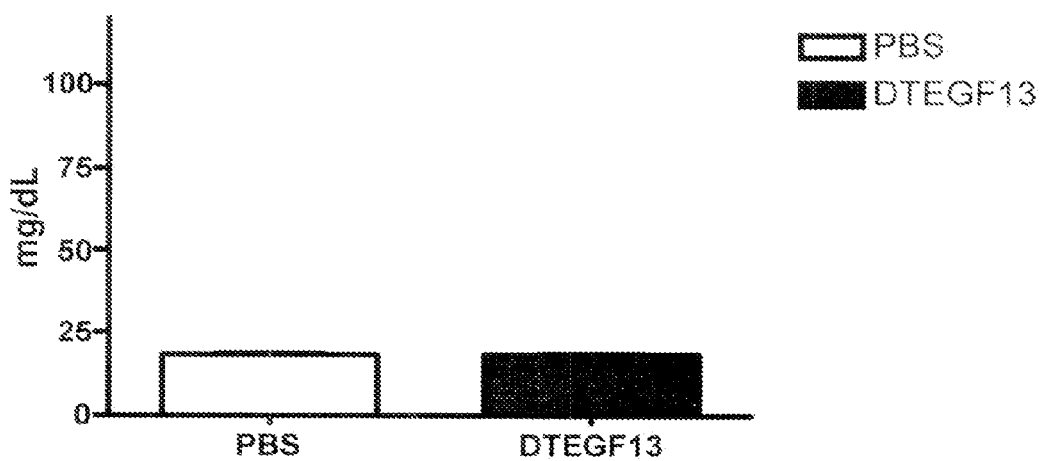

To determine if the DTEGF13 compound exhibits any liver or kidney toxicity in the rat model, normal rats (n=5/group) were injected intracranially with 1 µg of DTEGF13 or with PBS as a control on day 0 and 7. Any liver damage resulting from the DTEGF13 treatment was monitored by measuring alanine aminotransferase (ALT) levels and kidney damage was monitored by measuring blood urea nitrogen (BUN) levels in normal rats (N=5/group) as described in, e.g., Rustamzadeh et al. (2006) *Int. J. Cancer* 120:411-419. On the 21$^{st}$ and 14$^{th}$ day after the last injection, blood was collected from each of the rats (facial vein) and analyzed. There were no significant differences observed in ALT (FIG. 24A) or BUN (FIG. 24B) levels between PBS and DTEGF13 treated group, as compared to the control group, indicating that this dose was not only effective in treating tumors, but did not result in toxicity to critical organ systems.

It is understood that similar analyses can be performed in other pre-clinical test animals (e.g., mice, rabbits, guinea pigs, pigs, dogs, cats, or non-human primates) and for other routes of administrations (e.g., systemic administration) in the establishment of efficacy and/or safety parameters for use of any of the receptor-targeting reagents described herein in human subjects.

Example 16

Figure 25A:
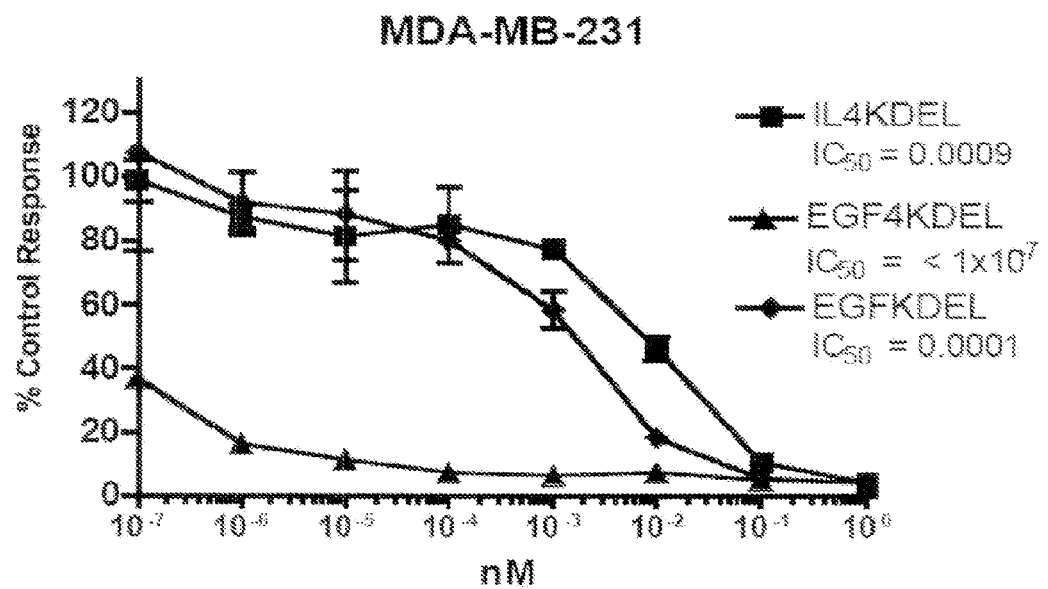

Determining the Ability of EGF4 KDEL to Kill MDA-MB-231 Human Breast Cancer Cells To determine whether bispecific immunotoxins containing EGF and IL-4 also exhibit enhanced tumor cytotoxicity, a nucleic acid encoding a fusion protein (EGF4KDEL) containing EGF, IL-4, and a biologically active fragment of *Pseudomonas* exotoxin/KDEL sequence (referred to as "KDEL" in the construct nomenclature) was constructed (using techniques as described above; the amino acid sequence for the EGFKDEL molecule is depicted in SEQ ID NO:19). The EGF4KDEL immunotoxin was tested for efficacy in killing MDA-MB-231 human breast cancer cells. The cells were treated with various concentrations of EGF4KDEL, IL4KDEL, and EGFKDEL and the effect of the immunotoxins on their growth was measured (as above; see FIG. 25A). EGF4KDEL was highly effective at killing the breast cancer cells having an IC50 of less than 1×10-7 as compared to an IC50 of 0.0009 for the monospecific IL4KDEL reagent and an 1050 of 0.0001 for the monospecific EGFKDEL reagent. Similar results were also obtained for a number of other human breast cancer cell lines including, e.g., MCF-7 cells (IC50 of 0.004 nM), SKBR3 cells (IC50 of 0.03 nM), and BT474 cells (IC50 of 0.002 nM). Similar results were also obtained for U87 cells, U118 cells, MiaPaCa-2 cells, PC-3 cells. SW1990 cells, and HT29 cells, indicating that the EGF4KDEL immunotoxin, like the DTEGF13 immunotoxin, is broadly effective in a wide range of human cancer cells including those of breast, lung, pancreatic, prostate, and colon cancer as well as glioblastoma cells.

Figure 25B:
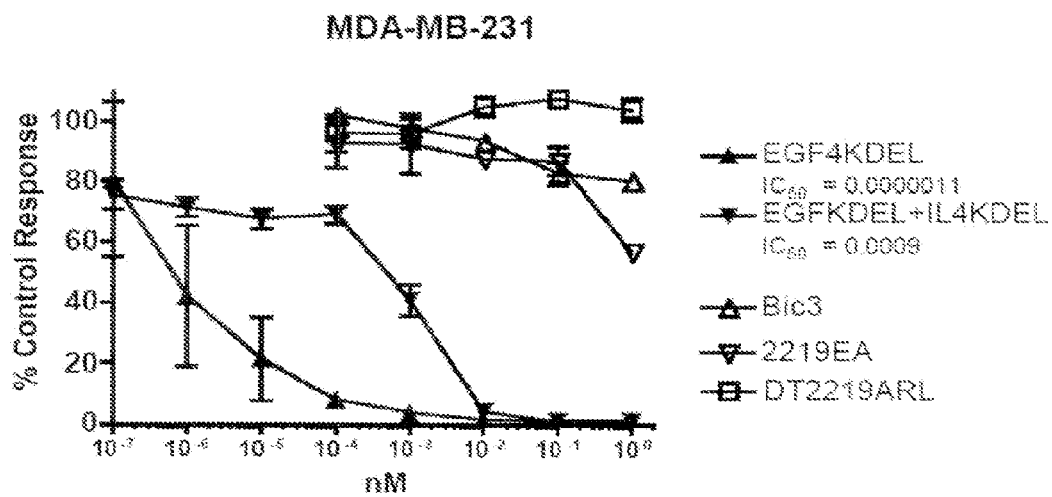

To determine the specificity of the activity of the EGF4KDEL immunotoxin, MDA-MB-231 human breast cancer cells were treated with various concentrations of EGF4KDEL, IL4KDEL and EGFKDEL, or Bic3, 2219EA, and DT2219ARL controls and the effect of the immunotoxins on their growth was measured. The Bic3, DT2219ARL, and 2219EA bispecific immunotoxins do not bind to these breast cancer cells. Whereas, EGF4KDEL was again highly effective at killing the breast cancer cells having an 1050 of 0.0000011, Bic3, DT2219ARL, and 2219EA had minimal killing effect against MDA-MB-231 cells (FIG. 25B).

Figure 25C:
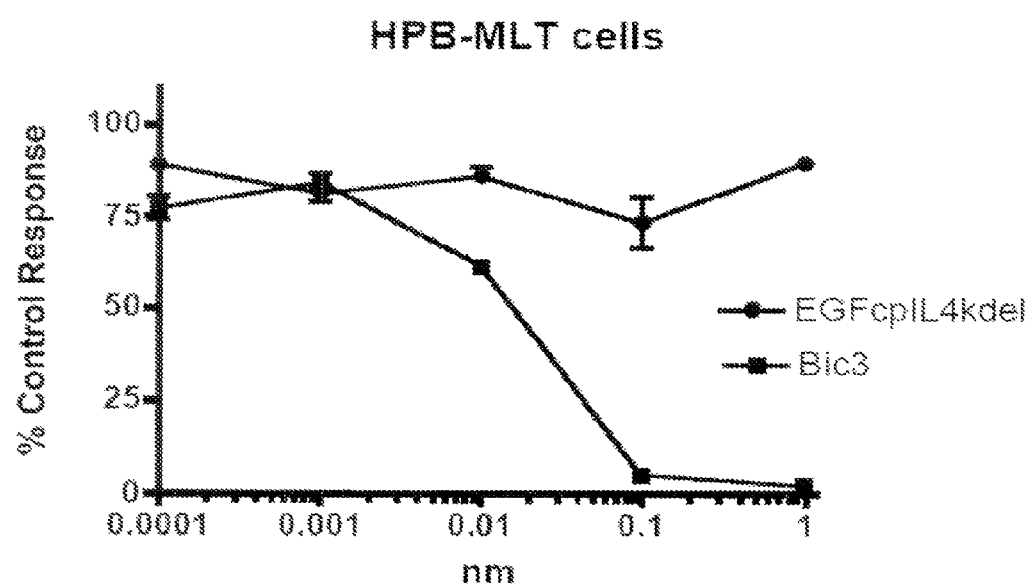

In another experiment. HPB-MLT cells, a human T cell line that does not express EGFR or IL4R, were treated with EGF4KDEL and Bic3 and the effect on their growth was measured. HPBMLT cell growth while significantly affected by the Bic3 positive control reagent, was only minimally inhibited by EGF4KDEL (FIG. 25C). These results suggest that the EGF4KDEL reagent is effective and specific in killing cells expressing an EGFR and an IL4R.

Example 17

Figure 26:
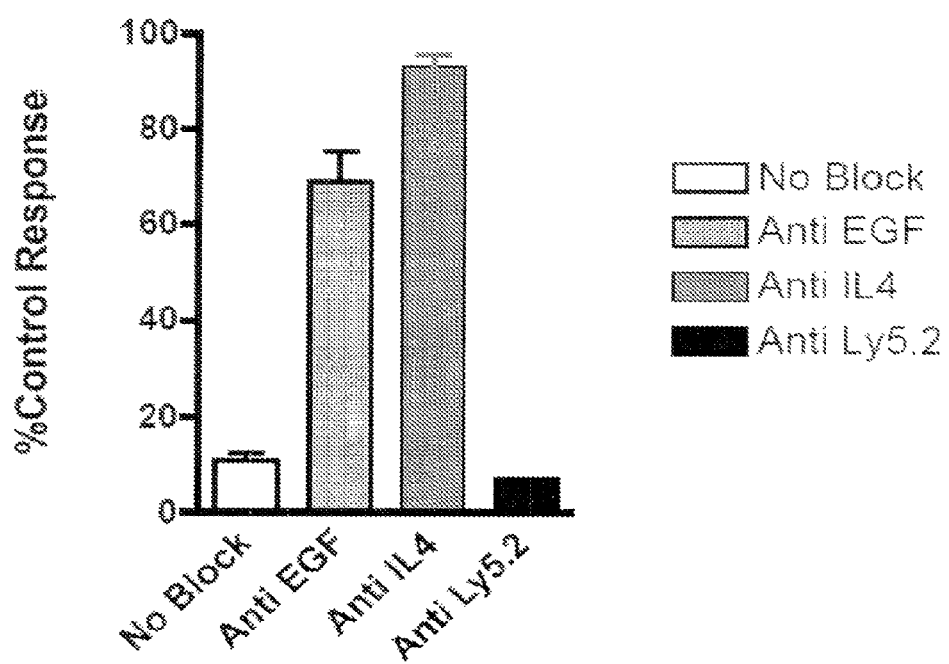

Determining the Ability of Anti-EGF and Anti-IL4 Antibodies to Block EGF4 KDEL-Induced Killing To confirm that EGF and IL4 were both important for EGF4KDEL-induced killing of MDQ-MB-231 cells, a blocking experiment was performed. 50 μg/ml of anti-EGF or anti-IL4 antibodies were tested for their ability to block the killing of the cells by EGF4KDEL (FIG. 26). EGF4KDEL (0.1 nM) was cultured with the cells for 72 hours in the presence or absence of an anti-EGF antibody, an anti-IL4 antibody, or a control antibody (Ly5.2). When either antibody was added to EGF4KDEL. both antibodies were capable of blocking about 70-85% of the anti-proliferative effect. In contrast, the addition of control anti-mouse Ly5.2 antibodies had no blocking effect.

Taken together, these data indicated that both ligands (EGF and IL4) were important for the activity of the EGF4 KDEL molecule.

Example 18

Effect of DTEGF4 on MDA-MB-231 Cancer Cell Growth

Figure 27:
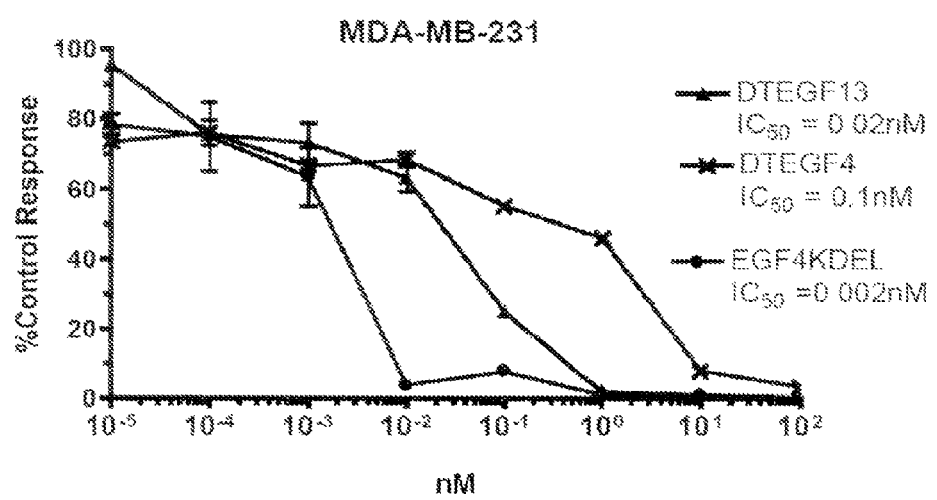

To determine whether an EGF4 construct containing a *Diptheria* toxin as a toxic region was also capable of killing MDA-MB-231 cells, a nucleic acid encoding the first 389 amino acids of the *Diphtheria* toxin (DT) molecule, a nucleotide sequence encoding the 7 amino acid EASGGPE (SEQ ID NO:14) linker, nucleotide sequences encoding human epidermal growth factor (EGF), the nucleotide sequence encoding a 20 amino acid segment (PSGQAGAAASESLFVSN-HAY (SEQ ID NO:13) of human muscle aldolase (hma), a nucleotide sequence encoding an interleukin 4 (IL4) was constructed. MDA-MB-231 cells were treated with various concentrations of EGF4 KDEL, DTEGF4, and DTEGF13 immunotoxins and the effect of the toxins on their growth was measured. Each of EGF4 KDEL, DTEGF4, and DTEGF13 was highly effective at killing the breast cancer cells having an $IC_{50}$ of 0.002 nM, 0.1 nM, and 0.02 nM respectively (FIG. 27).

These data indicated that the bispecific EGF4 molecule containing at least two different toxins is effective at killing tumor cells.

Example 19

EGF4 KDEL in a MDA-MB-231 Intratumoral Nude Mouse Tumor Model

Figure 28:
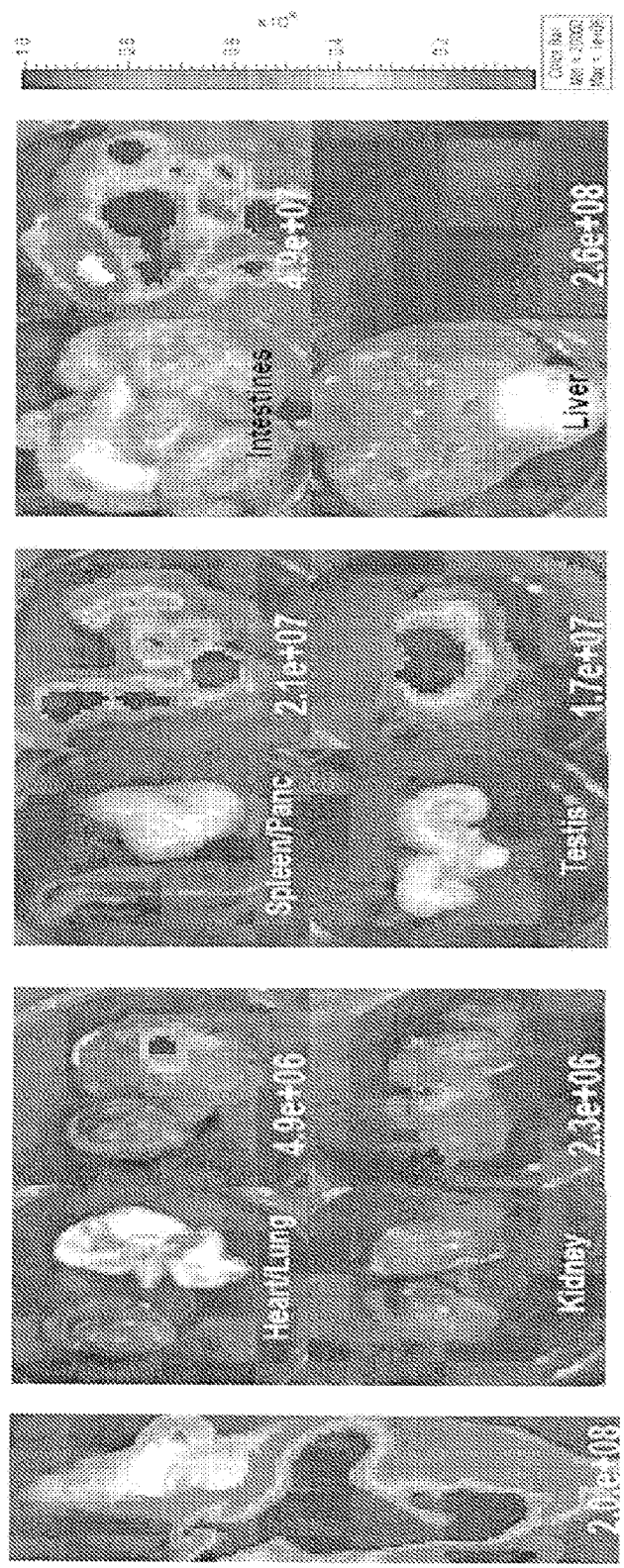

To test the ability of EGF4 KDEL to inhibit breast tumor growth in vivo, MDA-MB-231 human breast cancer cells were xenografted into the spleen of nude mice. The MDA-MB-231 cells contained, and stably expressed, an exogenous nucleic acid encoding a firefly luciferase protein (MDA-MB-231-luc cells). $1 \times 10^6$ MDA-MB-231-luc cells were administered to the mice by intrasplenic (IS) injection. On day 61, organs were removed and imaged by fluorescence spectroscopy to determine the location of developing tumors (FIG. 28). This data indicates that intrasplenic injection results in a model whereby MDA-MB-231-luc cells metastasize to the liver, and to other organs, where it stably and slowly grows.

Figure 29A:
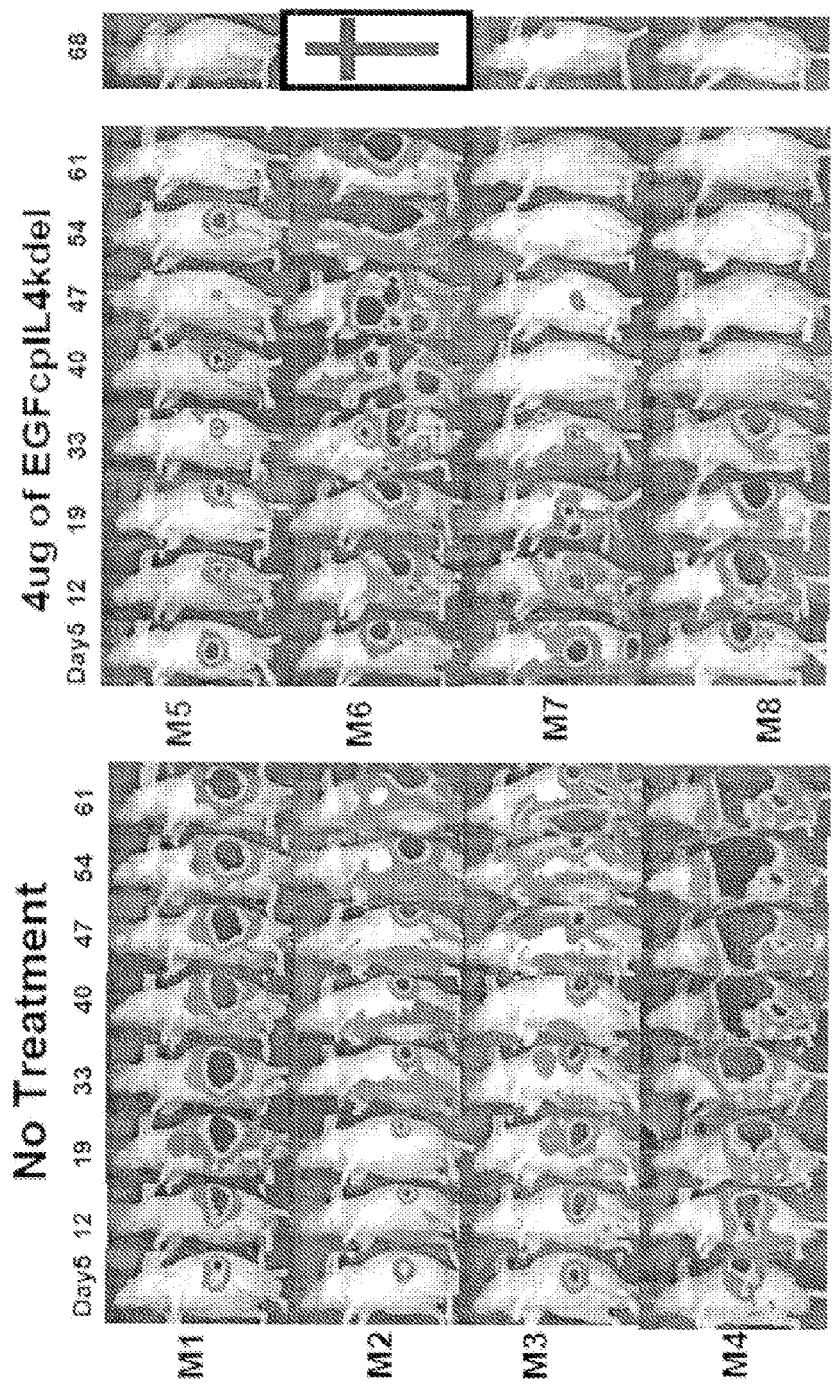
FIGS. 29A and 29B are a series of photographs of fluorescence images of mice bearing MDA-MB-231-luc cells and either not treated (FIG. 29A, left panel), treated with 4 micrograms (4 ug) of EGF4 KDEL ("EGF4 cpIL4 kdel"), or treated with Bic 3 as a negative control (FIG. 29B) four days a week for each of nine weeks. Mice were imaged as described in FIG. 28. The photograph of the cross indicates death of the test animal. The number of days following injection of the cells is shown at the top of each column of photographs (FIG. 29A). A mouse having a tumor that did not respond to treatment with EGF4 KDEL is shown in the right panel as "M6" of FIG. 29A.
Figure 29B:
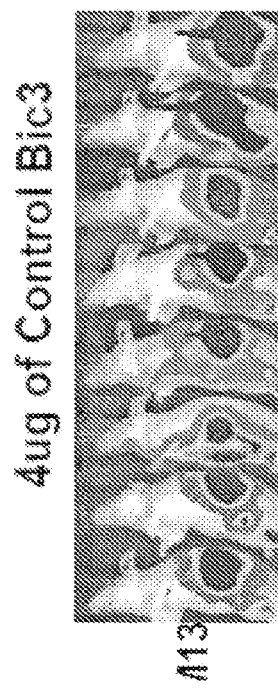
Figures 29C, 29D:
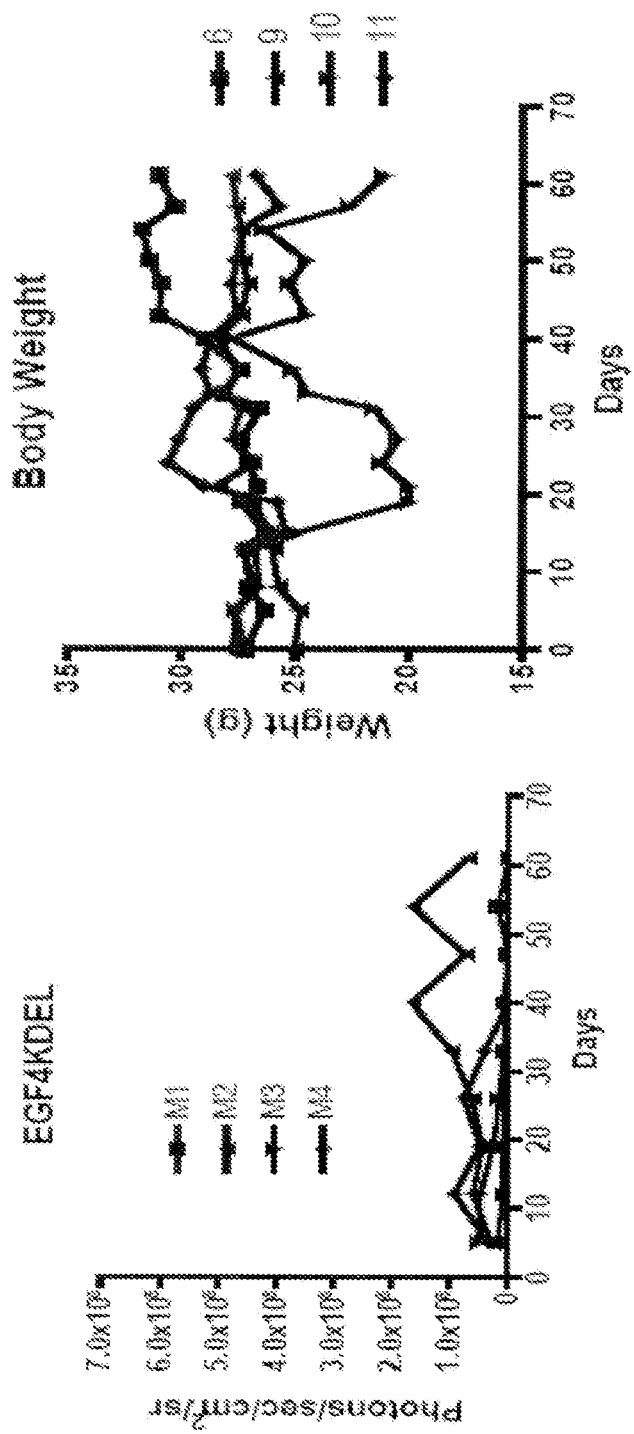
FIG. 29C is a line graph depicting growth of MDA-MB-231-luc tumors in the four mice treated with EGF4 KDEL. The X-axis indicates the number of days following injection of the tumor cells and the Y-axis indicates the extent of tumor growth as measured by bioluminescence produced from the tumor of each mouse in units of photons/sec/cm2/sr.
FIG. 29D is a line graph depicting the toxicity of the EGF4 KDEL treatment in mice (FIGS. 29A and 29B). Mouse weight in grams is indicated on the Y-axis and the number of days following injection of the cells is indicated on the X-axis. Data from the mouse that did not respond to treatment with EGF4 KDEL (in FIG. 29A) is shown and is identified in the graph as "11."

In another experiment, $1 \times 10^6$ MDA-MB-231-luc cells were administered to mice (N=4) by IS injection. The mice were also administered by i.p. 4 μg of EGF4 KDEL, or Bic protein (above), for four days each week for nine weeks. Inhibition of tumor development was observed in 3 of 4 mice (75%) treated with EGF4 KDEL and two of the mice showed no evidence of a tumor on day 68 (FIGS. 29A and C). Tumors of mice receiving the negative control Bic3 did not respond to therapy (FIG. 29B). There was no significant weight loss in the responder mice, but there was a weight change in the mouse that did not respond to therapy (FIG. 29C).

In another experiment, $1 \times 10^6$ MDA-MB-231-luc cells were administered to mice by IS injection. The mice were also administered by i.p. 4 μg of EGF4 KDEL, or 2219ARLKDEL control protein (above), for four days each week for nine weeks. Inhibition of tumor growth was observed in mice treated with EGF4 KDEL, whereas tumors of mice receiving the negative control 2219ARLKDEL toxin did not respond to therapy.

Together, these studies show that in a model in which the human EGF and IL-4 of EGF4 KDEL are cross-reactive with mouse EGFR and IL4R, EGF4 KDEL is a highly effective anti-tumor agent. The reagent is highly effective against human breast cancer and that both EGF and IL4 moieties present in the same molecule contribute to its superior anti-tumor effect.

Example 20

Effect of Pre-Dosing in an In Vivo Tumor Model

Figures 30A, 30B:
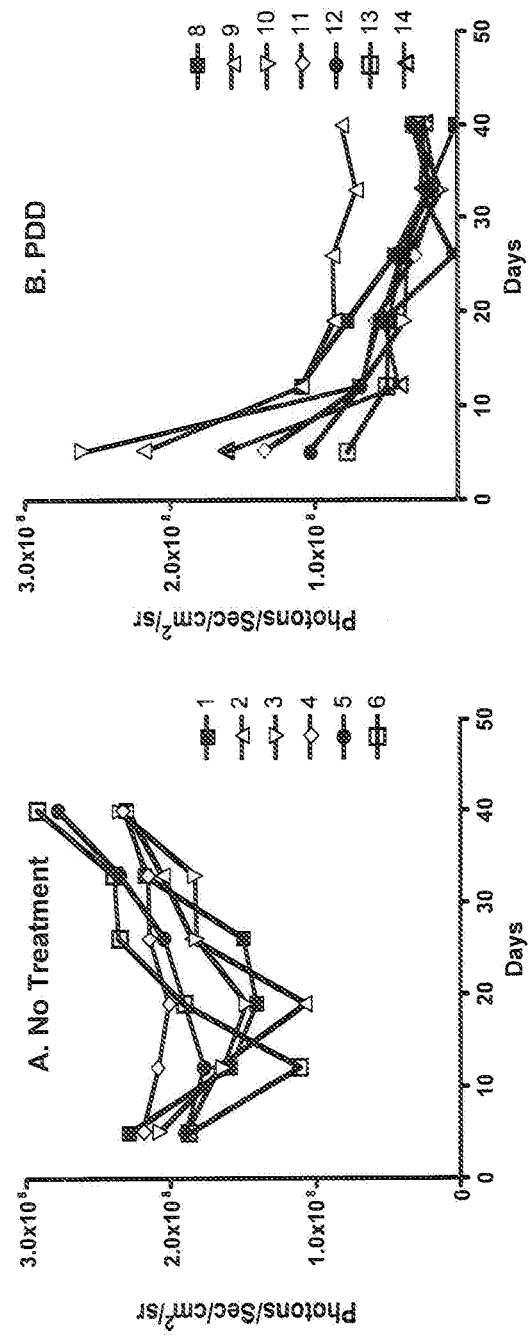
FIGS. 30A and 30B are a pair of line graphs depicting the effect of pre-treatment with a non-toxic bispecific immunotoxin on the efficacy of DTEGF13 towards human pancreatic tumors in mice. MiaPaCa-2-luc human pancreatic cancer cells expressing luciferase protein were injected into the spleen of nude mice and the mice were either not treated (FIG. 30A) or treated (FIG. 30B) with 7.5 µg DTEGF13. Mice treated with DTEGF13 were administered 200 µg of EGF13 (not containing a toxic domain) around 30 minutes prior to the DTEGF13 treatment. The X-axis indicates the number of days following injection of the tumor cells and the Y-axis indicates the extent of tumor growth as measured by bioluminescence produced from the tumor of each mouse in units of photons/sec/cm2/sr.
Figure 31:
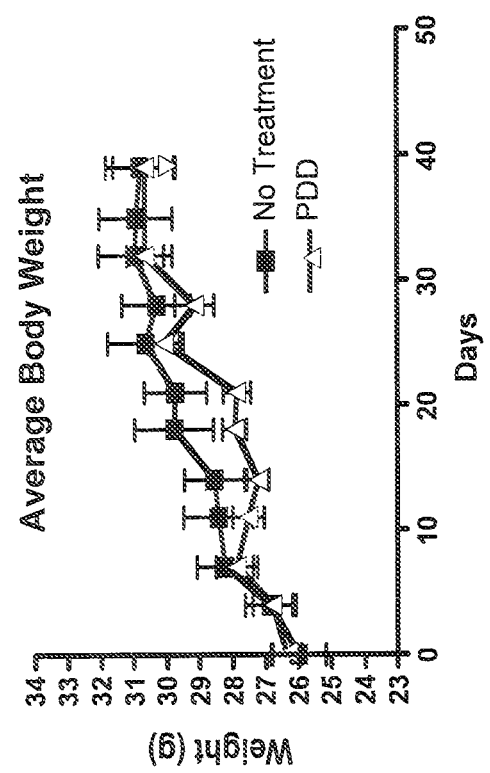
FIG. 31 is a line graph depicting the toxicity in mice of the treatment described in FIGS. 30A and B. Mouse weight in grams is indicated on the Y-axis and the number of days following injection of the cells is indicated on the X-axis. "PDD" indicates treatment with both EGF13 and DTEGF13 as described above.

The above studies (Example 12) demonstrated that pre-dosing animals with a non-toxic bispecific molecule prior to administering the bispecific molecule containing a toxin was effective to reduce toxicity associated with the bispecific immunotoxin molecule in normal mice. To test the efficacy of pre-dosing (or profectitious drug delivery or PDD) in an in vivo tumor model, the MiaPaCa-2 orthotopic pancreatic cancer model was used. The MiaPaCa-2 cells contained, and stably expressed, an exogenous nucleic acid encoding a firefly luciferase protein (MiaPaCa-2-luc cells). $1 \times 106$ MiaPaCa-2-luc-luc cells were administered to the pancreas of mice by injection. The mice were also administered by i.p. injection 7.5 μg DTEGF13 or 200 μg EGF13 and 7.5 μg DTEGF13. in animals receiving both EGF13 and DTEGF13, the EGF13 injection was performed about 30 minutes prior to injection of the DTEGF13 protein. The animals received 3 injections QOD for five weeks. Whereas the animals that did not receive treatment showed progressing pancreatic cancer (FIG. 30A), animals receiving the predose of non-immunotoxic EGF13 showed dramatic reduction in tumor burden (FIG. 30B). The PDD was also effective in reducing toxicity as determined by body weight of the animals. Each injection of DTEGF13 exceeded the MTD by 15 fold and animals received a total 15 injections. Despite this, average body weights of the animals in the PDD group above (mice 8-14) did not decrease (FIG. 31) indicating the regimen had minimal toxicity.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What I claim is:

1. A receptor-targeting reagent comprising SEQ ID NO:2 or SEQ ID NO:20.

2. A linear fusion protein immunotoxic receptor-targeting reagent comprising SEQ ID NO: 1, SEQ ID NO:3, SEQ ID NO:18, or SEQ ID NO:19.

3. A pharmaceutical composition comprising the receptor-targeting reagent of claim 1 and a pharmaceutically acceptable carrier.

4. A kit comprising:
the receptor-targeting reagent of claim 1; and
instructions for administering the receptor-targeting reagent.

5. A pharmaceutical composition comprising the receptor-targeting reagent of claim 2 and a pharmaceutically acceptable carrier.

6. A kit comprising:
the receptor-targeting reagent of claim 2; and
instructions for administering the composition.

7. An in vitro method for binding a receptor-targeting reagent to a cell, the method comprising contacting a cell with a receptor-targeting reagent of claim 1.

8. An in vivo method for binding a receptor-targeting reagent to a cell, the method comprising delivering to a subject the receptor-targeting reagent of claim 1.

9. The method of claim 8, wherein the subject is a mammal.

10. The method of claim 9, wherein the subject is a human.

11. The method of claim 8, further comprising determining whether the subject has a cancer.

12. The method of claim 8, wherein the subject has a cancer.

13. The method of claim 12, wherein the cancer is lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

14. The method of claim 12, wherein the cancer is a glioblastoma.

15. The method of claim 12, further comprising determining if one or more cells of the cancer express an EGFR, an IL13R, or an IL4R.

* * * * *

UNITED STATES PATENT AND TRADEMARK OFFICE
CERTIFICATE OF CORRECTION

Page 1 of 1

PATENT NO. : 9,155,798 B2
APPLICATION NO. : 12/675081
DATED : October 13, 2015
INVENTOR(S) : Vallera It is certified that error appears in the above-identified patent and that said Letters Patent is hereby corrected as shown below:

In the Specification

Column 1, Lines 20-24, Delete "The research described in this application was supported by U.S. Public Health Service grants (grant nos. RO1-CA36725, RO1-CA082154, and R01-108637) from the National Cancer Institute of the National Institutes of Health. Thus, the government has certain rights in the invention." and insert -- This invention was made with government support under R01-CA036725, R01-CA082154, and R01-CA108637 awarded by the National Institutes of Health. The government has certain rights in the invention. --, therefor.

In the Claims

Column 97, Line 23, In Claim 2, delete "NO: 1," and insert -- NO:1, --, therefor.

Signed and Sealed this
Twenty-second Day of March, 2016

Michelle K. Lee
*Director of the United States Patent and Trademark Office*

SEQUENCE LISTING

<160> NUMBER OF SEQ ID NOS: 22

<210> SEQ ID NO 1
<211> LENGTH: 582
<212> TYPE: PRT
<213> ORGANISM: Artificial Sequence
<220> FEATURE:
<223> OTHER INFORMATION: synthetically generated polypeptide

<400> SEQUENCE: 1

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu

```
                355                 360                 365
        Phe Gln Val His Asn Ser Tyr Asn Arg Pro Ala Tyr Ser Pro Gly
        370                 375                 380
His Lys Thr Gln Pro Phe Glu Ala Ser Gly Gly Pro Glu Asn Ser Asp
385                 390                 395                 400
Ser Glu Cys Pro Leu Ser His Asp Gly Tyr Cys Leu His Asp Gly Val
                405                 410                 415
Cys Met Tyr Ile Glu Ala Leu Asp Lys Tyr Ala Cys Asn Cys Val Val
            420                 425                 430
Gly Tyr Ile Gly Glu Arg Cys Gln Tyr Arg Asp Leu Lys Trp Trp Glu
        435                 440                 445
Leu Arg Pro Ser Gly Gln Ala Gly Ala Ala Ser Glu Ser Leu Phe
    450                 455                 460
Val Ser Asn His Ala Tyr Gly Pro Val Pro Pro Ser Thr Ala Leu Arg
465                 470                 475                 480
Glu Leu Ile Glu Glu Leu Val Asn Ile Thr Gln Asn Gln Lys Ala Pro
                485                 490                 495
Leu Cys Asn Gly Ser Met Val Trp Ser Ile Asn Leu Thr Ala Gly Met
            500                 505                 510
Tyr Cys Ala Ala Leu Glu Ser Leu Ile Asn Val Ser Gly Cys Ser Ala
        515                 520                 525
Ile Glu Lys Thr Gln Arg Met Leu Ser Gly Phe Cys Pro His Lys Val
530                 535                 540
Ser Ala Gly Gln Phe Ser Ser Leu His Val Arg Asp Thr Lys Ile Glu
545                 550                 555                 560
Val Ala Gln Phe Val Lys Asp Leu Leu Leu His Leu Lys Lys Leu Phe
                565                 570                 575
Arg Glu Gly Arg Phe Asn
            580

<210> SEQ ID NO 2
<211> LENGTH: 185
<212> TYPE: PRT
<213> ORGANISM: Artificial Sequence
<220> FEATURE:
<223> OTHER INFORMATION: synthetically generated polypeptide

<400> SEQUENCE: 2

Asn Ser Asp Ser Glu Cys Pro Leu Ser His Asp Gly Tyr Cys Leu His
1               5                   10                  15
Asp Gly Val Cys Met Tyr Ile Glu Ala Leu Asp Lys Tyr Ala Cys Asn
            20                  25                  30
Cys Val Val Gly Tyr Ile Gly Glu Arg Cys Gln Tyr Arg Asp Leu Lys
        35                  40                  45
Trp Trp Glu Leu Arg Pro Ser Gly Gln Ala Gly Ala Ala Ser Glu
    50                  55                  60
Ser Leu Phe Val Ser Asn His Ala Tyr Gly Pro Val Pro Pro Ser Thr
65                  70                  75                  80
Ala Leu Arg Glu Leu Ile Glu Glu Leu Val Asn Ile Thr Gln Asn Gln
                85                  90                  95
Lys Ala Pro Leu Cys Asn Gly Ser Met Val Trp Ser Ile Asn Leu Thr
            100                 105                 110
Ala Gly Met Tyr Cys Ala Ala Leu Glu Ser Leu Ile Asn Val Ser Gly
        115                 120                 125
Cys Ser Ala Ile Glu Lys Thr Gln Arg Met Leu Ser Gly Phe Cys Pro
```

```
            130                 135                 140
His Lys Val Ser Ala Gly Gln Phe Ser Ser Leu His Val Arg Asp Thr
145                 150                 155                 160

Lys Ile Glu Val Ala Gln Phe Val Lys Asp Leu Leu Leu His Leu Lys
                165                 170                 175

Lys Leu Phe Arg Glu Gly Arg Phe Asn
            180                 185

<210> SEQ ID NO 3
<211> LENGTH: 556
<212> TYPE: PRT
<213> ORGANISM: Artificial Sequence
<220> FEATURE:
<223> OTHER INFORMATION: synthetically generated polypeptide

<400> SEQUENCE: 3

Met Glu Asn Ser Asp Ser Glu Cys Pro Leu Ser His Asp Gly Tyr Cys
1               5                   10                  15

Leu His Asp Gly Val Cys Met Tyr Ile Glu Ala Leu Asp Lys Tyr Ala
            20                  25                  30

Cys Asn Cys Val Val Gly Tyr Ile Gly Glu Arg Cys Gln Tyr Arg Asp
        35                  40                  45

Leu Lys Trp Trp Glu Leu Arg Pro Ser Gly Gln Ala Gly Ala Ala Ala
    50                  55                  60

Ser Glu Ser Leu Phe Val Ser Asn His Ala Tyr Gly Pro Val Pro Pro
65                  70                  75                  80

Ser Thr Ala Leu Arg Glu Leu Ile Glu Glu Leu Val Asn Ile Thr Gln
                85                  90                  95

Asn Gln Lys Ala Pro Leu Cys Asn Gly Ser Met Val Trp Ser Ile Asn
            100                 105                 110

Leu Thr Ala Gly Met Tyr Cys Ala Ala Leu Glu Ser Leu Ile Asn Val
        115                 120                 125

Ser Gly Cys Ser Ala Ile Glu Lys Thr Gln Arg Met Leu Ser Gly Phe
    130                 135                 140

Cys Pro His Lys Val Ser Ala Gly Gln Phe Ser Ser Leu His Val Arg
145                 150                 155                 160

Asp Thr Lys Ile Glu Val Ala Gln Phe Val Lys Asp Leu Leu Leu His
                165                 170                 175

Leu Lys Lys Leu Phe Arg Glu Gly Arg Phe Asn Glu Ala Ser Gly Gly
            180                 185                 190

Pro Glu Pro Glu Gly Gly Ser Leu Ala Ala Leu Thr Ala His Gln Ala
        195                 200                 205

Cys His Leu Pro Leu Glu Thr Phe Thr Arg His Arg Gln Pro Arg Gly
    210                 215                 220

Trp Glu Gln Leu Glu Gln Cys Gly Tyr Pro Val Gln Arg Leu Val Ala
225                 230                 235                 240

Leu Tyr Leu Ala Ala Arg Leu Ser Trp Asn Gln Val Asp Gln Val Ile
                245                 250                 255

Arg Asn Ala Leu Ala Ser Pro Gly Ser Gly Gly Asp Leu Gly Glu Ala
            260                 265                 270

Ile Arg Glu Gln Pro Glu Gln Ala Arg Leu Ala Leu Thr Leu Ala Ala
        275                 280                 285

Ala Glu Ser Glu Arg Phe Val Arg Gln Gly Thr Gly Asn Asp Glu Ala
    290                 295                 300

Gly Ala Ala Asn Ala Asp Val Val Ser Leu Thr Cys Pro Val Ala Ala
```

```
                    305                 310                 315                 320
Gly Glu Cys Ala Gly Pro Ala Asp Ser Gly Asp Ala Leu Leu Glu Arg
                325                 330                 335

Asn Tyr Pro Thr Gly Ala Glu Phe Leu Gly Asp Gly Gly Asp Val Ser
            340                 345                 350

Phe Ser Thr Arg Gly Thr Gln Asn Trp Thr Val Glu Arg Leu Leu Gln
        355                 360                 365

Ala His Arg Gln Leu Glu Glu Arg Gly Tyr Val Phe Val Gly Tyr His
    370                 375                 380

Gly Thr Phe Leu Glu Ala Ala Gln Ser Ile Val Phe Gly Gly Val Arg
385                 390                 395                 400

Ala Arg Ser Gln Asp Leu Asp Ala Ile Trp Arg Gly Phe Tyr Ile Ala
                405                 410                 415

Gly Asp Pro Ala Leu Ala Tyr Gly Tyr Ala Gln Asp Gln Glu Pro Asp
            420                 425                 430

Ala Arg Gly Arg Ile Arg Asn Gly Ala Leu Leu Arg Val Tyr Val Pro
        435                 440                 445

Arg Ser Ser Leu Pro Gly Phe Tyr Arg Thr Ser Leu Thr Leu Ala Ala
    450                 455                 460

Pro Glu Ala Ala Gly Glu Val Glu Arg Leu Ile Gly His Pro Leu Pro
465                 470                 475                 480

Leu Arg Leu Asp Ala Ile Thr Gly Pro Glu Glu Gly Gly Arg Leu
                485                 490                 495

Glu Thr Ile Leu Gly Trp Pro Leu Ala Glu Arg Thr Val Val Ile Pro
            500                 505                 510

Ser Ala Ile Pro Thr Asp Pro Arg Asn Val Gly Gly Asp Leu Asp Pro
        515                 520                 525

Ser Ser Ile Pro Asp Lys Glu Gln Ala Ile Ser Ala Leu Pro Asp Tyr
    530                 535                 540

Ala Ser Gln Pro Gly Lys Pro Pro Lys Asp Glu Leu
545                 550                 555

<210> SEQ ID NO 4
<211> LENGTH: 18
<212> TYPE: PRT
<213> ORGANISM: Artificial Sequence
<220> FEATURE:
<223> OTHER INFORMATION: synthetically generated polypeptide

<400> SEQUENCE: 4

Gly Ser Thr Ser Gly Ser Gly Lys Pro Gly Ser Gly Glu Gly Ser Thr
1               5                   10                  15

Lys Gly

<210> SEQ ID NO 5
<211> LENGTH: 15
<212> TYPE: PRT
<213> ORGANISM: Artificial Sequence
<220> FEATURE:
<223> OTHER INFORMATION: synthetically generated polypeptide

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 53
<212> TYPE: PRT
```

<213> ORGANISM: Homo sapiens

<400> SEQUENCE: 6

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 7
<211> LENGTH: 112
<212> TYPE: PRT
<213> ORGANISM: Homo sapiens

<400> SEQUENCE: 7

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 8
<211> LENGTH: 32
<212> TYPE: PRT
<213> ORGANISM: Corynebacterium diphtheriae

<400> SEQUENCE: 8

Met Leu Val Arg Gly Tyr Val Val Ser Arg Lys Leu Phe Ala Ser Ile
1               5                   10                  15

Leu Ile Gly Ala Leu Leu Gly Ile Gly Ala Pro Pro Ser Ala His Ala
            20                  25                  30

<210> SEQ ID NO 9
<211> LENGTH: 567
<212> TYPE: PRT
<213> ORGANISM: Corynebacterium diphtheriae

<400> SEQUENCE: 9

Met Leu Val Arg Gly Tyr Val Val Ser Arg Lys Leu Phe Ala Ser Ile
1               5                   10                  15

Leu Ile Gly Ala Leu Leu Gly Ile Gly Ala Pro Pro Ser Ala His Ala
            20                  25                  30

Gly Ala Asp Asp Val Val Asp Ser Ser Lys Ser Phe Val Met Glu Asn
            35                  40                  45

Phe Ser Ser Tyr His Gly Thr Lys Pro Gly Tyr Val Asp Ser Ile Gln
50 55 60

```
Lys Gly Ile Gln Lys Pro Lys Ser Gly Thr Gln Gly Asn Tyr Asp Asp
 65                  70                  75                  80
Asp Trp Lys Gly Phe Tyr Ser Thr Asp Asn Lys Tyr Asp Ala Ala Gly
                 85                  90                  95
Tyr Ser Val Asp Asn Glu Asn Pro Leu Ser Gly Lys Ala Gly Gly Val
            100                 105                 110
Val Lys Val Thr Tyr Pro Gly Leu Thr Lys Val Leu Ala Leu Lys Val
        115                 120                 125
Asp Asn Ala Glu Thr Ile Lys Lys Glu Leu Gly Leu Ser Leu Thr Glu
130                 135                 140
Pro Leu Met Glu Gln Val Gly Thr Glu Glu Phe Ile Lys Arg Phe Gly
145                 150                 155                 160
Asp Gly Ala Ser Arg Val Val Leu Ser Leu Pro Phe Ala Glu Gly Ser
                165                 170                 175
Ser Ser Val Glu Tyr Ile Asn Asn Trp Glu Gln Ala Lys Ala Leu Ser
            180                 185                 190
Val Glu Leu Glu Ile Asn Phe Glu Thr Arg Gly Lys Arg Gly Gln Asp
        195                 200                 205
Ala Met Tyr Glu Tyr Met Ala Gln Ala Cys Ala Gly Asn Arg Val Arg
210                 215                 220
Arg Ser Val Gly Ser Ser Leu Ser Cys Ile Asn Leu Asp Trp Asp Val
225                 230                 235                 240
Ile Arg Asp Lys Thr Lys Thr Lys Ile Glu Ser Leu Lys Glu His Gly
                245                 250                 255
Pro Ile Lys Asn Lys Met Ser Glu Ser Pro Asn Lys Thr Val Ser Glu
            260                 265                 270
Glu Lys Ala Lys Gln Tyr Leu Glu Glu Phe His Gln Thr Ala Leu Glu
        275                 280                 285
His Pro Glu Leu Ser Glu Leu Lys Thr Val Thr Gly Thr Asn Pro Val
290                 295                 300
Phe Ala Gly Ala Asn Tyr Ala Ala Trp Ala Val Asn Val Ala Gln Val
305                 310                 315                 320
Ile Asp Ser Glu Thr Ala Asp Asn Leu Glu Lys Thr Thr Ala Ala Leu
                325                 330                 335
Ser Ile Leu Pro Gly Ile Gly Ser Val Met Gly Ile Ala Asp Gly Ala
            340                 345                 350
Val His His Asn Thr Glu Glu Ile Val Ala Gln Ser Ile Ala Leu Ser
        355                 360                 365
Ser Leu Met Val Ala Gln Ala Ile Pro Leu Val Gly Glu Leu Val Asp
370                 375                 380
Ile Gly Phe Ala Ala Tyr Asn Phe Val Glu Ser Ile Ile Asn Leu Phe
385                 390                 395                 400
Gln Val Val His Asn Ser Tyr Asn Arg Pro Ala Tyr Ser Pro Gly His
                405                 410                 415
Lys Thr Gln Pro Phe Leu His Asp Gly Tyr Ala Val Ser Trp Asn Thr
            420                 425                 430
Val Glu Asp Ser Ile Ile Arg Thr Gly Phe Gln Gly Glu Ser Gly His
        435                 440                 445
Asp Ile Lys Ile Thr Ala Glu Asn Thr Pro Leu Pro Ile Ala Gly Val
450                 455                 460
Leu Leu Pro Thr Ile Pro Gly Lys Leu Asp Val Asn Lys Ser Lys Thr
465                 470                 475                 480
His Ile Ser Val Asn Gly Arg Lys Ile Arg Met Arg Cys Arg Ala Ile
```

-continued

```
                485                 490                 495

Asp Gly Asp Val Thr Phe Cys Arg Pro Lys Ser Pro Val Tyr Val Gly
            500                 505                 510

Asn Gly Val His Ala Asn Leu His Val Ala Phe His Arg Ser Ser Ser
        515                 520                 525

Glu Lys Ile His Ser Asn Glu Ile Ser Ser Asp Ser Ile Gly Val Leu
    530                 535                 540

Gly Tyr Gln Lys Thr Val Asp His Thr Lys Val Asn Ser Lys Leu Ser
545                 550                 555                 560

Leu Phe Phe Glu Ile Lys Ser
                565

<210> SEQ ID NO 10
<211> LENGTH: 390
<212> TYPE: PRT
<213> ORGANISM: Corynebacterium diphtheriae

<400> SEQUENCE: 10

Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

```
Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
    370                 375                 380

His Lys Thr Gln Pro Phe
385                 390

<210> SEQ ID NO 11
<211> LENGTH: 638
<212> TYPE: PRT
<213> ORGANISM: Pseudomonas aeruginosa

<400> SEQUENCE: 11

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
                20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
50                  55                  60

Gln Gly Val Leu His Tyr Ser Met Val Leu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270
```

Leu His Phe Pro Glu Gly Gly Ser Leu Ala Ala Leu Thr Ala His Gln
    275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Gly Asp Val
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Ser Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605

Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635

<210> SEQ ID NO 12
<211> LENGTH: 362
<212> TYPE: PRT
<213> ORGANISM: Pseudomonas aeruginosa

<400> SEQUENCE: 12

Pro Glu Gly Gly Ser Leu Ala Ala Leu Thr Ala His Gln Ala Cys His

```
                1               5                  10                 15
            Leu Pro Leu Glu Thr Phe Thr Arg His Arg Gln Pro Arg Gly Trp Glu
                            20                 25                 30

Gln Leu Glu Gln Cys Gly Tyr Pro Val Gln Arg Leu Val Ala Leu Tyr
                        35                 40                 45

Leu Ala Arg Leu Ser Trp Asn Gln Val Asp Gln Val Ile Arg Asn
             50                 55                 60

Ala Leu Ala Ser Pro Gly Ser Gly Gly Asp Leu Gly Glu Ala Ile Arg
             65                 70                 75                 80

Glu Gln Pro Glu Gln Ala Arg Leu Ala Leu Thr Leu Ala Ala Ala Glu
                            85                 90                 95

Ser Glu Arg Phe Val Arg Gln Gly Thr Gly Asn Asp Glu Ala Gly Ala
                        100                105                110

Ala Asn Ala Asp Val Val Ser Leu Thr Cys Pro Val Ala Ala Gly Glu
                        115                120                125

Cys Ala Gly Pro Ala Asp Ser Gly Asp Ala Leu Leu Glu Arg Asn Tyr
                        130                135                140

Pro Thr Gly Ala Glu Phe Leu Gly Asp Gly Asp Val Ser Phe Ser
            145                150                155                160

Thr Arg Gly Thr Gln Asn Trp Thr Val Glu Arg Leu Leu Gln Ala His
                            165                170                175

Arg Gln Leu Glu Glu Arg Gly Tyr Val Phe Val Gly Tyr His Gly Thr
                        180                185                190

Phe Leu Glu Ala Ala Gln Ser Ile Val Phe Gly Gly Val Arg Ala Arg
                        195                200                205

Ser Gln Asp Leu Asp Ala Ile Trp Arg Gly Phe Tyr Ile Ala Gly Asp
                        210                215                220

Pro Ala Leu Ala Tyr Gly Tyr Ala Gln Asp Gln Glu Pro Asp Ala Arg
            225                230                235                240

Gly Arg Ile Arg Asn Gly Ala Leu Leu Arg Val Tyr Val Pro Arg Ser
                            245                250                255

Ser Leu Pro Gly Phe Tyr Arg Thr Ser Leu Thr Leu Ala Ala Pro Glu
                        260                265                270

Ala Ala Gly Glu Val Glu Arg Leu Ile Gly His Pro Leu Pro Leu Arg
                        275                280                285

Leu Asp Ala Ile Thr Gly Pro Glu Glu Glu Gly Gly Arg Leu Glu Thr
                        290                295                300

Ile Leu Gly Trp Pro Leu Ala Glu Arg Thr Val Val Ile Pro Ser Ala
            305                310                315                320

Ile Pro Thr Asp Pro Arg Asn Val Gly Gly Asp Leu Asp Pro Ser Ser
                            325                330                335

Ile Pro Asp Lys Glu Gln Ala Ile Ser Ala Leu Pro Asp Tyr Ala Ser
                        340                345                350

Gln Pro Gly Lys Pro Lys Asp Glu Leu
                        355                360

<210> SEQ ID NO 13
<211> LENGTH: 20
<212> TYPE: PRT
<213> ORGANISM: Homo sapiens

<400> SEQUENCE: 13

Pro Ser Gly Gln Ala Gly Ala Ala Ala Ser Glu Ser Leu Phe Val Ser
 1               5                  10                 15
```

Asn His Ala Tyr
            20

<210> SEQ ID NO 14
<211> LENGTH: 7
<212> TYPE: PRT
<213> ORGANISM: Artificial Sequence
<220> FEATURE:
<223> OTHER INFORMATION: synthetically generated polypeptide

<400> SEQUENCE: 14

Glu Ala Ser Pro Pro Gly Glu
1               5

<210> SEQ ID NO 15
<211> LENGTH: 4
<212> TYPE: PRT
<213> ORGANISM: Homo sapiens

<400> SEQUENCE: 15

Lys Asp Glu Leu
1

<210> SEQ ID NO 16
<211> LENGTH: 25
<212> TYPE: PRT
<213> ORGANISM: Homo sapiens

<400> SEQUENCE: 16

Met Ala Ile Ser Gly Val Pro Val Leu Gly Phe Phe Ile Ile Ala Val
1               5                   10                  15

Leu Met Ser Ala Gln Glu Ser Trp Ala
            20                  25

<210> SEQ ID NO 17
<211> LENGTH: 153
<212> TYPE: PRT
<213> ORGANISM: Homo sapiens

<400> SEQUENCE: 17

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 18
<211> LENGTH: 623
<212> TYPE: PRT
<213> ORGANISM: Artificial Sequence
<220> FEATURE:
<223> OTHER INFORMATION: synthetically generated polypeptide

<400> SEQUENCE: 18

```
Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365
```

Phe Gln Val Val His Asn Ser Tyr Asn Arg Pro Ala Tyr Ser Pro Gly
370                 375                 380

His Lys Thr Gln Pro Phe Glu Ala Ser Gly Gly Pro Glu Asn Ser Asp
385                 390                 395                 400

Ser Glu Cys Pro Leu Ser His Asp Gly Tyr Cys Leu His Asp Gly Val
                405                 410                 415

Cys Met Tyr Ile Glu Ala Leu Asp Lys Tyr Ala Cys Asn Cys Val Val
                420                 425                 430

Gly Tyr Ile Gly Glu Arg Cys Gln Tyr Arg Asp Leu Lys Trp Trp Glu
                435                 440                 445

Leu Arg Pro Ser Gly Gln Ala Gly Ala Ala Ser Glu Ser Leu Phe
450                 455                 460

Val Ser Asn His Ala Tyr Met Gly Leu Thr Ser Gln Leu Leu Pro Pro
465                 470                 475                 480

Leu Phe Phe Leu Leu Ala Cys Ala Gly Asn Phe Val His Gly His Lys
                485                 490                 495

Cys Asp Ile Thr Leu Gln Glu Ile Ile Lys Thr Leu Asn Ser Leu Thr
                500                 505                 510

Glu Gln Lys Thr Leu Cys Thr Glu Leu Thr Val Thr Asp Ile Phe Ala
515                 520                 525

Ala Ser Lys Asn Thr Thr Glu Lys Glu Thr Phe Cys Arg Ala Ala Thr
530                 535                 540

Val Leu Arg Gln Phe Tyr Ser His His Glu Lys Asp Thr Arg Cys Leu
545                 550                 555                 560

Gly Ala Thr Ala Gln Gln Phe His Arg His Lys Gln Leu Ile Arg Phe
                565                 570                 575

Leu Lys Arg Leu Asp Arg Asn Leu Trp Gly Leu Ala Gly Leu Asn Ser
                580                 585                 590

Cys Pro Val Lys Glu Ala Asn Gln Ser Thr Leu Glu Asn Phe Leu Glu
                595                 600                 605

Arg Leu Lys Thr Ile Met Arg Glu Lys Tyr Ser Lys Cys Ser Ser
610                 615                 620

<210> SEQ ID NO 19
<211> LENGTH: 596
<212> TYPE: PRT
<213> ORGANISM: Artificial Sequence
<220> FEATURE:
<223> OTHER INFORMATION: synthetically generated polypeptide

<400> SEQUENCE: 19

Met Asn Ser Asp Ser Glu Cys Pro Leu Ser His Asp Gly Tyr Cys Leu
1               5                   10                  15

His Asp Gly Val Cys Met Tyr Ile Glu Ala Leu Asp Lys Tyr Ala Cys
                20                  25                  30

Asn Cys Val Val Gly Tyr Ile Gly Glu Arg Cys Gln Tyr Arg Asp Leu
                35                  40                  45

Lys Trp Trp Glu Leu Arg Pro Ser Gly Gln Ala Gly Ala Ala Ala Ser
            50                  55                  60

Glu Ser Leu Phe Val Ser Asn His Ala Tyr Met Gly Leu Thr Ser Gln
65              70                  75                  80

Leu Leu Pro Pro Leu Phe Phe Leu Leu Ala Cys Ala Gly Asn Phe Val
                85                  90                  95

His Gly His Lys Cys Asp Ile Thr Leu Gln Glu Ile Ile Lys Thr Leu
                100                 105                 110

-continued

```
Asn Ser Leu Thr Glu Gln Lys Thr Leu Cys Thr Glu Leu Thr Val Thr
        115                 120                 125
Asp Ile Phe Ala Ala Ser Lys Asn Thr Thr Glu Lys Glu Thr Phe Cys
        130                 135                 140
Arg Ala Ala Thr Val Leu Arg Gln Phe Tyr Ser His His Glu Lys Asp
145                 150                 155                 160
Thr Arg Cys Leu Gly Ala Thr Ala Gln Gln Phe His Arg His Lys Gln
                165                 170                 175
Leu Ile Arg Phe Leu Lys Arg Leu Asp Arg Asn Leu Trp Gly Leu Ala
                180                 185                 190
Gly Leu Asn Ser Cys Pro Val Lys Glu Ala Asn Gln Ser Thr Leu Glu
                195                 200                 205
Asn Phe Leu Glu Arg Leu Lys Thr Ile Met Arg Glu Lys Tyr Ser Lys
        210                 215                 220
Cys Ser Ser Glu Ala Ser Gly Gly Pro Glu Pro Gly Gly Ser Leu
225                 230                 235                 240
Ala Ala Leu Thr Ala His Gln Ala Cys His Leu Pro Leu Glu Thr Phe
                245                 250                 255
Thr Arg His Arg Gln Pro Arg Gly Trp Glu Gln Leu Glu Gln Cys Gly
                260                 265                 270
Tyr Pro Val Gln Arg Leu Val Ala Leu Tyr Leu Ala Ala Arg Leu Ser
        275                 280                 285
Trp Asn Gln Val Asp Gln Val Ile Arg Asn Ala Leu Ala Ser Pro Gly
        290                 295                 300
Ser Gly Gly Asp Leu Gly Glu Ala Ile Arg Glu Gln Pro Glu Gln Ala
305                 310                 315                 320
Arg Leu Ala Leu Thr Leu Ala Ala Ala Glu Ser Glu Arg Phe Val Arg
                325                 330                 335
Gln Gly Thr Gly Asn Asp Glu Ala Gly Ala Ala Asn Ala Asp Val Val
                340                 345                 350
Ser Leu Thr Cys Pro Val Ala Ala Gly Glu Cys Ala Gly Pro Ala Asp
                355                 360                 365
Ser Gly Asp Ala Leu Leu Glu Arg Asn Tyr Pro Thr Gly Ala Glu Phe
        370                 375                 380
Leu Gly Asp Gly Gly Asp Val Ser Phe Ser Thr Arg Gly Thr Gln Asn
385                 390                 395                 400
Trp Thr Val Glu Arg Leu Leu Gln Ala His Arg Gln Leu Glu Glu Arg
                405                 410                 415
Gly Tyr Val Phe Val Gly Tyr His Gly Thr Phe Leu Glu Ala Ala Gln
                420                 425                 430
Ser Ile Val Phe Gly Gly Val Arg Ala Arg Ser Gln Asp Leu Asp Ala
        435                 440                 445
Ile Trp Arg Gly Phe Tyr Ile Ala Gly Asp Pro Ala Leu Ala Tyr Gly
        450                 455                 460
Tyr Ala Gln Asp Gln Glu Pro Asp Ala Arg Gly Arg Ile Arg Asn Gly
465                 470                 475                 480
Ala Leu Leu Arg Val Tyr Val Pro Arg Ser Ser Leu Pro Gly Phe Tyr
                485                 490                 495
Arg Thr Ser Leu Thr Leu Ala Ala Pro Glu Ala Ala Gly Glu Val Glu
                500                 505                 510
Arg Leu Ile Gly His Pro Leu Pro Leu Arg Leu Asp Ala Ile Thr Gly
                515                 520                 525
Pro Glu Glu Glu Gly Gly Arg Leu Glu Thr Ile Leu Gly Trp Pro Leu
```

```
                530                 535                 540
Ala Glu Arg Thr Val Val Ile Pro Ser Ala Ile Pro Thr Asp Pro Arg
545                 550                 555                 560

Asn Val Gly Gly Asp Leu Asp Pro Ser Ser Ile Pro Asp Lys Glu Gln
                565                 570                 575

Ala Ile Ser Ala Leu Pro Asp Tyr Ala Ser Gln Pro Gly Lys Pro Pro
            580                 585                 590

Lys Asp Glu Leu
        595

<210> SEQ ID NO 20
<211> LENGTH: 226
<212> TYPE: PRT
<213> ORGANISM: Artificial Sequence
<220> FEATURE:
<223> OTHER INFORMATION: synthetically generated polypeptide

<400> SEQUENCE: 20

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Pro Ser Gly Gln Ala Gly Ala Ala Ser Glu
 50                  55                  60

Ser Leu Phe Val Ser Asn His Ala Tyr Met Gly Leu Thr Ser Gln Leu
 65                  70                  75                  80

Leu Pro Pro Leu Phe Phe Leu Leu Ala Cys Ala Gly Asn Phe Val His
                85                  90                  95

Gly His Lys Cys Asp Ile Thr Leu Gln Glu Ile Ile Lys Thr Leu Asn
            100                 105                 110

Ser Leu Thr Glu Gln Lys Thr Leu Cys Thr Glu Leu Thr Val Thr Asp
        115                 120                 125

Ile Phe Ala Ala Ser Lys Asn Thr Thr Glu Lys Glu Thr Phe Cys Arg
130                 135                 140

Ala Ala Thr Val Leu Arg Gln Phe Tyr Ser His His Glu Lys Asp Thr
145                 150                 155                 160

Arg Cys Leu Gly Ala Thr Ala Gln Gln Phe His Arg His Lys Gln Leu
                165                 170                 175

Ile Arg Phe Leu Lys Arg Leu Asp Arg Asn Leu Trp Gly Leu Ala Gly
            180                 185                 190

Leu Asn Ser Cys Pro Val Lys Glu Ala Asn Gln Ser Thr Leu Glu Asn
        195                 200                 205

Phe Leu Glu Arg Leu Lys Thr Ile Met Arg Glu Lys Tyr Ser Lys Cys
210                 215                 220

Ser Ser
225

<210> SEQ ID NO 21
<211> LENGTH: 18
<212> TYPE: PRT
<213> ORGANISM: Artificial Sequence
<220> FEATURE:
<223> OTHER INFORMATION: synthetically generated polypeptide

<400> SEQUENCE: 21
```

-continued

```
Gly Ser Thr Ser Gly Ser Gly Lys Pro Gly Ser Gly Glu Gly Ser Thr
 1               5                  10                  15
Lys Gly

<210> SEQ ID NO 22
<211> LENGTH: 7
<212> TYPE: PRT
<213> ORGANISM: Artificial Sequence
<220> FEATURE:
<223> OTHER INFORMATION: synthetically generated polypeptide

<400> SEQUENCE: 22

Glu Ala Ser Pro Glu Glu Ala
 1               5
```